(12) United States Patent
Wei et al.

(10) Patent No.: US 11,738,072 B2
(45) Date of Patent: Aug. 29, 2023

(54) TUMOR VACCINE AND USES THEREOF

(71) Applicant: WestVac Biopharma Co., Ltd., Chengdu (CN)

(72) Inventors: Xiawei Wei, Sichuan (CN); Xia Zhao, Sichuan (CN); Yuquan Wei, Sichuan (CN); Zhiwei Zhao, Sichuan (CN)

(73) Assignee: WestVac Biopharma Co., Ltd., Chengdu (CN)

( * ) Notice: Subject to any disclaimer, the term of this patent is extended or adjusted under 35 U.S.C. 154(b) by 530 days.

(21) Appl. No.: 16/625,835

(22) PCT Filed: Jun. 21, 2018

(86) PCT No.: PCT/CN2018/092198
§ 371 (c)(1),
(2) Date: Dec. 23, 2019

(87) PCT Pub. No.: WO2019/001339
PCT Pub. Date: Jan. 3, 2019

(65) Prior Publication Data
US 2020/0121770 A1 Apr. 23, 2020

(30) Foreign Application Priority Data
Jun. 28, 2017 (CN) .......................... 201710509396.6

(51) Int. Cl.
*A61K 39/00* (2006.01)
*A61P 35/00* (2006.01)
*A61K 39/39* (2006.01)
*A61K 45/06* (2006.01)

(52) U.S. Cl.
CPC .......... *A61K 39/0011* (2013.01); *A61K 39/39* (2013.01); *A61K 45/06* (2013.01); *A61P 35/00* (2018.01); *A61K 2039/53* (2013.01); *A61K 2039/55555* (2013.01); *A61K 2039/55572* (2013.01); *A61K 2039/55583* (2013.01); *A61K 2039/6018* (2013.01); *A61K 2039/6087* (2013.01); *A61K 2039/6093* (2013.01)

(58) Field of Classification Search
CPC .... A61K 39/0011; A61K 39/39; A61K 45/06; A61K 2039/53; A61K 2039/55555; A61K 2039/55572; A61K 2039/55583; A61K 2039/6018; A61K 2039/6087; A61K 2039/6093; A61K 39/0005; A61K 2039/572; A61K 2039/585; A61K 2039/55511; A61P 35/00; C12N 15/88; C12N 15/85
See application file for complete search history.

(56) References Cited

U.S. PATENT DOCUMENTS

2005/0002953 A1* 1/2005 Herold ..................... C12N 7/00
435/235.1
2013/0273112 A1* 10/2013 Weiner ................... A61K 38/20
536/23.7

FOREIGN PATENT DOCUMENTS

CN      102343086 A   *  2/2012
CN      102343086 A      2/2012

OTHER PUBLICATIONS

Fang L, Wang K, Liu X, Zhang L, Zhang X, Qian L, Lu J, Qian G, Ge S. A study on anti-tumor immunity induced by gene-modified melanoma B16 cells. Oncol Rep. Jun. 2008;19(6):1589-95. PMID: 18497970. (Year: 2008).*
Wang et al., Cationic liposomes as carriers for gene delivery: Physico-chemical characterization and mechanism of cell transfection, Feb. 2012, African Journal of Biotechnology 11(11) DOI:10.5897/AJB11.3019 (Year: 2012).*
Dalby B, Cates S, Harris A, Ohki EC, Tilkins ML, Price PJ, Ciccarone VC. Advanced transfection with Lipofectamine 2000 reagent: primary neurons, siRNA, and high-throughput applications. Methods. Jun. 2004;33(2):95-103. (Year: 2004).*
Yang, JP., Huang, L. Time-dependent maturation of cationic liposome-DNA complex for serum resistance. Gene Ther 5, 380-387 (1998). (Year: 1998).*
Siders WM, Vergillis K, Johnson C, Scheule RK, Kaplan JM. Tumor treatment with complexes of cationic lipid and noncoding plasmid DNA results in the induction of cytotoxic T cells and systemic tumor elimination. Mol Ther. Oct. 2002;6(4):519-27. (Year: 2002).*
Cadet et al., Oxidatively Generated Damage to Cellular DNA by UVB and UVA Radiation, Photochem Photobiol. Jan.-Feb. 2015;91(1):140-55. (Year: 2014).*

(Continued)

*Primary Examiner* — Julie Wu
*Assistant Examiner* — John J Skoko, III
(74) *Attorney, Agent, or Firm* — Caesar Rivise, PC

(57) ABSTRACT

The present invention belongs to the field of biological medicine, particularly to a novel tumor vaccine. In order to solve the problem in the art that no technical scheme is available for generating lasting and high-effective anti-tumor immune responses, the present invention provides a tumor vaccine mainly containing a complex as a main active ingredient, wherein the complex is formed by nucleic acid, especially replicable nucleic acid not expressing exogenous gene, and cationic biomaterial. The nucleic acid and the cationic biomaterial in the tumor vaccine according to the present invention have synergistic interactions on direct killing of tumor cells, and induction of the innate immune response and adaptive immune response of body against tumor. In addition, the prepared tumor vaccine has simple drug component and is easy to produce and maintain quality control. The tumor vaccine has a good prospect for application.

39 Claims, 22 Drawing Sheets

Specification includes a Sequence Listing.

(56) References Cited

OTHER PUBLICATIONS

Templeton, N., Lasic, D., Frederik, P. et al. Improved DNA: liposome complexes for increased systemic delivery and gene expression. Nat Biotechnol 15, 647-652 (1997). (Year: 1997).*
Gehrke N, Mertens C, Zillinger T, Wenzel J, Bald T, Zahn S, Tüting T, Hartmann G, Barchet W. Oxidative damage of DNA confers resistance to cytosolic nuclease TREX1 degradation and potentiates STING-dependent immune sensing. Immunity. Sep. 19, 2013; 39(3):482-95. (Year: 2013).*
Zhang XP, Yang L, Shi HS, et al., An N-, C-terminally truncated basic fibroblast growth factor and bPD (liposome-polycation-DNA) complexes elicits a protective immune response against murine colon carcinoma. Cancer Biol Ther. Aug. 1, 2010;10(3):276-81. (Year: 2010).*
Invitrogen (pcDNA™3.1(+) pcDNA™3.1(−), Catalog Nos. V790-20 and V795-20, Version K, Nov. 10, 2010) (Year: 2010).*
Translation of CN 102343086.
Xiawei Wei, et al., Cationic nanocarriers induce cell necrosis through impairment of Na+/K-ATPase and cause subsequent inflammatory response, Cell Research (2015) 1-17.
Liang, et al., Construction of a replicative anti-tumor DNA vaccine PSCK-2PCK-2PFcGB and its expression in vivo and in vitro, J South Med Univ, (2011) 937-942.
Expression vector pMVAX1(c), complete sequence, - Nucleotide—NCBI Mar. 14, 2014.

\* cited by examiner

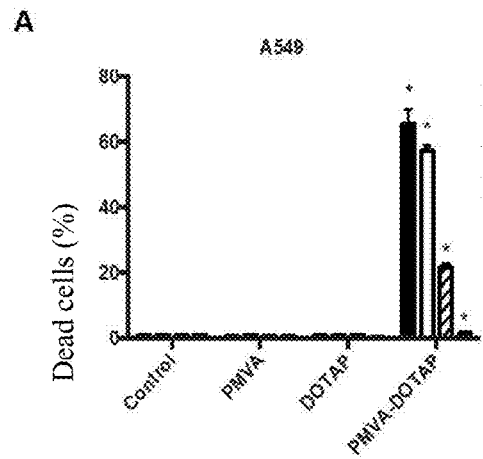
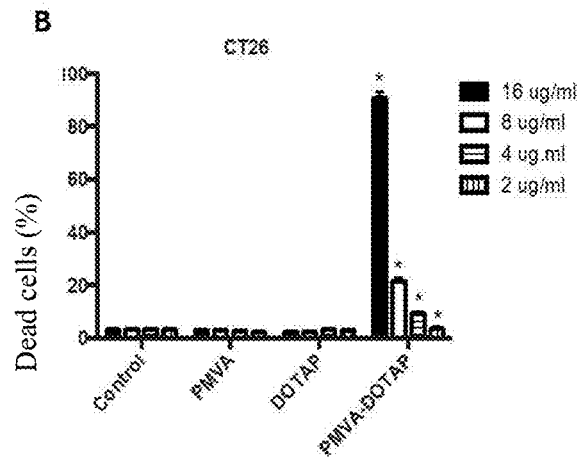
FIG. 8A  FIG. 8B
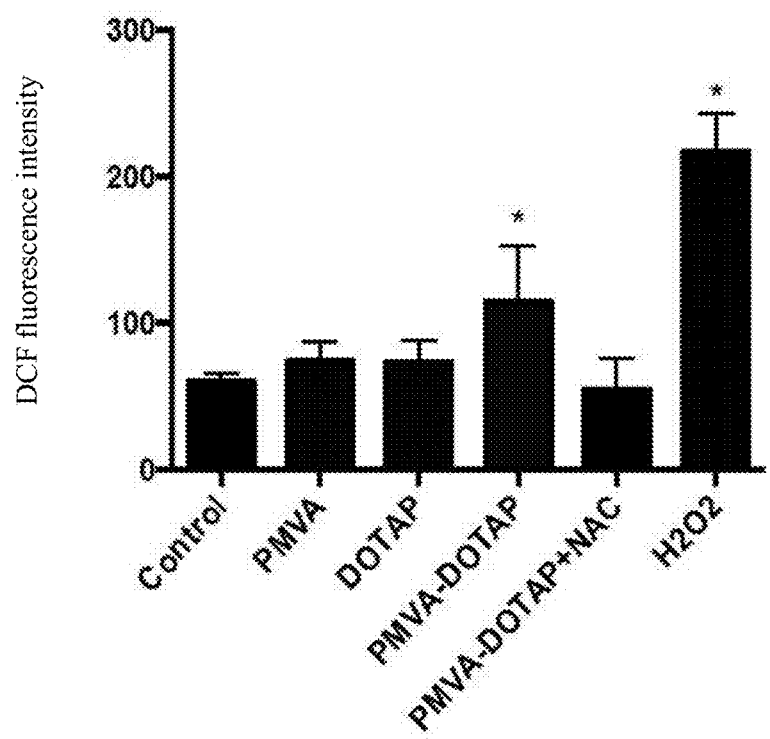
FIG. 9

TUMOR VACCINE AND USES THEREOF

CROSS-REFERENCE TO RELATED APPLICATIONS

This application is a U.S. National Phase Application of PCT/CN2018/092198, filed Jun. 21, 2018, which claims priority to CN 201710509396.6, filed Jun. 28, 2017, the contents of which applications are incorporated herein by reference in their entireties for all purposes.

FIELD OF THE INVENTION

The invention belongs to the field of biomedicine, and particularly relates to a novel tumor vaccine, a preparation method and uses thereof in treating and/or preventing tumors.

BACKGROUND OF THE INVENTION

Based on frontier sciences like modern molecular biology, immunology and cytobiology, modern biotechnology and its products are used in tumor biotherapy for tumor prevention and treatment, promoting the reconstruction of human immune cells to directly restore and improve the immune functions of human bodies by increasing the number of immune cells, enhancing the immunity of human bodies to cancer cells, and achieving the purpose of treating tumors by interfering with a series of processes such as occurrence, growth, differentiation, invasion, metastasis and recurrence of tumor cells. Tumor biotherapy has become the fourth major tumor therapy after surgery, radiotherapy and chemotherapy, mainly including tumor immunotherapy (including antibody therapy, tumor vaccine therapy, adoptive cell immunotherapy and cytokine therapy), tumor gene therapy, antiangiogenic therapy and molecular targeted therapy, etc.

Tumor vaccine therapy has always been one of hot research fields of tumor biotherapy. Its principle is to inhibit the growth, metastasis and recurrence of cancer cells by activating patients' own immune systems and inducing the bodies to produce specific cellular immune and humoral immune responses with tumor antigens, so as to control or kill tumors. Tumor vaccine therapy involves tumor cell vaccines, tumor polypeptide vaccines, genetic engineering vaccines for tumors, tumor nucleic acid vaccines and anti-idiotypic antibody vaccines, etc. Since DNA as nucleotide generally does not induce bodies to generate immune responses after entering the bodies due to no pathogenicity and low immunogenicity, "tumor DNA vaccines" currently referred to in the art generally refers to the tumor-associated antigens or tumor-specific antigens and expressed genes of immunostimulatory factors built into plasmid vectors which are injected into bodies to express the corresponding tumor antigens in host cells, so as to stimulate the bodies to generate specific and nonspecific immune responses. Tumor DNA vaccines are safe and effective, easy to prepare and purify in large quantities, and difficult to integrate into host cell genomes, so they have attracted extensive attention in tumor immunotherapy.

Although clinical studies have shown that the above tumor DNA vaccines can activate tumor patients to produce antigen-specific anti-tumor immune responses in clinical trials over time, the tumor DNA vaccines can rarely induce tumor patients to produce durable and efficient anti-tumor immune responses at present, and it is difficult to obtain durable effects of preventing or treating tumors. As a result, how to improve the immunogenicity of tumor DNA vaccines and induce tumor patient's body to produce durable and efficient anti-tumor immune responses to obtain more satisfactory effects of tumor prevention or treatment is a technical problem to be solved urgently.

SUMMARY OF THE INVENTION

Since naked DNA is not easy to enter cells directly and is easy to be degraded by nucleases in cells, DNA vaccines are low in transfection efficiency and very weak in immunogenicity while treating tumors, and are not easy to activate the body's anti-tumor immune responses. Cationic biomaterials are used as drug delivery systems. Compared with viral vectors, cationic lipids have the advantages of simple and rapid synthesis and mass production. Due to self-contained positive charges, cationic lipids are easy to form complexes with negatively charged DNA via electrostatic binding, and thus can protect DNA against degradation in vivo. The formed complexes are ingested by cells through endocytosis or phagocytosis. However, studies have shown that apoptosis occurs sometimes during gene transfection.

Cationic biomaterials can also be used as adjuvants in tumor DNA vaccines. The complexes formed by DNA and cationic biomaterials are beneficial to be phagocytized by antigen-presenting cells (APC) such as macrophages and dendritic cells (DC), thus enhancing the immunogenicity of DNA vaccines. Positive charges on the surfaces of the complexes can help prolong the residence time of the DNA vaccines at injection sites, increase antigen presentation, and prolong the time for stimulating cellular immunity in vivo. However, when used as a drug delivery system to prepare tumor DNA vaccines for treating tumors, cationic biomaterials often cause acute cell necrosis of tissue cells and initiate damage-associated molecular patterns (DAMP) after systemic administration, thus inducing a series of inflammatory responses in bodies and easily causing toxic injuries of tissues such as hepatotoxicity and pulmonary toxicity. Such factors limit the clinical application of cationic biomaterials as drug delivery systems in current tumor DNA vaccine therapy. Therefore, how to effectively utilize the advantages of cationic biomaterials to develop drug delivery systems, improve the bioavailability and targeting of drugs in vivo, and reduce the toxic side effects thereof are urgent tasks to be addressed in the development of cationic nano drug delivery systems.

According to the inventor's previous research (Cell Research (2015) 25:237-253), cationic biomaterials can bind to OBS sites on $Na^+/K^+$-ATP enzymes on tumor cell membranes, thereby resulting in an increase in $Na^+$ concentration in tumor cells, directly causing tumor cell necrosis, and releasing intracellular mitochondria and other associated antigens and reactive oxygen species (ROS). Mitochondrial DNA has abundant CpG structures, and can activate TLR9 signaling pathway, namely TLR9-MyD88 pathway, after oxidation by ROS, thus inducing innate immune responses, resulting in activation and aggregation of inflammatory cells, stimulating neutrophils to release more inflammatory factors and enhancing immune responses. Therefore, cationic nanocarriers can directly induce the necrosis of tumor cells with a new cell necrosis mechanism, namely a damage pathway through $Na^+/K^+$-ATP enzymes, which different from previously studied RIP1 or MLKL-regulated cell necrosis pathways. In addition, local injection of cationic nanocarriers can also cause release of antigens from tumor cells and activate immune responses of immune cells against tumors.

In addition, as a new theory of lysosome-initiated apoptosis, the lysosomal-mitochondrial axis theory proposed by Terman et al. suggests that under the stimulation of oxidative stress, ionizing radiation and lysosomal targeting drugs, the lysosoma membrane permeabilization increases, hydrolases in lysosomes are released into cytoplasm, directly resulting in mitochondrial damage from released phospholipase hydrolases, or indirectly resulting in mitochondrial damage from other pro-apoptotic proteins (e.g., Bid) activated by hydrolases, eventually leading to release of cytochrome c in mitochondria and activation of Casepse, thus triggering apoptosis. In addition, multiple studies have shown that tumor cells are more sensitive to lysosomal membrane stability than normal cells.

Although DNA vaccines, cationic biomaterials, and mechanisms of lysosome-initiated apoptosis have been studied, there are no reports that replicable DNA fragments (pMVA plasmids and pMVA-1 plasmids) that do not have the ability to express exogenous genes form complexes with cationic biomaterials, which have synergistic anti-tumor effects as tumor vaccines. There are also no reports that the oxidized DNA fragments form complexes with cationic biomaterials, which have stronger anti-tumor effects as tumor vaccines.

Starting from the weakness of the prior art, the present invention aims at providing a DNA/cationic biomaterial complex formed by a replicable DNA fragment which does not express an exogenous gene and a cationic biomaterial, and the complex has an anti-tumor synergistic effect. The complex may not only directly kill a tumor, but also activate the innate immune response and adaptive immune response of a body against the tumor, and may produce a long-term memory immunity. Therefore, the complex may be used as a tumor vaccine alone or used in combination with other tumor treatment methods to treat different types of tumors.

The object of the present invention is achieved by the following technical solutions: The present invention provides a tumor vaccine. Components of the tumor vaccine comprise complex formed by DNA and cationic biomaterial.

Further, the DNA in the tumor vaccine has a length of 50-10000 bp.

Preferably, the DNA in the tumor vaccine has a length of 100-6000 bp.

Wherein, the DNA in the tumor vaccine is linear DNA or circular DNA.

Further, the linear DNA in the tumor vaccine is mitochondrial DNA or mitochondrial DNA fragment.

Wherein, the circular DNA in the tumor vaccine is plasmid.

Further, the plasmid in the tumor vaccine is selected from at least one of pMVA, pMVA-1, pVAX1, pcDNA3.1, pBR322 or pUC18.

Wherein, the plasmid in the tumor vaccine is a replicable plasmid which comprises a replicon, a resistance gene and a plasmid backbone sequence but is unable to express an exogenous gene.

Wherein, the replicable plasmid which comprises a replicon, a resistance gene and a plasmid backbone sequence but is unable to express an exogenous gene is pMVA plasmid, and the nucleotide sequence thereof is expressed as SEQ ID NO. 1 or the nucleotide sequence thereof is at least 90% homologous to the sequence expressed as SEQ ID NO. 1.

Wherein, the replicable plasmid which comprises a replicon, a resistance gene and a plasmid backbone sequence but is unable to express an exogenous gene is pMVA-1 plasmid, and the nucleotide sequence thereof is expressed as SEQ ID NO. 2 or the nucleotide sequence thereof is at least 90% homologous to the sequence expressed as SEQ ID NO. 2.

The nucleotide sequence of the pMVA plasmid is expressed as SEQ ID NO: 1. The pMVA plasmid is a replicable plasmid having the most basic structural unit formed after reconstitution, comprising a kanamycin resistance gene, a pUC origin sequence and a plasmid backbone sequence (as expressed as FIG. 1). The pMVA plasmid is unable to express an exogenous gene, and is capable of replicating and screening genes in *Escherichia coli*. More importantly, the plasmid is beneficial to be oxidized in tumor cells so as to form oxidized DNA. Therefore, the plasmid has stronger anti-tumor activity and is suitable for large-scale production.

The nucleotide sequence of the pMVA-1 plasmid is expressed as SEQ ID NO: 2. The pMVA-1 plasmid is obtained by base mutation or deletion of the pMVA plasmid at a specific nucleotide site. A vector of the pMVA-1 plasmid has the efficacy of the pMVA plasmid, and the yield of the pMVA-1 plasmid is greater than that of the pMVA plasmid. Therefore, the pMVA-1 plasmid is more favorable for large-scale production and may effectively reduce the production cost.

Further, the plasmid in the tumor vaccine is loaded with other DNA.

Wherein, the other DNA in the tumor vaccine has a length of 50-3000 bp.

Preferably, the other DNA in the tumor vaccine has a length of 100-2500 bp.

Wherein, the other DNA in the tumor vaccine is mitochondrial DNA or mitochondrial DNA fragment.

Further, the mitochondrial DNA (mtDNA) in the tumor vaccine is selected from at least one of DNA fragments having the nucleotide sequences expressed as SEQ ID NO. 3, SEQ ID NO. 4 or SEQ ID NO. 5, or DNA fragments whose nucleotide sequences are at least 90% homologous to the sequences expressed as SEQ ID NO. 3, SEQ ID NO. 4 or SEQ ID NO. 5. The mtDNA or mtDNA fragment is rich in CpG motifs, and may be used as an agonist of TLR9 pathway or STING pathway to activate innate immune response against tumor.

Further, the plasmid in the tumor vaccine is preferably at least one of the pMVA plasmid carried with the mtDNA or the pMVA-1 plasmid carried with the mtDNA, for example, pMVA-2 plasmid as expressed as SEQ ID NO. 6, pMVA-3 plasmid as expressed as SEQ ID NO. 7, pMVA plasmid-4 as expressed as SEQ ID NO. 8, pMVA-5 plasmid as expressed as SEQ ID NO. 9, pMVA-6 plasmid as expressed as SEQ ID NO. 10 and pMVA-7 plasmid as expressed as SEQ ID NO. 11, or a plasmid whose nucleotide sequence is at least 90% homologous to the sequences expressed as SEQ ID NO. 6, SEQ ID NO. 7, SEQ ID NO. 8, SEQ ID NO. 9, SEQ ID NO. 10 or SEQ ID NO. 11.

The DNA in the tumor vaccine may be further selected from oxidized DNA formed by oxidation in vitro. Preferably, the oxidized DNA is an oxidized plasmid.

Wherein, the oxidation in vitro in the tumor vaccine includes, but not limited to, the use of irradiation or various oxidizing agents. The irradiation includes radiation with ultraviolet rays, X-rays, gamma rays, etc., and the oxidizing agent includes oxygen, ozone, $F_2$, $Cl_2$, $Br_2$, nitrate, chlorate, perchlorate, $HNO_3$, $KMnO_4$, $NaClO$, $CrO_3$, $H_2O_2$, $PbO_2$, $NaBiO_3$, $XeF_2$, $Ce^{4+}$, $PdCl_2$ and so on.

Wherein, the cationic biomaterial in the tumor vaccine is selected from at least one of cationic lipid material or cationic polymer.

Further, the cationic lipid material in the tumor vaccine is a cationic lipid or a complex formed by cationic lipid and helper lipid.

Wherein, the cationic lipid in the tumor vaccine is selected from at least one of 1,2-dioleoyl-3-trimethylammonium-propane (DOTAP), N-[1-(2,3-dioleyloxy) propyl]-N,N,N-trimethylammonium chloride (DOTMA), 2,3-dioleyloxy-N-[2(spermine carboxamido)ethyl]-N,N-dimethyl-1-propanaminium trifluoroacetate (DOSPA), dodecyltrimethylammonium bromide (DTAB), tetradecyltrimethylammonium bromide (TTAB), cetyltrimethylammonium bromide (CTAB) or dimethyldioctadecylammonium bromide (DDAB).

Wherein, the helper lipid in the tumor vaccine is selected from at least one of phosphatidyl ethanolamine (PE), phosphatidylcholine (PC), cholesterol (Chol) or dioleoyl phosphoethanolamine (DOPE).

Further, in the tumor vaccine, the mass ratio of the cationic lipid to the helper lipid in the complex formed thereby is 1:0.1 to 1:10.

Wherein, the cationic polymer in the tumor vaccine is selected from at least one of polyethyleneimine, polysaccharide, polyamide-amine PAMAM, or polymer containing an imidazole group.

Wherein, the polyethyleneimine in the tumor vaccine has a molecular weight of 2-30 kD.

Wherein, the polyethyleneimine in the tumor vaccine is PEI 2 kD, PEI 5 kD or PEI 25 kD.

Wherein, the polysaccharide in the tumor vaccine is selected from at least one of chitosan, carboxymethyl chitosan, trimethyl chitosan or chitosan quaternary ammonium salt.

Wherein, the polysaccharide in the tumor vaccine has a molecular weight of 30-50 kD.

The chitosan is a naturally-rich aminopolysaccharide and a derivative of chitin, with excellent biocompatibility, biodegradability and non-toxic properties.

Since the cationic polymer contains —NH2 which is unprotonated under a neutral condition, such polymer has a sponge proton effect under a lysosomal acidic condition, which ruptures lysosomal membrane, induces tumor cells to die, and promotes the release of immunogenic molecules from cancer cells, thereby enhancing the specific immune response of body against tumor.

In summary, the cationic biomaterial according to the present invention is suitable for delivery of DNA in vivo, and is particularly suitable for transfecting and transporting compressed and stable DNA into cells. Since negatively charged DNA may be combined with the cationic biomaterial by electrostatic interaction, DNA phosphate group may be fused with the cationic biomaterial to rearrange the structure after most or all of negative charges carried thereby are neutralized, resulting in DNA compression. The cationic biomaterial, on the other hand, may improve the transport of DNA in vivo, and is particularly suitable for subcutaneous or intraperitoneal injection, and improves the serum stability, uptake efficiency and release of DNA. More importantly, the cationic biomaterial according to the present invention may directly induce necrosis of tumor cells, thus releasing intracellular mitochondria, tumor-associated antigen and ROS from such cells. In addition, tumor necrosis may enhance the immunogenicity of the tumor cells, thereby activating the specific immune response of the body against the tumor. In addition, the cationic biomaterial may also support the induction and maintenance of adaptive immune response by primary or re-enhanced innate immune response, and the cationic biomaterial also has improved storage stability.

In the tumor vaccine, the mass ratio of the DNA to the cationic biomaterial in the complex formed thereby is 1:1 to 1:100.

Preferably, the mass ratio of the DNA to the cationic biomaterial in the complex formed thereby is 1:1 to 1:50.

The DNA/cationic biomaterial complex has a particle diameter of 1-2,000 nm.

Preferably, the DNA/cationic biomaterial complex has a particle diameter of 50-1000 nm.

In the tumor vaccine, the DNA/cationic biomaterial complex has a potential of 1-150 mv.

Preferably, in the tumor vaccine, the DNA/cationic biomaterial complex has a potential of 5-100 mV.

Wherein, the DNA/cationic biomaterial complex has a synergistic effect in inducing the immune response of a body against a tumor, and the performance thereof is as follows: the cationic biomaterial may promote the cell transfection rate of plasmid DNA on the one hand, and has an immunoadjuvant effect on the other hand. The cationic biomaterial may directly kill cancer cells, and may increase the $Na^+$ concentration in the tumor cells by binding to an OBS site on the $Na^+/K^+$-ATPase on tumor cell membrane, leading to tumor cell necrosis, and release of mitochondria and other related antigens and reactive oxygen species (ROS) from the cells. The mtDNA in tumor cells is rich in unmethylated CpG motifs which may activate an STING or TLR9 signaling pathway after oxidation of the ROS, thereby inducing innate immune response, activating and aggregating inflammatory cells, and stimulating release of more inflammatory factors from neutrophile, such as IL-6, IL-12, IFN-γ and TNF-α. In a third aspect, the cationic biomaterial induces necrosis of tumor cells, thus releasing tumor antigen from such cells. The released tumor antigen is processed in DC cell and presented to the surface thereof, thus further activating and aggregating the specific tumoricidal activity of $CD8^+$ T cells and $CD4^+$ T cells.

The DNA/cationic biomaterial complex, after entering the tumor cells by virtue of endocytosis, may cause a significant increase of the ROS in the tumor cells. After the DNA/cationic biomaterial complex is oxidized by the ROS, the DNA therein, including the mtDNA or the plasmid, may form oxidized DNA. The oxidized DNA is phagocytized by lysosomes, causing a significant change in the acidic gradient of the lysosome, that is, change in the permeability of the lysosomal membrane, which leads to lysosomal rupture and release of a large amount of lysosomal proteolytic enzymes (such as cathepsin). Hydrolytic enzymes are released into the cytoplasm, causing a decrease in mitochondrial membrane potential of mitochondria in tumor cells, leading to mitochondria damage, and further activating caspase, thereby inducing tumor cell death, including tumor cell apoptosis and tumor cell necrosis.

Hence, the DNA/cationic biomaterial complex plays a significant role in coordinate induction of tumor cell death, while the cationic biomaterial or DNA used alone does not have such a significant effect.

The DNA/cationic biomaterial complex may also synergistically promote DC cells maturation, and the oxidized DNA binds to the cGAS in the cytoplasm of DC cells so as to form cGMP (cyclic GMP-AMP, cyclic guanosine monophosphate-adenosine monophosphate). The cGMP may effectively activate STING (stimulator of interferon genes) protein, induce DC cells to release IFN-β and other inflammatory factors (such as IL-1β and IL-6), thereby triggering the innate immune response of the STING signaling pathway (cGAS-2'3'cGAMP-STING-TBK-IRF3) against tumor. While synergistically promoting DC cells maturation, the DNA/cationic biomaterial complex alters the tumor microenvironment and induces the specific tumor-killing activity of the CD8+ T cells.

Furthermore, the DNA may also be selected from oxidized DNA formed by oxidation in vitro, such as oxidized plasmid. The oxidized DNA may form a complex with the cationic biomaterial as a tumor vaccine which has a stronger synergistic anti-tumor effect than the DNA/cationic biomaterial complex.

The oxidation in vitro may be carried out by means of radiation irradiation or treatment with oxidizing agents. The radiation irradiation may be carried out with rays which may oxidize DNA, including ultraviolet rays, gamma rays and X-rays. There are many types of oxidizing agents for processing DNA, such as oxygen, ozone, $F_2$, $Cl_2$, $Br_2$, nitrate, chlorate, perchlorate, $HNO_3$, $KMnO_4$, $NaClO$, $CrO_3$, $H_2O_2$, $PbO_2$, $NaBiO_3$, $XeF_2$, $Ce^{4+}$ and $PdCl_2$ that may be used for oxidizing the DNA in vitro.

The present invention also provides a pharmaceutical composition, comprising the tumor vaccine and a pharmaceutically acceptable excipient or auxiliary component.

Wherein, the excipient or auxiliary component in the pharmaceutical composition is at least one of a diluent, an excipient, a filler, a binder, a wetting agent, a disintegrant, an absorption enhancer, a surfactant, a protective agent, an adsorption carrier or a lubricant.

The present invention also provides a method for preparing the tumor vaccine, comprising the steps of: (1) preparing DNA and cationic biomaterial; and (2) mixing the DNA with the cationic biomaterial in Step (1), and allowing the mixture to stand so as to obtain DNA/cationic biomaterial complex.

The preparation of the DNA in the tumor vaccine comprises a method for constructing plasmid vector or a method for constructing plasmid loaded with other DNA.

Wherein, the method for constructing plasmid vector in the tumor vaccine comprises a method for constructing plasmid vector of pMVA or pMVA-1.

The method for constructing the plasmid vector of pMVA comprises the following steps: synthesizing a 1978 bp sequence, including pUC origin, kanamycin genes and two plasmid backbone sequences, by means of whole-gene synthesis, and then ligating and cyclizing to obtain the plasmid vector of pMVA, the nucleotide sequence of the plasmid vector of pMVA being expressed as SEQ ID NO. 1.

The method for constructing the plasmid vector of pMVA-1 comprises the following steps:

carrying out site-directed mutagenesis or deletion on a plurality of nucleotide sites of the vector of pMVA on the basis of the method for constructing the plasmid vector of pMVA, so as to obtain pMVA-1 plasmid optimized by mutation, the nucleotide sequence of the plasmid vector of pMVA-1 being expressed as SEQ ID NO. 2.

Wherein, the method for constructing the other DNA plasmid in the tumor vaccine comprises loading the mtDNA fragment onto pMVA plasmid vector to prepare pMVA-2, pMVA-3, and pMVA-4.

Wherein, the method for constructing pMVA-2 plasmid comprises the following steps: carrying out whole-gene synthesis on the nucleotide sequence expressed as SEQ ID NO. 3 together with the linear sequence before cyclization of pMVA, and then ligating and cyclizing to obtain pMVA-2 plasmid, the nucleotide sequence of pMVA-2 plasmid being expressed as SEQ ID NO. 6, and the nucleotide sequence at sites 33-152 being expressed as SEQ ID NO. 3.

The method for constructing pMVA-3 plasmid comprises the following steps:

carrying out whole-gene synthesis on the nucleotide sequence expressed as SEQ ID NO. 4 together with the linear sequence before cyclization of pMVA, and then ligating and cyclizing to obtain pMVA-3 plasmid, the nucleotide sequence of pMVA-3 plasmid being expressed as SEQ ID NO. 7, wherein the nucleotide sequence at sites 33-632 being expressed as SEQ ID NO. 4.

The method for constructing pMVA-4 plasmid comprises the following steps:

carrying out whole-gene synthesis on the nucleotide sequence expressed as SEQ ID NO. 5 together with the linear sequence before cyclization of pMVA, and then ligating and cyclizing to obtain pMVA-4 plasmid, the nucleotide sequence of the MVA-4 plasmid being expressed as SEQ ID NO. 8, wherein the nucleotide sequence at sites 33-2032 being expressed as SEQ ID NO. 5.

Wherein, the method for constructing plasmid carried with other DNA in the tumor vaccine comprises loading mtDNA onto the plasmid vector of pMVA-1 so as to prepare plasmids pMVA-5, pMVA-6, and pMVA-7.

Wherein, the method for constructing pMVA-5 plasmid comprises the following steps:

carrying out whole-gene synthesis on the nucleotide sequence 1 of mtDNA fragment expressed as SEQ ID NO. 3 together with the linear sequence before cyclization of the pMVA-1, and then ligating and cyclizing to obtain pMVA-5 plasmid, the nucleotide sequence of pMVA-5 plasmid being expressed as SEQ ID NO. 9, wherein the nucleotide sequence at sites 33-152 being the nucleotide sequence expressed as inserted SEQ ID NO. 3.

The method for constructing pMVA-6 plasmid comprises the following steps:

carrying out whole-gene synthesis on the nucleotide sequence 2 of mtDNA fragment expressed as SEQ ID NO. 4 together with the linear sequence before cyclization of pMVA-1, and then ligating and cyclizing to obtain pMVA-6 plasmid, the nucleotide sequence of pMVA-6 plasmid being expressed as SEQ ID NO. 10, wherein the nucleotide sequence at sites 33-632 being the nucleotide sequence expressed as inserted SEQ ID NO. 4.

The method for constructing pMVA-7 plasmid comprises the following steps:

carrying out whole-gene synthesis on the nucleotide sequence 3 of mtDNA fragment expressed as SEQ ID NO. 5 together with the linear sequence before cyclization of the pMVA-1, and then ligating and cyclizing to obtain pMVA-7 plasmid, the nucleotide sequence of pMVA-7 plasmid being expressed as SEQ ID NO. 11, wherein the nucleotide sequence at sites 33-2032 being the nucleotide sequence expressed as inserted SEQ ID NO. 5.

The preparation of the cationic biomaterial in the tumor vaccine comprises a method for preparing cationic lipid, or a method for preparing cationic lipid and helper lipid as a complex, the method comprising the steps of:

(1) mixing pyrogen-free cationic lipid or pyrogen-free auxiliary lipid, adding anhydrous ethanol, heating, and stirring to dissolve;

(2) carrying out rotary evaporation on the mixed solution in Step (1) to ⅓ of the volume of the solution, and adding water to a constant volume;

(3) allowing the solution obtained in Step (2) to pass through a high-pressure homogenizer and an extruder, so as to obtain the cationic lipid or the complex formed by the cationic lipid and the helper lipid.

In Step (1), the mass ratio of the cationic lipid to the helper lipid is 1:0.1 to 1:10; the cationic lipid is preferably DOTAP, and the auxiliary lipid is preferably cholesterol; and the heating temperature is 50° C.

The rotary evaporation temperature in Step (2) is 30-60° C., preferably 40° C., and the vacuum pressure is 0.08-0.1 MPa, preferably 0.09 MPa;

In Step (3), the pressure of the high-pressure homogenizer is 700-800 bar, and the times thereof is 3-10; the temperature of the extruder is 50° C., the extrusion film is 100 nm, and the thereof is 1-2; the particle diameter of the obtained cationic lipid or the complex formed by the cationic lipid and the auxiliary lipid is 80-150 nm and PDI of less than 0.3.

The preparation of the cationic biomaterial in the tumor vaccine comprises a preparation method for PEI: dissolving PEI (25 kD) in water.

The preparation of the cationic biomaterial in the tumor vaccine or in the pharmaceutical composition comprises a preparation method for chitosan: dissolving chitosan (30-50 kD) with medium molecular weight in water or dilute acid.

The present invention also provides a method for preparing the DNA/cationic biomaterial complex, and further provides a method for preparing the DNA/cationic biomaterial complex as a vaccine for treating tumor, the method comprising the steps of:

mixing the prepared cationic biomaterial with DNA under a sterile condition and allowing the mixture to stand for 0.5-1 h so as to form the DNA/cationic biomaterial complex;

the prepared DNA/cationic biomaterial complex has an average particle diameter of less than 500 nm and a potential of less than 100 mV, which facilitates transfection of the complex into tumor cells. In addition, the DNA/cationic biomaterial complex may synergistically induce the tumor cells to have oxidative stress reaction and directly play an anti-tumor effect by means of lysosomal pathway, and synergistically enhance the anti-tumor activity of the body's immune response.

The present invention also provides a method for preparing the pharmaceutical composition, comprising the steps of: (1) preparing DNA and cationic biomaterial; (2) mixing the DNA with the cationic biomaterial in Step (1), and adding pharmaceutically acceptable excipient or ancillary ingredients before and/or during and/or after mixing of the DNA and the cationic biomaterial so as to prepare the pharmaceutical composition.

Wherein, the excipient or auxiliary component is at least one of a diluent, an excipient, a filler, a binder, a wetting agent, a disintegrant, an absorption enhancer, a surfactant, a protective agent, an adsorption carrier or a lubricant.

The present invention also provides a medical kit, comprising the tumor vaccine or the pharmaceutical composition, and at least one other drug for treating tumor.

Wherein, the other drug for treating tumor in the medical kit is selected from at least one of a chemotherapeutic drug or an immune response modifier.

Wherein, the immune response modifier in the medical kit is at least one of a cytokine, a class II HLA protein-binding accessory molecule, a CD40 agonist, a checkpoint receptor antagonist, a B7 costimulatory molecule, a FLt3 agonist or a CD40L agonist.

The present invention also provides an antitumor drug, comprising the tumor vaccine or the pharmaceutical composition and tumor antigen.

Wherein, the tumor antigen is selected from at least one of a tumor-associated antigen, an apoptotic tumor cell or a necrotic tumor cell.

Meanwhile, the present invention also provides a use of the tumor vaccine or the pharmaceutical composition in the preparing of a drug for treating and/or preventing tumor.

Wherein, the tumor is selected from cervical cancer, ovarian cancer, breast cancer, lung cancer, nasopharyngeal cancer, gastric cancer, pancreatic cancer, esophageal cancer, colon cancer, rectal cancer, liver cancer, prostate cancer, kidney cancer, bladder cancer, skin cancer, sarcoma or lymphoma.

Meanwhile, the present invention also provides a use of the drug combination of the tumor vaccine or the pharmaceutical composition together with at least one other drug for treating tumor in the preparation of a drug for treating or preventing tumor.

Wherein, the other drug for treating tumor in the use is selected from at least one of a chemotherapeutic drug or an immune response modifier.

Wherein, the immune response modifier is at least one of a cytokine, a class II HLA protein-binding accessory molecule, a CD40 agonist, a checkpoint receptor antagonist, a B7 costimulatory molecule, a FLt3 agonist or a CD40L agonist In addition, the present invention also provides a method for treating tumor. The method comprises administering a therapeutically effective amount of at least one of the tumor vaccine, the pharmaceutical composition, the kit or the antitumor drug to a mammal having tumor.

Wherein, the mammal in the method is a mouse, a dog, a monkey or a human being.

Wherein, the tumor in the method is selected from cervical cancer, ovarian cancer, breast cancer, lung cancer, nasopharyngeal cancer, gastric cancer, pancreatic cancer, esophageal cancer, colon cancer, rectal cancer, liver cancer, prostate cancer, kidney cancer, bladder cancer, skin cancer, sarcoma or lymphoma.

Wherein, injection is used to administer the tumor vaccine, the pharmaceutical composition, the therapeutic kit or the antitumor drug in the method.

Wherein, the injection in the method is at least one of subcutaneous single-point injection, subcutaneous multipoint injection, intravenous injection, peritumoral injection, intratumoral injection, intrathoracic injection, intraperitoneal injection, intrathecal injection, lymphatic or perilymphatic injection or intramuscular injections. The injection may be used alone depending on the specific situation, and may be used in combination if necessary.

Wherein, the use of the tumor vaccine or the pharmaceutical composition for treating a mammal having tumor comprises activating anti-tumor immune response, comprising innate immune response and adaptive immune response, in a tumor-bearing animal, thereby achieving the purpose of inhibiting tumor growth. In addition, memory immune cells in the tumor-bearing animal treated by the tumor vaccine or the pharmaceutical composition may effectively inhibit tumor cell growth, metastasis and recurrence, and break the immune tolerance of the animal's body when such cells are attacked by tumor cells again, thereby achieving a long-term anti-tumor immunotherapy effect. In the method for treating a tumor with the tumor vaccine or the pharmaceutical composition, the effective dose of the administered DNA is 1-50 μg/kg, and the mass ratio of the DNA to the cationic biomaterial is 1:1 to 1:100, preferably 1:1 to 1:50.

Wherein, at least one other drug for treating tumor in the method is administered in the process of treating tumor.

Wherein, the other drug for treating tumor in the method is tumor antigen.

Wherein, the tumor antigen in the method is selected from at least one of a tumor-associated antigen, an apoptotic tumor cell or a necrotic tumor cell.

The tumor cells include cervical cancer cells, ovarian cancer cells, breast cancer cells, colon cancer cells, sarcoma cells, nasopharyngeal carcinoma cells, lung cancer cells, gastric cancer cells, pancreatic cancer cells, esophageal cancer cells, liver cancer cells, prostate cells, kidney cancer cells, bladder cancer cells or skin cancer cells.

Wherein, radiotherapy may also be used in the treatment of tumor.

The beneficial effects of the present invention are as follows:

1. The present invention reconstituted a plasmid which was unable to express exogenous gene but was capable of replicating and screening genes in *Escherichia coli*, such as the vector of pMVA plasmid and the plasmid (pMVA-2, pMVA-3 and pMVA-4) carried with mtDNA fragment, and the vector of pMVA-1 plasmid and the plasmid (pMVA-5, pMVA-6 and pMVA-7) carried with mtDNA fragment. More importantly, these plasmids were more favorable for oxidation in tumor cells to form oxidized DNA which had stronger anti-tumor activity and was more convenient for large-scale production.

2. With a DNA (such as pMVA)/cationic biomaterial complex as a main active ingredient, the tumor vaccine may directly play an anti-tumor synergistic effect by means of lysosomal rupture.

The present invention creatively found that after the DNA (such as pMVA)/cationic biomaterial complex was endocytosed into cytoplasm by tumor cells, the tumor cells produced a large amount of ROS, and the oxidized DNA formed by oxidizing the complex with the ROS promoted lysosoma membrane permeabilization (Lysosoma membrane permeabilization, LMP), so that cathepsin was released from lysosomal cavity to the cytosol, which triggered a series of cascade recaction that caused lysosomal instability. In addition, the LMP further caused the tumor cells to suffer from mitochondrial outer membrane permeabilization (MOMP), and cytochrome c was released into the cytoplasm of the tumor cells, thereby activating a classical caspase apoptosis pathway, and ultimately causing the tumor cells to die.

3. With the DNA (such as pMVA)/cationic biomaterial complex as a main active ingredient, the tumor vaccine also has a synergistic effect of activating anti-tumor immune response:

The present invention also creatively found that in vitro cell activity assay and in vivo pharmacodynamic experiment proved that the DNA (such as pMVA)/cationic biomaterial complex formed by mixing the cationic biomaterial and DNA (such as pMVA) had a synergistic effect for anti-tumor immune response compared with the separate use of the cationic biomaterial and plasmid DNA:

a. In vitro experiments showed that the transfection of the DNA (such as pMVA)/cationic biomaterial complex into tumor cells caused a significant increase in ROS in tumor cells, and the oxidized DNA formed by oxidizing the DNA/cationic biomaterial complex with ROS activated STING pathway, stimulated DC cells maturation and secreted IFN-β and IL-1β, thereby initiating innate immune response against tumor.

b. In vivo experiments showed that after injection of the DNA (such as pMVA)/cationic biomaterial complex, tumor cells became necrotic, DNA was oxidized, lysosomal lysis occurred in tumor cells, natural immune cells (that is neutrophils) at the tumor sites increased, and immunosuppressive factor and angiogenesis factor expressions reduced. At the same time, it was detected that DC cells around the tumor tissue phagocytized tumor antigen and oxidized plasmid DNA, and a large number of $CD4^+$ lymphocytes and $CD8^+$ lymphocytes infiltrated, indicating that the complex activated the body's adaptive immune response.

c. The DNA (such as pMVA)/cationic biomaterial complex was used as a main active ingredient to prepare a tumor vaccine for treating a model mouse with tumor, and the complex had a long-term anti-tumor immunity when the tumor-disappearing mice was subjected to a second attack by tumor cells Therefore, the DNA/cationic biomaterial complex according to the present invention has a synergistic effect on directly inducing tumor cells necrosis, and synergistically causes release of autoantigen and oxidized DNA from tumor cells, initiation of STING pathway and activation of innate immune response caused by inflammatory cells. Furthermore, the complex may promote the maturation of DC cells, induce the body to produce adaptive immune response against tumor.

4. The tumor vaccine with the DNA (such as pMVA)/cationic biomaterial complex as a main active ingredient has the advantages of simple ingredients and easy quality control: The tumor vaccine involved in the technical solution is composed of cationic biological material and DNA. The tumor vaccine has simple ingredients, is easy to be subject to quality control, and is suitable for large-scale production, which significantly reduces the production cost.

5. The tumor vaccine with the DNA (such as pMVA)/cationic biomaterial complex as a main active ingredient may be used as an adjuvant of tumor cell antigen, and thus further enhances the immune response of tumor cell antigen, and may be applied to different types of tumor treatment.

6. Experiments show that the tumor vaccine with the DNA (such as pMVA)/cationic biomaterial complex as a main active ingredient may be applied to the treatment and combined treatment of various tumors, and has a broad application prospect.

The vaccine according to the technical solution may be used for treating various tumors including cervical cancer, ovarian cancer, breast cancer, lung cancer, nasopharyngeal cancer, colon cancer, lymphoma and sarcoma, and may also be combined with radiotherapy and/or chemotherapy, or with immunosuppressive agents for treatment of tumors. The vaccine has a wide range of indications, flexible treatment methods and a broad application prospect.

BRIEF DESCRIPTION OF DRAWINGS

FIG. 1A: pMVA plasmid construction map, including kanamycin resistance genes (No. 205-999 bp), pUC origin sequences (No. 1309-1972 bp) and plasmid skeleton sequences (No. 1-204 bp, No. 1000-1308 bp and No. 1973-1978 bp), totaling 1978 bp (as shown in SEQ ID NO. 1).

FIG. 1B: pMVA-1 plasmid construction map, including kanamycin resistance genes (No. 205-999 bp), pUC origin sequences (No. 1308-1971 bp) and plasmid skeleton sequences (No. 1-204 bp, No. 1000-1307 bp and No. 1972-1977 bp), totaling 1977 bp (as shown in SEQ ID NO. 2).

FIG. 7A shows a fluorescence micrograph of A549 apoptosis co-induced by pMVA-1/DOTAP complex, and FIG. 7B shows a fluorescence micrograph of CT26 apoptosis co-induced by pMVA-1/DOTAP complex. After treatment with PMVA-1/DOTAP complexes for 24 h respectively, both A549 cells and CT26 cells showed significant PI positive and AnnexinV positive results, while no significant PI positive and AnnexinV positive cells were found in control groups.

FIGS. 8A and 8B show the number of apoptotic cells in tumor cells treated with different samples determined by flow cytometry. FIG. 8A shows a statistical chart of apoptotic A549 cells in each group determined by flow cytometry. FIG. 8B shows a statistical chart of apoptotic CT26 cells in each group determined by flow cytometry. All results were expressed as mean relative expression ±SD, *p<0.05, involving a blank control group (Control), pMVA plasmid control group (PMVA), DOTAP cationic liposome group (DOTAP), and pMVA-1/DOTAP complex treatment group (PMVA-DOTAP).

FIG. 9 shows a statistical chart of ROS level in A549 cells determined by flow cytometry. Wherein, for a Cont. blank control group: only medium was added to A549 cells; for the PMVA control group: pMVA-1 plasmids were added to A549 cells; for the DOTAP control group: for the DOTAP was added to A549 cells; for the PMVA-DOTAP treatment group: for the pMVA-1/DOTAP complex was added to A549 cells; for the NAC negative control group: pretreatment with 5 mM NAC was carried out before the pMVA-1/DOTAP complex work; and for the H2O2 positive control group: 200 μM of H2O2 was added to A549 cells. All results were expressed as mean relative expression ±SD, *P<0.05.

FIG. 14A shows increased lysosoma membrane permeabilization of A549 cells determined by FITC-Dextran intracellular localization method; FIG. 14B shows the release of lysosomal hydrolases of A549 cells into cytoplasm determined by Cathepsin B intracellular localization method. For the blank control group: only medium was added to A549 cells; for the PMVA control group: pMVA-1 plasmids were added to A549 cells; for the DOTAP control group: DOTAP was added to A549 cells; for the PMVA-DOTAP treatment group: pMVA-1/DOTAP complex was added to A549 cells.

FIG. 15A shows the percentage of A549 cells with mitochondrial membrane potential depolarization determined by flow cytometry; FIG. 15B shows the percentage of CT26 cells with mitochondrial membrane potential depolarization determined by flow cytometry. For the blank control group: only medium was added to A549 cells; for the PMVA control group: pMVA-1 plasmids were added to A549 cells; DOTAP control group: DOTAP was added to A549 cells; and for the PMVA-DOTAP treatment group: pMVA-1/DOTAP complex was added to A549 cells. All results were expressed as mean relative expression ±SD, *P<0.05.

FIG. 18A shows the percentage of BMDC secreting IFN-β; FIG. 18B shows the percentage of BMDC secreting IL-1β. All results were expressed as mean percentage ±SD, *P<0.05. For the control group: only medium was added to BMDC cells, for the Tumor group: CT26 cells were added to BMDC cells, for the Tumor+PMVA group: CT26 cells treated with pMVA-1 plasmid vector were added to BMDC cells, for the Tumor+DOTAP group: CT26 cells treated with DOTAP cationic lipid were added to BMDC cells, and for the Tumor+PMVA-DOTAP group: CT26 cells treated with pMVA-1/DOTAP complex were added to BMDC cells.

FIG. 19A shows the weight of nude mice in pMVA-1/DOTAP complex group was significantly lower than that in other treatment groups; FIG. 19B shows the amount of ascites in nude mice in pMVA-1/DOTAP complex group was significantly less than that in other groups; FIG. 19C shows the number of knots in nude mice in pMVA-1/DOTAP complex group was significantly lower than that in other groups; and FIG. 19D shows the tumor weight of nude mice in pMVA-1/DOTAP complex group was significantly lower than that of other groups. **p<0.01.

FIG. 21A shows the amount of ascites in mice in DNA/DOTAP complex group was significantly less than that in other groups; FIG. 21B shows the tumor weight of mice in DNA/DOTAP complex group was significantly lower than that in other groups; and FIG. 21C shows the number of cancer cells in ascites of mice in DNA/DOTAP complex group was significantly lower than that in other groups. **p<0.01.

FIG. 22A shows the number of mice that died naturally from the plasmid DNA/DOTAP complex in the treatment group was significantly lower than that in other control groups (P<0.01 or P<0.05); FIG. 22B shows the tumor weight of mice in pMVA-3/DOTAP treatment group was significantly lower than that in other groups; FIG. 22C shows the amount of ascites in mice in pMVA-3/DOTAP treatment group was significantly less than that in other groups; FIG. 22D shows the number of cancer cells in ascites of mice in pMVA-3/DOTAP treatment group was significantly lower than that in other groups; and FIG. 22E shows the number of tumor nodules in mice in pMVA-3/DOTAP treatment group was significantly lower than that in other groups. **P<0.01, *P<0.05.

FIG. 25A shows there was no significant difference in weight of mice between pMVA-1/DOTAP group and normal group. FIG. 25B shows the amount of ascites of mice in pMVA-1/DOTAP group was significantly less than that in negative control group, pMVA-1 group and DOTAP group. FIG. 25C shows the survival time of mice in pMVA-1/DOTAP group was significantly longer than that in negative control group, pMVA-1 group and DOTAP group. FIG. 25D shows the tumor weight of mice in pMVA-1/DOTAP group was significantly lower than that in negative control group, pMVA-1 group and DOTAP group. *p<0.05.

FIG. 26A shows that after the mice intraperitoneally inoculated with CT26 cells for the first time and treated with pMVA-1/DOTAP complex were attacked by CT26 cells again (DOTAP+2 subcutaneously inoculated CT26 group), the tumor volume was significantly reduced compared with mice neither intraperitoneally inoculated with CT26 cells nor treated with pMVA-1/DOTAP complex, but attacked by CT26 cells (subcutaneously inoculated CT26 control group). FIG. 26B shows that after the mice intraperitoneally inoculated with CT26 cells for the first time and treated with pMVA-1/DOTAP complex were attacked by 4T1 cells (DOTAP+2 subcutaneously inoculated 4T1 group), the tumor volume was significantly reduced compared with mice neither intraperitoneally inoculated with CT26 cells nor treated with pMVA-1/DOTAP complex, but attacked by 4T1 cells (subcutaneously inoculated 4T1 control group).

INTERPRETATION OF TECHNICAL TERMS

Figure 1A:
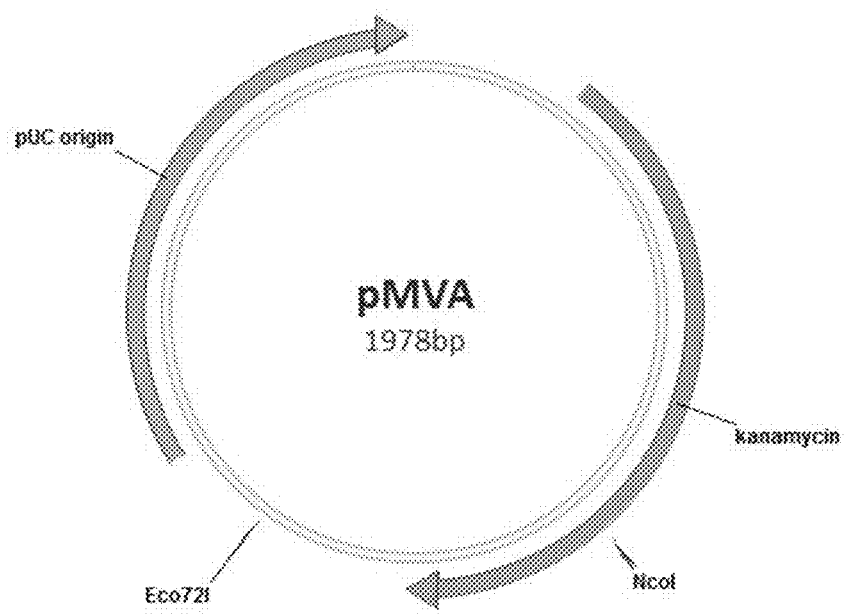
FIGS. 1A and 1B show plasmid vector construction maps.

1. Mitochondrial DNA (mtDNA): closed-loop double-stranded DNA molecules with about thousands of copies in a single cell. An mtDNA contains 37 genes, encoding 13 respiratory chain polypeptides, 22 tRNAs and 2 rRNAs, and a non-coding region "D-loop" containing gene replication and transcription regulatory sequences.

2. Lysosoma membrane permeabilization (LMP):

Although how lysosoma membrane permeabilization occurs is still controversial, LMP inducers include ROS, lipids and nanoparticles.

(1) ROS:

Under high-level oxidative stress, lysosome cannot degrade hydrogen peroxide due to absence of catalase or glutathione peroxidase, and a large amount of hydrogen peroxide is dispersed on lysosome membrane, which induces abundant divalent iron ions in the lysosome to catalyze hydrogen peroxide into hydroxyl radicals, thus triggering LMP.

(2) Lipids:

As some lipids and lipid metabolites are lysosomal, LMP can be induced.

(3) Nanoparticles: Nanoparticles can aggregate in lysosome, destroy lysosome membrane, and induce apoptosis through LMP pathway.

3. Cell Death

In normal tissues, "normal" cell death occurs frequently, which is necessary to maintain tissue functions and morphology. The ways of cell death usually involve necrosis, apoptosis and programmed cell death (PCD).

Apoptosis is the most common and well-known form of PCD, which is generally performed by activated caspases, an intracellular cysteine protease. Therefore, apoptosis can be divided into caspases-dependent and caspases-independent in terms of the initiation mechanism. Typical morphological changes of apoptotic cells include chromatin condensation, nuclear fragmentation, DNA laddering, blebbing and cytoplasmic fragmentation (apoptosis bodies). Cell membrane is not destroyed during apoptosis. Degraded cell components are encapsulated to form apoptotic bodies which are finally removed by phagocytes or lysosomes of neighboring cells through heterophagocytosis. Therefore, there is no inflammatory response around dead cells during apoptosis.

Necrosis is a phenomenon in which cells are affected by chemical factors (e.g., strong acid, strong alkali and toxic substances), physical factors (e.g., heat and radiation) and biological factors (e.g., pathogens), resulting in cell death. Morphological changes of necrotic cells are mainly caused by two pathological processes: enzymatic digestion and protein denaturation. In the early phase of necrosis, mitochondria and endoplasmic reticulum in cytoplasm swell and disintegrate, structural lipid droplets become free and vacuolated, protein particles increase, and nuclei shrink or break. With the denaturation, coagulation or fragmentation of intracellular proteins and the degradation of basophilic nucleoprotein, the cytoplasm is strongly eosinophilic. Subsequently, necrotic cells dissolve, resulting in complete disappearance of cellular structure. Finally, cell membranes and organelles rupture, DNA degrades and cell contents flow out, resulting in inflammatory responses of surrounding tissues. Residual fragments of necrotic cells can be phagocytized by macrophages or induce activation and maturation of DC cells.

4. Sting Signaling Pathway

STING (stimulator of IFN genes), also known as ERIS/MYPS/MITA, is a multifunctional adaptor protein encoded by TMEM173 genes. STING signaling pathway (cGAS-2'3'cGAMP-STING-TBK1-IRF3) is a key pathway for immune system to recognize cytoplasmic double-stranded DNA from abnormal sources and develop innate immunity. STING signaling pathway plays a key role in the body's spontaneous anti-tumor immune responses and radiotherapy-induced anti-tumor immune responses. Tumor-derived double-stranded DNA can also be ingested by DC in tumor microenvironment, activating cGAS to further catalyze ATP and GTP to synthesize 2'3'cGAMP that combines with STING to change the conformation of STING protein; the activated STING recruits TBK1, IKK, T3K1 and IKK to interact with STING and then are phosphorylated. The phosphorylated TBK1 recruits IRF3, the phosphorylated IKK recruits NF-κβ, then IRF3 and NF-κβ enter nuclei as important transcription factors after phosphorylated to regulate the expression of downstream genes and promote the secretion of type I interferon and Th1 cytokines (e.g., INF-γ). Meanwhile, the activation of STING signaling pathway can promote the maturation and activation of APC (e.g., $CD8\alpha^+/CD103^+DC$), promote APC to present tumor-associated antigens, and initiate $CD8^+T$ cell specific anti-tumor immune responses.

5. Innate immunity: also known as nonspecific immunity, refers to an innate immune defense function gradually formed in the process of phylogenesis and evolution, which forms the body's first line of defense against invasion of pathogens. Innate immunity can be inherited stably with extensive immunization but no specificity. An innate immune system can develop immune effects upon first contact with antigens, but has no immune memory.

For example, innate immune system is activated by the stimulation of microorganisms and products thereof. Toll-like receptors (TLRs) in immune cells such as macrophages, DC cells and neutrophils can recognize pathogen associated molecular pattern (PAMP) unique to the microorganisms, activate excitatory innate immunity response, secrete inflammatory cytokines (e.g., IL-12), and mediate inflammatory response.

Pattern-recognition receptor (PRR) expressed by innate immune cells is activated by recognizing different PAMAs and expresses different cytokines, thus inducing naive T cells to differentiate into different T cells and determining the type of adaptive immune responses. Therefore, innate immune responses can regulate or affect the type and intensity of adaptive immune responses, and the maintenance of adaptive immune responses and the play of its effect must also be assisted and participated in by innate immunity.

6. CpG motif: also known as immunostimulatory sequences (ISS), refers to a type of sequences with non-methylated cytosine-phosphate-guanine (CpG) as the core. As a natural ligand of TLR9, the CpG motif is a powerful non-specific immunostimulatory DNA sequence that can activate a variety of immune cells. DNA containing CpG motifs can be endocytosed by innate immune cells and recognized by intracellular TLR9, activating MyD88, TRAF6 and downstream NF-kB and MAPK pathways, resulting in a variety of transcription factors, and inducing the expression of Th1-type cytokines such as TNF-α, IL-6, IL-12 and IFN-γ, thus promoting the differentiation of naive T cells into Th1 cells. IFN-γ secreted by the Th1 cells further induces the activation of NK cells and macrophages, and promotes the division, proliferation and antibody production of B lymphocytes, thus comprehensively enhancing the cellular immunity and humoral immunity of hosts.

mtDNA in eukaryocytes is derived from the circular genomes of bacteria and also contains a large amount of unmethylated CpG motifs, which can act as PAMP on PRRs. In the case of mitochondrial dysfunction such as oxidative stress, a large amount of reactive oxygen species (ROS) are produced. mtDNA is released from mitochondria into cytoplasm as a stimulus to activate TLR9 signaling pathway, and induce neutrophil P38 MAPK pathway to produce inflammatory cytokines (e.g., IL-12) and chemokines, thus triggering adaptive immune responses, inducing naive T cells to differentiate into Th1 cells, and releasing a large amount of IFN-γ.

7. Adaptive immune response: also known as specific immune response, refers to a process in which specific T and B cells in vivo are activated, proliferated and differentiated into effector cells after being stimulated by antigens to induce a series of biological effects. The adaptive immune response is characterized by specificity, memory and tolerance.

The first phase of adaptive immune response is antigen recognition. After being ingested, processed and treated by antigen-presenting cells, antigen forms MHC complex with MHC molecules on antigen presenting cells and is specifically recognized by naive T cell or naive B cell surface receptors (TCR or BCR). Antigen-presenting cells include DC cells, macrophages and neutrophils.

The second phase is a proliferation and differentiation phase of naive T cells or naive B cells. T/B cells specifically recognize antigens and generate a first signal for activation. The T/B cells interact with a variety of adhesion molecules on surfaces of antigen-presenting cells to provide a second signal (i.e., a co-stimulatory signal) for activation of T cells or B cells. As a third signal, multiple lymphokines produced by activated antigen-presenting cells and T cells participate in lymphocyte proliferation and differentiation through autocrine and paracrine actions, and eventually form effector T cells or plasmocytes. The most important function of effector T cells is to kill infected cells through $CD8^+$ cytotoxic T cells (CTL) and activate macrophages through Th1 cells, which make up cellular immunity together. In addition, B cells are activated by Th2 cells to produce different types of antibodies, thereby activating humoral immune responses.

The third phase is an effector phase in which immune effector cells and effector molecules (cytokines and antibodies) work together to remove non-autoantigens and keep the body in a normal physiological state.

8. Memory immune response: Immune memory is an important feature of adaptive immunity, that is, the body will present a secondary response with increased response speed and intensity when exposed to the antigen resulting in sensitization for the first time again. The key to immune memory is the formation and maintenance of memory lymphocytes. Induction of protective immune memory responses includes humoral immune responses mediated by memory B lymphocytes and cellular immune responses mediated by memory T lymphocytes.

Antigen stimulation determines the number of antigen-specific CD8+T cells produced in a primary response. About 5% of antigen-specific CD8+T cells are transformed into memory CD8+T cells. Memory T cells (Tm) can rapidly mature into effector memory T cells ($T_{EM}$) after being stimulated by the antigen again, and produce a large amount of IFN-γ, IL-4 and IL-5 in the early phase.

Compared with naive T cells stimulated by antigen for the first time, the memory T cells have the following advantages: (1) when exposed to the same antigen again, the memory T cells can present stronger proliferation ability, cytokine secretion ability and CTL activity. (2) The reactivation of memory T cells by the same antigen requires a lower threshold than the primary response. (3) It is generally believed that the maintenance of memory CD8+T cells does not need continuous stimulation of the antigen and has self-renewal capability. (4) Reactivated memory T cells can release a large number of cytokines such as IFN-γ, IL-4 and IL-5, thus promoting T cells to kill tumors. (5) Memory T cells can produce effector cells with rapid and strong immune responses without homing to secondary lymphoid organs.

9. DNA/Cationic Lipid Materials:

The cationic lipids of the invention have positive charges on surfaces thereof and are easy to form DNA/cationic lipid materials by electrostatic interaction with negatively charged DNA. Generally, positive charges on the surfaces of the formed DNA/cationic lipid materials are adsorbed to negatively charged cell surfaces by electrostatic interaction, and DNA is transferred into cells through fusion with cell membranes or endocytosis to form inclusion bodies or enter lysosomes. Under the action of the cationic lipids, anionic lipids on cell membranes lose original balance due to destabilization of membranes and diffuse into complexes, forming neutral ion pairs with cations in the cationic lipids, so that DNA originally bound with liposomes can dissociate out and enter cytoplasm.

10. Plasmids

Plasmids in the art generally refer to original circular DNA molecules that can replicate autonomously by attaching to non-cellular chromosomes or nucleus regions in cells.

It should be noted that the invention reconstructs a type of replicable circular DNA molecules that cannot express exogenous genes, which belong to a type of new plasmids. The plasmids constructed by the invention can enter tumor cells after forming complexes with cationic biomaterials. As a result, ROS in the tumor cells increases obviously, so that plasmids in the plasmid/cationic biomaterial complexes can be oxidized by ROS to form oxidized DNA, allowing lysosomes in the tumor cells to rupture, which can directly mediate tumor cell necrosis on one hand, and activate anti-tumor immune responses on the other hand. In addition, the plasmids in the plasmid/cationic biomaterial complexes constructed by the invention can also oxidize DNA in advance by various reported means in vitro, and then enter the bodies to enhance the anti-tumor effects.

11. DNA Oxidation and Oxidative Damages

DNA is often stimulated by various factors in vivo and vitro, such as physicochemical factors, including rays, strong oxidants, strong acids and strong bases as well as endogenous ROS, which will lead to oxidation of DNA under the attack of free radicals. Oxidation often causes oxidative damages to DNA, such as DNA double strand breaks (DSBs), DNA single strand breaks, excision or substitution of bases or base pairs.

DETAILED DESCRIPTION OF PREFERRED EMBODIMENTS

Technical schemes of the invention will be further illustrated below in conjunction with preferred embodiments. It should be noted that some common molecular biology manipulations and common procedures for preparing pharmaceutical preparations in the invention can be completed by a person skilled in the art on the basis of reading the specification of the invention in combination with existing textbooks, manuals and instructions for use of related equipments and reagents in the art.

The invention will be further described in detail below in combination with examples and drawings, but embodiments of the invention are not limited thereto.

Example 1 Construction and Expression of pMVA and pMVA-1 Plasmids (1) Construction and Expression of pMVA Plasmid A 1978 bp nucleotide sequence, including a pUC origin sequence and kanamycin genes as well as two plasmid skeleton sequences was synthesized by total gene synthesis, which was ligated and cyclized into a pMVA plasmid having a nucleotide sequence as shown in SEQ ID NO. 1. The structure of the pMVA plasmid was shown in FIG. 1A.

Figure 2:
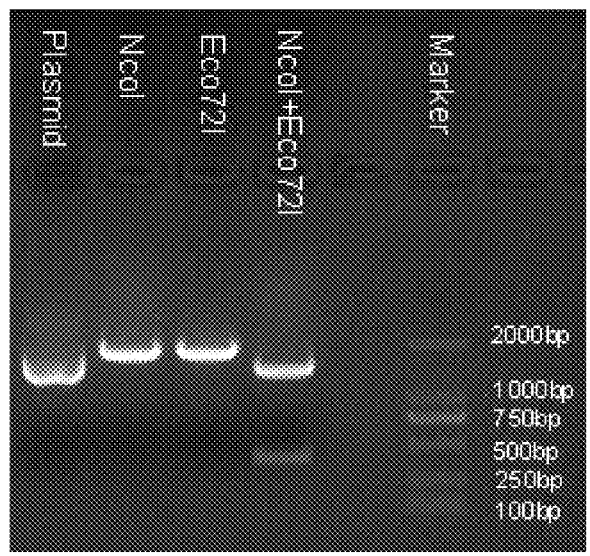
FIG. 2 shows the results of enzyme digestion of pMVA plasmids by NcoE I enzyme and Eco72 I enzyme verified by agarose gel electrophoresis, wherein the molecular weight of closed loop plasmids (i.e., pMVA-1 plasmids) is consistent with that of plasmid fragments after enzyme digestion by NcoE I enzyme and Eco72 I enzyme, approximately 2000 bp.

Agarose gel electrophoresis was performed for enzyme digestion verification, with experimental results as shown in FIG. 2.

The constructed pMVA plasmid was expressed in *Escherichia coli* DH5a.

(2) Construction and Expression of pMVA-1 Plasmid

Figure 1B:
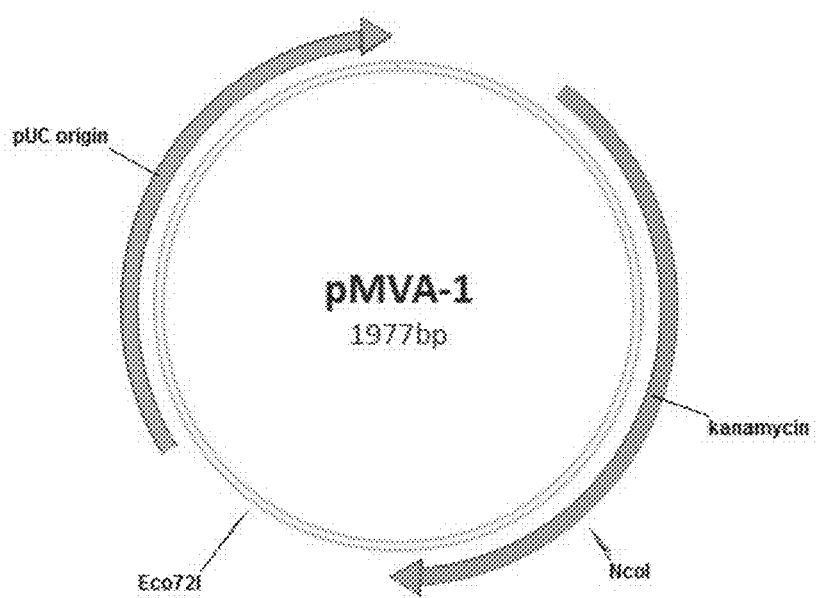

The constructed pMVA plasmid was subjected to base site-directed mutagenesis or deletion to obtain a pMVA-1 plasmid having 1977 bp in total. Mutation sites included bases 2, 3, 4, 41 and 1950 of the nucleotide sequence shown in SEQ ID NO. 1, and deletion site was base 1075 of the nucleotide sequence shown in SEQ ID NO. 1. The nucleotide sequence of the pMVA-1 plasmid vector was shown in SEQ ID NO. 2. The structure of the pMVA-1 plasmid was shown in FIG. 1B.

The constructed pMVA-1 plasmid was expressed in *Escherichia coli* DH5a, and the yield was significantly better than that of the pMVA plasmid.

Example 2 Screening of Mitochondrial DNA (mtDNA) Target Sequence 50-3000 bp mtDNA was selected, including mtDNA as shown in SEQ ID NO. 3, 4 and 5. mtDNA or mtDNA fragment was rich in CpG motifs, thus it could be used as an agonist of TLR9 pathway or STING pathway. When tumor cells were under oxidative stress, the selected mtDNA target sequence could effectively activate the body's anti-tumor innate immunity response.

Example 3 Construction and Expression of Plasmid (1) Construction and Amplification of pMVA-2 Plasmid An mtDNA nucleotide sequence 1 as shown in SEQ ID NO. 3 screened in Example 2 and a linear sequence before cyclization of the pMVA in Example 1 were genetically synthesized, and then ligated and cyclized into a pMVA-2 plasmid having 2098 bp in total. The nucleotide sequence of the pMVA-2 plasmid was shown in SEQ ID NO. 6, wherein the nucleotide sequence at sites 33 to 152 was shown in SEQ ID NO. 3.

The constructed pMVA-2 plasmid was amplified in *Escherichia coli* DH5a.

(2) Construction and Amplification of pMVA-3 Plasmid

An mtDNA nucleotide sequence 2 as shown in SEQ ID NO. 4 screened in Example 2 and a linear sequence before cyclization of the pMVA in Example 1 were genetically synthesized, and then ligated and cyclized into a pMVA-3 plasmid having 2578 bp in total. The nucleotide sequence of the pMVA-3 plasmid was shown in SEQ ID NO. 7, wherein the nucleotide sequence at sites 33 to 632 was shown in SEQ ID NO. 4.

The constructed pMVA-3 plasmid was amplified in *Escherichia coli* DH5a.

(3) Construction and Amplification of pMVA-4 Plasmid

An mtDNA nucleotide sequence 3 as shown in SEQ ID NO. 5 screened in Example 2 and a linear sequence before cyclization of the pMVA in Example 1 were genetically synthesized, and then ligated and cyclized into a pMVA-4 plasmid having 3978 bp in total. The nucleotide sequence of the pMVA-4 plasmid was shown in SEQ ID NO. 8, wherein the nucleotide sequence at sites 33 to 2032 was shown in SEQ ID NO. 5.

The constructed pMVA-4 plasmid was amplified in *Escherichia coli* DH5a.

(4) Construction and Amplification of pMVA-5 Plasmid

A nucleotide sequence 1 of the mtDNA fragment shown in SEQ ID NO. 3 screened in Example 2 and a linear sequence before cyclization of the pMVA-1 in Example 1 were genetically synthesized, and then ligated and cyclized into a pMVA-5 plasmid. The nucleotide sequence of the pMVA-5 plasmid was shown in SEQ ID NO. 9, wherein the nucleotide sequence at sites 33 to 152 was an inserted nucleotide sequence shown in SEQ ID NO. 3.

The constructed pMVA-5 plasmid was amplified in *Escherichia coli* DH5a.

(5) Construction and Amplification of pMVA-6 Plasmid

A nucleotide sequence 2 of the mtDNA fragment shown in SEQ ID NO. 4 screened in Example 2 and a linear sequence before cyclization of the pMVA-1 were genetically synthesized, and then ligated and cyclized into a pMVA-6 plasmid. The nucleotide sequence of the pMVA-6 plasmid was shown in SEQ ID NO. 10, wherein the nucleotide sequence at sites 33 to 632 was an inserted nucleotide sequence shown in SEQ ID NO. 4.

The constructed pMVA-6 plasmid was amplified in *Escherichia coli* DH5a.

(6) Construction and Amplification of pMVA-7 Plasmid

A nucleotide sequence 3 of the mtDNA fragment shown in SEQ ID NO. 5 screened in Example 2 and a linear sequence before cyclization of the pMVA-1 in Example 1 were genetically synthesized, and then ligated and cyclized into a pMVA-7 plasmid. The nucleotide sequence of the pMVA-7 plasmid was shown in SEQ ID NO. 11, wherein the nucleotide sequence at sites 33 to 2032 was an inserted nucleotide sequence shown in SEQ ID NO. 5.

The constructed pMVA-7 plasmid was amplified in *Escherichia coli* DH5a.

Example 4 Preparation of Cationic Biomaterial

1. Preparation Method of Cationic Lipid Material (DOTAP/CHOL Complex or DOTAP)

(1) As shown in Table 1, weighed heat-free DOTAP and heat-free cholesterol (CHOL) were mixed, then 1-1.5 L of anhydrous ethanol solution was added to obtain a mixed solution which was heated to 50° C. to completely dissolve lipid under stirring.

(2) The mixed solution from Step (1) was subject to rotary evaporation at 40° C., 0.08 MPa to ⅓ of the volume of the solution, and then diluted with water to a constant volume.

(3) The solution obtained in Step (2) was homogenized in a high pressure homogenizer at a pressure of 700-800 bar for 3-10 times and extruded from an 50° C. extruder (100 nm film) for 1-2 times to obtain a cationic lipid material (DOTAP/CHOL complex or DOTAP) with a particle diameter of 100-150 nm and PDI<0.3.

TABLE 1

DOTAP and CHOL compounded by different mass ratios

| Mass ratio | Lipid | |
|---|---|---|
| | DOTAP (g) | CHOL (g) |
| 1:0 | 1 | 0 |
| 1:5.2 | 2 | 10.4 |
| 1.8:1 | 9.655 | 5.345 |
| 2:1 | 10 | 5 |
| 2.26:1 | 10.4 | 4.6 |

2. Preparation Method of PEI Polymer

PEI 25 kD was prepared with distilled water into 6 mg/mL, 4 mg/mL and 0.4 mg/mL solutions.

3. Preparation Method of Chitosan

Medium molecular weight chitosan was dissolved in a dilute acid to prepare 6 mg/mL, 4 mg/mL and 0.4 mg/mL solutions.

Example 5 Preparation of DNA/Cationic Biomaterial Complexes

The screened mtDNA or fragments thereof and the constructed plasmid vector or plasmid were aseptically mixed with the cationic biomaterial prepared in Example 4 respectively in equal volume at different concentrations shown in Tables 2-4 to obtain mixed solutions, then the solutions were allowed to stand for 0.5 h to form DNA/cationic biomaterial complexes.

TABLE 2

DNA/cationic lipid materials with different mass ratios

| Mass ratio | Concentration | | |
|---|---|---|---|
| | DNA (mg/ml) | DOTAP (mg/ml) | DOTAP/CHOL (mg/ml) |
| 1:1 | 0.4 | 0.4 | 0.4 |
| 1:6 | 0.4 | 2.4 | 2.4 |
| 1:10 | 0.4 | 4 | 4 |
| 1:15 | 0.4 | 6 | 6 |
| 1:20 | 0.3 | 6 | 6 |

TABLE 3

DNA/PEI 25 kD complexes with different mass ratios

| Mass ratio | Concentration | |
|---|---|---|
| | DNA (mg/ml) | PEI 25 kD (mg/ml) |
| 1:1 | 0.4 | 0.4 |
| 1:10 | 0.4 | 4 |
| 1:20 | 0.3 | 6 |

TABLE 4

DNA/chitosan complexes with different mass ratios

| Mass ratio | Concentration | |
|---|---|---|
| | DNA (mg/ml) | Chitosan (mg/ml) |
| 1:1 | 0.4 | 0.4 |
| 1:10 | 0.4 | 4 |
| 1:20 | 0.3 | 6 |

Example 6 Characterization of DNA/Cationic Biomaterial Complexes

1. Determination of Particle Size and Potential of DNA/Cationic Biomaterial Complexes:

(1) Preparation of DNA/Cationic Biomaterial Complex Samples:

Sterile distilled water was added to the DNA/cationic biomaterial complexes with different mass ratios prepared in Example 5 to dissolve the complexes under high speed oscillation to obtain mixed solutions which were allowed to stand at room temperature.

(2) Determination of Particle Size and Potential of DNA/Cationic Biomaterial Complexes The DNA/cationic biomaterial complex samples prepared in Step (1) were added to sample dishes of a Malverl Zetasizer Nano ZS, then the sample dishes were put into a test cell to test 3 groups of data in parallel for each sample, with the equilibrium time set at 1 min, thus obtaining the mean particle size and Zeta potential of the complex samples. The test results were shown in Tables 5-7.

TABLE 5

Particle size and potential of DNA/cationic lipid materials with different mass ratios

| Mass ratio (DNA:cationic lipid) | Particle size (nm) | PdI | Zeta potential (mV) |
|---|---|---|---|
| 1:1 | 122 | 0.215 | 14.6 |
| 1:6 | 149.1 | 0.193 | 23.3 |
| 1:10 | 140.7 | 0.228 | 23.0 |
| 1:15 | 134.0 | 0.238 | 25.2 |
| 1:20 | 124.1 | 0.236 | 23.4 |

TABLE 6

Particle size and potential of DNA/PEI 25 kD complexes with different mass ratios

| Mass ratio (DNA:PEI25 kD) | Particle size (nm) | Zeta potential (mV) |
|---|---|---|
| 1:1 | 50.9 | 19.4 |
| 1:10 | 60.27 | 25.3 |
| 1:20 | 74.47 | 34.7 |

TABLE 7

Particle size and potential of DNA/chitosan complexes with different mass ratios

| Mass ratio (DNA:chitosan) | Particle size (nm) | Zeta potential (mV) |
|---|---|---|
| 1:1 | 135.4 | 26.4 |
| 1:10 | 163 | 28.3 |
| 1:20 | 236.6 | 51.4 |

Example 7 Determination of DNA/Cationic Lipid Material Complexes with Different Mass Ratios by Agarose Gel Electrophoresis (1) Preparation of 1% agarose gel: agarose was weighed and placed in a conical flask, then 1×TAE was added, and the agarose was heated and boiled in a microwave oven until the agarose was completely melted, then DNA dye Golden View was added, and the conical flask was shaken well to prepare a 1.0% agarose gel solution.

(2) Preparation of gel slab: after a gel slab is prepared, the agarose gel prepared in Step (1) was cooled to 65° C. and poured on a glass plate in an inner groove to form a uniform gel layer which was allowed to stand at room temperature until the gel is completely coagulated, and the gel and the inner groove were put into an electrophoresis tank. Then 1×TAE electrophoresis buffer was added until it was 1-2 mm above the gel slab.

(3) Sample loading: DNA/DOTAP complex samples with DOTAP: DNA mass ratios of 1:1, 6:1, 10:1, 15:1 and 20:1 were mixed with a loading buffer respectively and then added to gel pores prepared in Step (2).

(4) Electrophoresis: after sample loading, the gel slab was electrified immediately for electrophoresis. When bromophenol blue moved to a position about 1 cm from the lower edge of the gel slab, electrophoresis was stopped.

(5) A gel imaging system was used for photographing and preservation.

Figure 3:
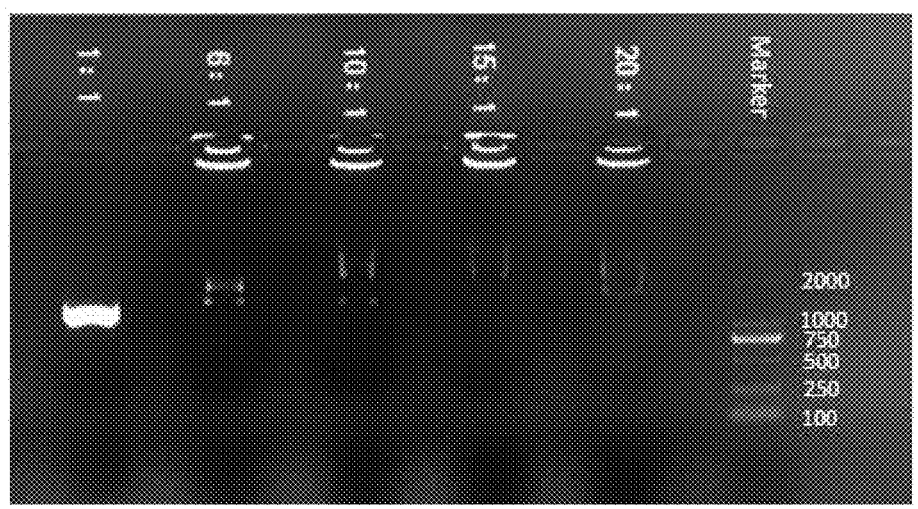
FIG. 3 shows a detection diagram of DNA/DOTAP complexes with different mass ratios by agarose gel electrophoresis.

As shown in FIG. 3, the determination of DNA/cationic lipid material complexes with different mass ratios by agarose gel electrophoresis showed that DNA could be effectively retained under the action of agarose gel electrophoresis when DOTAP:DNA mass ratios of DNA/DOTAP complexes were 1:1, 6:1, 10:1, 15:1 and 20:1 respectively.

Example 8 Determination of Activity of A549 Cells Treated with pMVA-1/DOTAP Complexes by CCK8 Method (1) Cell Plate Culture A549 cells in logarithmic growth phase were prepared into a cell suspension which was diluted to $5 \times 10^4$ cells/ml with 10% FBS-1640 to obtain a diluent, then the diluent was inoculated to a 96-well cell culture plate at a ratio of 100l/well, and incubated in 5% $CO_2$ at 37.0° C. for 24 h. After cell attachment, the cells were starved in a serum-free 1640 medium for 24 h.

(2) Preparation of Samples to be Tested

The pMVA-1/DOTAP complexes prepared by mixing at different mass ratios (with DOTAP:pMVA-1 mass ratios of 1:1, 6:1, 10:1, 15:1 and 20:1 respectively) were diluted with a 1640 medium to 200 μg/ml, and then diluted by 3×, with a total of 9 dilution gradients, to prepare test samples with different DOTAP concentrations.

(3) Sample Loading

The 1640 medium in the 96-well plate was absorbed, then the test samples in Step (2) and control samples were added, with 3 parallel gradients for each gradient, 9 gradients in total. The last row was used as cell blank control and blank control. The samples were incubated in 5% CO2 at 37.0° C. for 48 h.

(4) Determination of Cell Activities by CCK-8

CCK-8 and 1640 medium were mixed at a ratio of 1:1, then added to the 96-well plate in Step (3) at a ratio of 20 μl/well, and incubated in 5% CO2 at 37.0° C. for 2 h to read OD450 nm absorbance by a microplate reader.

(5) Data Analysis

The absorbance determined in Step (4) and the concentration gradients of samples to be tested were fitted into a 4-parameter curve which was a horizontal "S" curve, and inhibitory concentration (IC50) was calculated according to the fitted curve.

Figure 4:
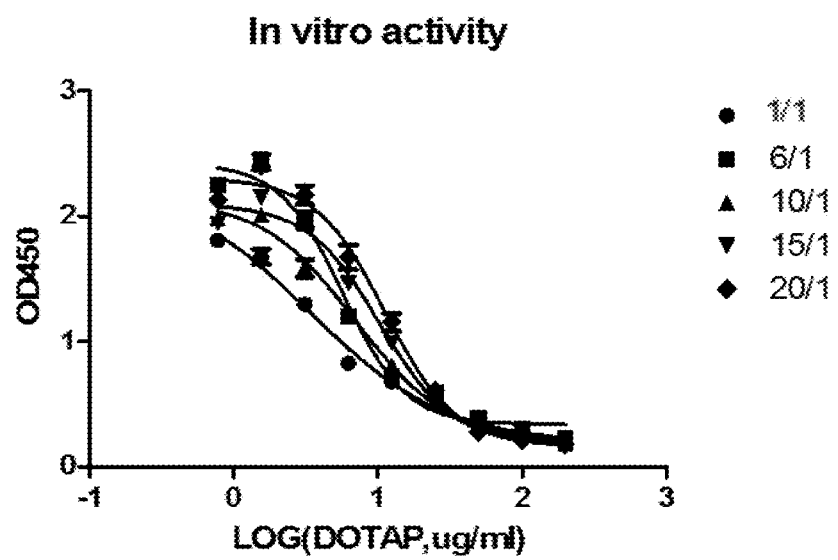
FIG. 4 shows a detection diagram of pMVA-1/DOTAP complexes with different mass ratios inhibiting A549 cell activity in vitro: where, ● represents pMVA-1/DOTAP complex with a DOTAP: pMVA-1 mass ratio of 1:1; ■ represents pMVA-1/DOTAP complex with a DOTAP: pMVA-1 mass ratio of 6:1; ▲ represents pMVA-1/DOTAP complex with a DOTAP:pMVA-1 mass ratio of 10:1; ▼ represents pMVA-1/DOTAP complex with a DOTAP: pMVA-1 mass ratio of 15:1; and ■ represents pMVA-1/DOTAP complex with a DOTAP:pMVA-1 mass ratio of 20:1.

As shown in FIG. 4, the pMVA-1/DOTAP complexes with different mass ratios inhibited the activities of A549 tumor cells in vitro, which showed that the pMVA-1/DOTAP complexes with DOTAP:pMVA-1 mass ratios of 1:1, 6:1, 10:1, 15:1 and 20:1 respectively could effectively inhibit the growth activities of A549 cells.

Example 9 Determination of Bioactivities of pMVA-1/PEI 25 kD Complexes by A549 Cells (1) Cell Plate Culture The method was the same as that in Example 8.

(2) Preparation of Samples to be Tested

The complexes prepared by mixing at different mass ratios (with PEI 25 kD:pMVA-1 mass ratio and chitosan: pMVA-1 mass ratio of 1:1, 10:1 and 20:1 respectively) were diluted with a 1640 medium to 200 μg/ml, and then diluted by 3×, with a total of 9 dilution gradients, to prepare test samples with different PEI 25 kD concentrations.

(3) Sample Loading

The method was the same as that in Example 8.

(4) Determination of Cell Activities by CCK-8

The method was the same as that in Example 8.

(5) Data Analysis

The method was the same as that in Example 8.

Figure 5:
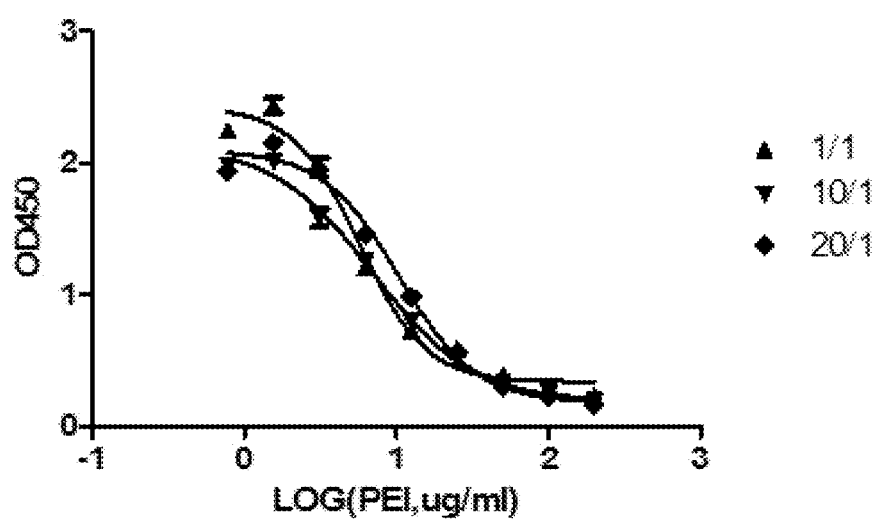
FIG. 5 shows a detection diagram of pMVA1/PEI25D complexes with different mass ratios inhibiting A549 cell activity in vitro: where, ● represents pMVA-1/PEI25KD complex with a PEI25KD: pMVA-1 mass ratio of 1:1; ▼ represents pMVA-1/PEI25KD complex with a DOTAP: pMVA-1 mass ratio of 10:1; and ♦ represents pMVA-1/PEI25KD complex with a DOTAP: pMVA-1 mass ratio of 20:1.

As shown in FIG. 5, the pMVA-1/PEI 25 kD complexes with different mass ratios inhibited the activities of A549 tumor cells in vitro, which showed that the pMVA-1/PEI 25 kD complexes with DOTAP:pMVA-1 mass ratios of 1:1, 10:1 and 20:1 respectively could effectively inhibit the growth activities of A549 cells.

The DNA/PEI complexes were prepared into a tumor vaccine and applied to the treatment of tumor-bearing mice, which could effectively induce anti-tumor immune responses of the tumor-bearing mice and inhibit the growth of tumor cells.

Example 10 Determination of Bioactivities of pMVA-1/Chitosan Complexes by A549 Cells (1) Cell Plate Culture The method was the same as that in Example 8.

(2) Preparation of Samples to be Tested

Test samples with different chitosan concentrations were prepared respectively by the same method as that in Example 9.

(3) Sample Loading

The method was the same as that in Example 8.

(4) Determination of Cell Activities by CCK-8

The method was the same as that in Example 8.

(5) Data Analysis

The method was the same as that in Example 8.

Figure 6:
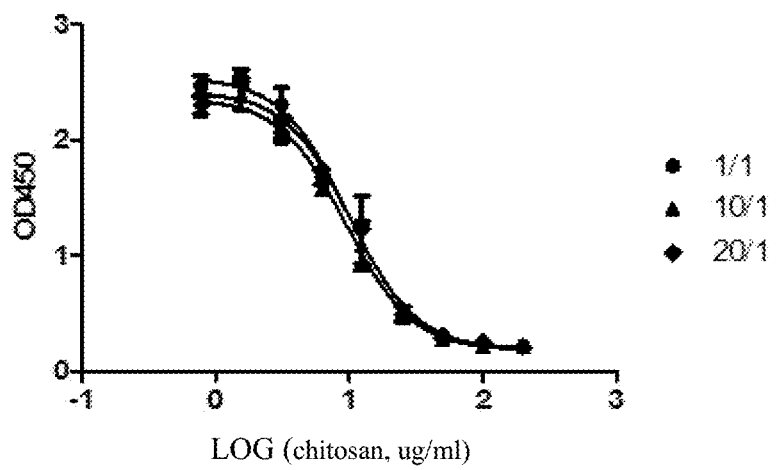
FIG. 6 shows a detection diagram of pMVA1/chitosan complexes with different mass ratios inhibiting A549 cell activity in vitro: where, ● represents pMVA-1/chitosan complex with a chitosan: pMVA-1 mass ratio of 1:1; ▼ represents pMVA-1/chitosan complex with a chitosan: pMVA-1 mass ratio of 10:1; and ♦ represents pMVA-1/chitosan complex with a chitosan: pMVA-1 mass ratio of 20:1.

As shown in FIG. 6, the pMVA-1/chitosan complexes with different mass ratios inhibited the activities of A549 tumor cells in vitro, which showed that the pMVA-1/chitosan complexes with DOTAP:pMVA-1 mass ratios of 1:1, 10:1 and 20:1 respectively could effectively inhibit the growth activities of A549 cells.

The DNA/chitosan complexes were prepared into a tumor vaccine and applied to the treatment of tumor-bearing mice, which could effectively induce anti-tumor immune responses of the tumor-bearing mice and inhibit the growth of tumor cells.

Example 11 Experiment of pMVA-1/DOTAP Complex Synergistically Inducing Tumor Cell Death 1. A549 Cell Death Test by PI-AnnexinV (1) Inoculation of A549 Cells in Plates:

A549 cells in the logarithmic growth phase were prepared into single cell suspension, inoculated into a 6-well plate as per approximately $1\times10^5$ cells per well. Then, 2 ml of medium was added to each well and cultured in a 5% $CO_2$ incubator at 37° C. for 24-36 h.

(2) Preparation of Spiked Sample:

a. 5 mg/ml of pMVA-1 plasmid vector solution was added to 100 μl of 1640 serum-free medium for preparing a pMVA-1 plasmid vector control group;

b. 1 mg/ml of DOTAP cationic lipid was dissolved in 100 μl of 1640 serum-free medium for preparing a DOTAP cationic lipid control group;

c. the pMVA-1/DOTAP complex with a mass ratio of 1:6 prepared in Example 5 was dissolved in 100 μl of 1640 serum-free medium for preparing a pMVA-1/DOTAP complex experimental group.

(3) Treatment of A549 Cells with Spiked Sample:

Some of the medium was pipetted from the 6-well plate in Step (1) until the medium in each well reached 900 μl. The pMVA-1/DOTAP complex (pMVA-DOTAP) (prepared in Step (2)) of the experimental group as well as the pMVA-1 plasmid vector (PMVA) and DOTAP cationic lipid (DOTAP) of the control group was added to A549 cells cultured in Step (1) respectively to make the total volume of 1 ml. At the same time, a blank control group containing only medium was made, and incubated in a 5% of $CO_2$ incubator at 37° C. for 24 h.

(4) PI-Annexin V Staining Marker

A549 cells treated with different samples in Step (3) were washed twice with PBS, and 500 μL of binding buffer from the apoptosis kit (Annexin V-PI assay kit, made by BD Biosciences) was added to each well, 10 μl of PI and 10 μl of Annexin V were added for staining, and then incubated at room temperature for 15 min in the dark.

(5) Observation under fluorescence microscope:

The cells stained with PI and Annexin V in Step (4) were washed once with PBS and observed under a fluorescence microscope. Then images were saved.

Figure 7A:
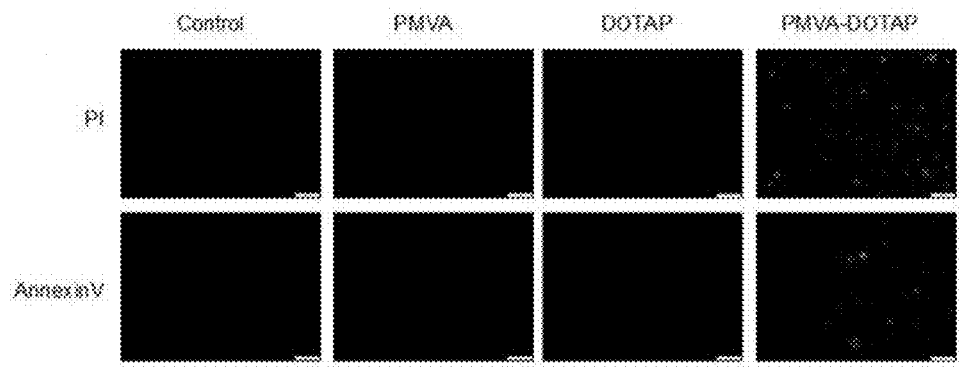
FIGS. 7A and 7B show fluorescence micrograph of tumor apoptosis co-induced by pMVA-1/DOTAP complexes detected by a PI-AnnexinV assay.

(6) Test results of A549 cell death by PI-AnnexinV:

As shown in FIG. 7A, a large number of PI-positive and AnnexinV-positive cells existed after A549 cells were treated with the pMVA-1/DOTAP complex for 24 h, while the pMVA-1 plasmid vector group and DOTAP cationic lipid group (both were control groups) did not indicate obvious PI uptake and AnnexinV-labeled positive cells. The experimental results show that the pMVA-1/DOTAP complex can synergistically induce the death of A549 cells.

2. CT26 cell death test by PI-AnnexinV (1) Experimental method: same as 1.

Figure 7B:
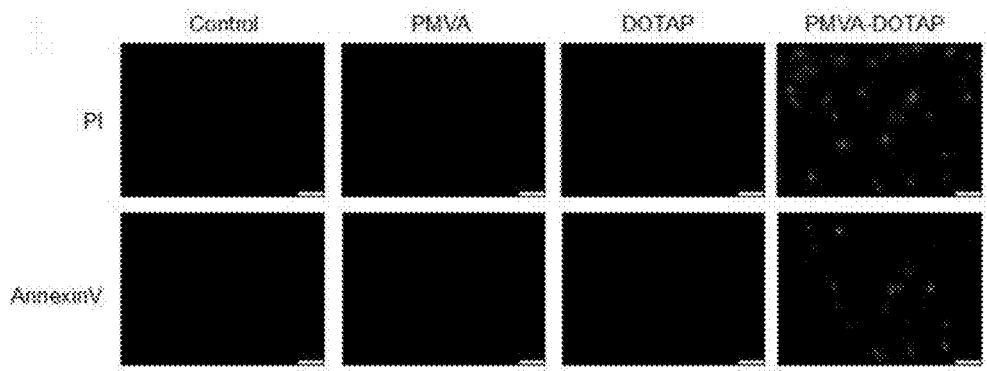

(2) Test results of CT26 cell death by PI-AnnexinV:

As shown in FIG. 7B, a large number of PI-positive and AnnexinV-positive cells existed after CT26 cells were treated with the pMVA-1/DOTAP complex for 24 h, while the pMVA-1 plasmid vector group and DOTAP cationic lipid group (both were control groups) did not indicate obvious PI uptake and obvious AnnexinV-labeled positive cells. The experimental results show that the pMVA-1/DOTAP complex can synergistically induce the death of CT26 cells.

3 A549 Cell Death Test by Flow Cytometry (1) Inoculation of A549 Cells in Plates:

The method was the same as that in 1(1).

(2) Preparation of Spiked Sample:

The method was the same as that in 1(2), wherein, the concentration of DOTAP cationic lipid was 4 μg/ml, 8 μg/ml, 16 μg/ml and 32 μg/ml respectively, and the concentration of the pMVA-1/DOTAP complex was expressed by that of DOTAP cationic lipid.

(3) Treatment of A549 Cells with Spiked Sample:

The method was the same as that in 1(3).

(4) Quantitative Test of A549 Cell Death by Flow Cytometry a. A549 cells treated by different samples in the Step (3) were washed twice with cold PBS, and resuspended with 1× binding buffer for preparing a cell suspension with a density of $1\times10^6$ cells/ml;

b. 100 μl of A549 cell suspension prepared in Step a was pipetted into the flow test tube;

c. 5 μl of FITC Annexin V and 5 μl of PI were added to the flow test tube in Step b, mixed gently, and incubated at room temperature for 15 min in the dark;

d. 400 μl of 1× binding buffer was added to the flow test tube in Step c and tested by flow cytometry;

(5) Quantitative Test Results of A549 Cell Death by Flow Cytometry:

Compared with the blank control group to which only medium was added, Annexin-V single positive cells, PI single positive cells and PI/Annexin-V double positive cells from A549 cells did not increase significantly in the pMVA-1 plasmid vector group (PMVA) and DOTAP cationic lipid group (DOTAP) (both were control groups). However, the PI uptake and Annexin-V increased significantly in the experimental group, i.e. the pMVA-1/DOTA complex group (pMVA/DOTA), compared with the blank control group and the control group, and the percentage of dead cells increased with the increase of concentration of the pMVA-1/DOTAP complex, indicating a significant dose-dependent relationship. As shown in FIG. 8A, when the concentration of pMVA-1/DOTAP complex was 4 μg/ml, 8 μg/ml, 16 μg/ml and 32 μg/ml, the percentage of total dead cells (including necrotic cells and apoptotic cells) was 1.68%, 21.63%, 57.22% and 65.37%, respectively.

4 CT26 Cell Death Test by Flow Cytometry (1) Experimental method: same as 3, wherein the concentration of DOTAP cationic lipid was 2 μg/ml, 4 μg/ml, 8 μg/ml and 16 μg/ml respectively, and the concentration of the pMVA-1/DOTAP complex was expressed by that of DOTAP cationic lipid.

(2) Test results of CT26 cell death by flow cytometry:

As shown in FIG. 8B, it was observed that experimental result of CT26 cells was similar to that of A549 cells, i.e., the pMVA-1/DOTAP complex could synergistically induce the death of tumor cells.

The experimental results show that neither pMVA-1 plasmid nor DOTAP cationic lipid can cause apoptosis or necrosis of tumor cells when they act on tumor cells separately, but when the pMVA-1/DOTAP complex formed by pMVA-1 plasmid and DOTAP cationic lipid acts on tumor cells, it can induce the death of tumor cells, and the process of apoptosis or necrosis is different from the rapid death of tumor cells caused by DOTAP cationic lipid alone in the absence of serum, which is a slow death process.

Example 12 ROS Level Increase in Tumor Cells Synergistically Induced by pMVA-1/DOTAP Complex Detected by H2DCF-DA Fluorescence Molecular Probe Method (1) Sample loading: A549 cells were treated with the medium (blank control group), pMVA-1 plasmid (control group PMVA), DOTAP cationic lipid (control group DOTAP) and pMVA-1/DOTAP complex (experimental group PMVA-DOTAP) for 3 h respectively. Then, a negative control group (NAC) was made for pretreatment with 5 mM NAC before the action of pMVA-1/DOTAP complex, and a positive control group ($H_2O_2$) was made by adding 200 μM of $H_2O_2$ to A549 cells.

(2) A549 cells of different groups in the Step (1) were collected and washed with sterile PBS, centrifuged and resuspended with sterile PBS;

(3) 10M CM-H2DCFDA fluorescent probe (made by Sigma) was added to the resuspended cells prepared in Step (2), incubated at 37° C. for 0.5 h, washed with PBS and resuspended;

(4) The resuspended cells in Step (3) were tested with flow cytometry (Novocyte), and the test results were analyzed by Novoexpress software.

(5) Experimental results:

As shown in FIG. 9, compared with the blank control group, the PMVA control group and the DOTAP group, the intracellular ROS level of A549 cells treated with pMVA-1/DOTAP complex increased significantly (*$P<0.05$); however, when A549 cells were pretreated with 5 mM NAC before they were treated with the pMVA-1/DOTAP complex, the negative control group indicated that the intracellular ROS level decreased significantly; and the positive control group indicated that the ROS level in cells treated with 200 μM $H_2O_2$ increased significantly (*$P<0.05$).

Thus, the pMVA-1/DOTAP complex can synergistically induce a significant increase of ROS level in A549 cells.

Figure 10:
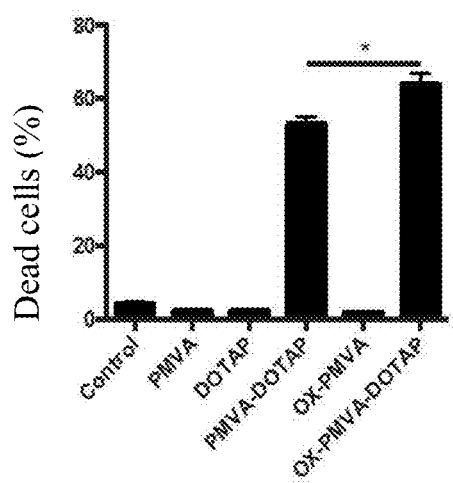
FIG. 10 is a graph showing the effect of ox-pMVA-1/DOTAP complexes formed by oxidized pMVA-1 plasmids and DOTAP cationic lipids on A549 apoptosis. All results were expressed as mean relative expression ±SD, *P<0.05.

Example 13 Mechanism Study on pMVA-1/DOTAP Complex Synergistically Inducing ROS Increase of Tumor Cells Example 12 proves that the pMVA-1/DOTAP complex can synergistically induce the increase of ROS level in A549 cells. In order to investigate the effect of plasmid oxidation of the pMVA-1/DOTAP complex on tumor cell death, the pMVA-1 plasmid was oxidized by 1000 mJ/cm2 UV irradiation, and then formed a complex with DOTAP cationic lipid to act on A549 cells. As shown in FIG. 10, when A549 cells were treated with the ox-PMVA-1/DOTAP complex for 24 h, the number of A549 cell deaths increased significantly compared with the pMVA-1/DOTAP complex group.

The experimental results show that the destruction of the pMVA-1/DOTAP complex on tumor cells is related to the oxidative stress of the pMVA-1 plasmid in tumor cells.

Figure 11:
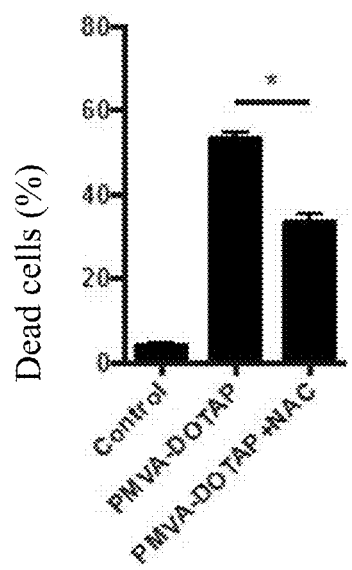
FIG. 11 is a graph showing tumor apoptosis co-induced by pMVA-1/DOTAP complexes is related to oxidative stress of tumor cells. Flow cytometry is performed to determine the death rate of A549 cells pretreated with NAC before pMVA-1/DOTP complexes were added. All results were expressed as mean relative expression ±SD, *P<0.05.

Example 14 Synergistic Induction of Tumor Cell Death by the pMVA-1/DOTAP Complex is Related to Oxidative Stress of Tumor Cells Example 12 proves that N-Acetyl-L-cysteine (NAC), as an antioxidant, can effectively inhibit the increase of ROS level in tumor cells induced by the pMVA-1/DOTAP complex. In order to further verify whether the synergistic induction of tumor cell death by the pMVA-1/DOTAP complex is related to oxidative stress of tumor cells, the flow cytometry was used to test the death ratio of A549 cells pretreated with NAC before adding pMVA-1/DOTP complex in Example 12. As shown in FIG. 11, A549 cells are pretreated with NAC before they are treated with the pMVA-1/DOTP complex, the death ratio can be significantly reduced, which further proves that the synergistic induction of tumor cell death by the pMVA-1/DOTAP complex is related to the occurrence of oxidative stress in tumor cells.

Example 15 μMVA-1/DOTAP Complex Synergically Induces Lysosomal Rupture of Tumor Cells 1 Test of pMVA-1/DOTAP Complex Entering A549 Cells by YOYO1 Fluorescence Probe Method (1) YOYO1 Dye (Made by Life Technologies) Fluorescently Labeled pMVA-1 Plasmid:

a. Preparation of YOYO1 working fluid: the YOYO1 stock solution was diluted with 1640 serum-free medium at the volume ratio of 1:200;

b. The pMVA-1 plasmid was added to the YOYO1 working fluid prepared in the Step (1) according to a volume ratio of 1:40, and incubated at 37° C. for 1 h.

(2) Treatment of A549 Cells with YOYO1 Fluorescent Labeled pMVA-1/DOTAP Complex:

a. The YOYO1 fluorescent labeled pMVA-1 plasmid prepared in Step 1 was mixed with the DOTAP cationic lipid to form a complex;

b. The YOYO1 fluorescently labeled pMVA-1/DOTAP complex prepared in Step a was added to A549 cells, followed by making two control groups i.e. YOYO1 fluorescently labeled pMVA-1 plasmid group (PMVA) and DOTAP cationic lipid group (DOTAP), and blank control group containing cell culture fluid only.

2 Test of Loss of Lysosomal Acidity Gradient Synergistically Induced by the pMVA-1/DOTAP Complex in A549 Cells Based on Lysotracker Red Fluorescence Probe Method (1) Preparation of Lysotracher Red working fluid: the Lysotracher Red stock solution was added to the cell culture fluid at a volume ratio of 1:20000 and incubated at 37° C.

(2) Lysotracker Red (made by Beyotime) fluorescently labeled lysosomes in A549 cells:

a. The A549 cell culture fluid in Step 1 was removed, the Lysotracker Red staining working fluid prepared in Step (1) was added to the cells, and incubated at 37° C. for 1 h;

b. the Lysotracker Red staining working fluid in Step a was removed, and fresh cell culture fluid was added to observe and collect fluorescence cell images under a fluorescence microscope at 0.5 h and 3 h respectively;

c. A549 cells in Step b were collected and the number of fluorescent cells were quantitatively tested by flow cytometry.

3 Test of Increased Lysosomal Membrane Permeability of A549 Cells Synergistically Induced by pMVA-1/DOTAP Complex Based on FITC-Dextran Cell Localization Method (1) Inoculation of A549 cells in plates: A549 cells in the logarithmic growth phase were prepared into a cell suspension, inoculated into a 6-well plate as per approximately 1×10$^5$ cells/well. Then, 2 ml of medium was added to each well, and cultured overnight in a 5% $CO_2$ incubator at 37° C.

(2) FITC-Dextran (made by Sigma) with a final concentration of 1 mg/ml was added to the cell medium in Step (1), and incubated at 37° C. for 4 h in the dark.

(3) The cells in Step (2) were washed twice with sterile PBS, 1640 medium was added, thus allowing A549 cells to be treated with the medium (blank control group), pMVA-1 plasmid (control group PMVA), DOTAP cationic lipid (control group DOTAP) and pMVA-1/DOTAP complex (experimental group PMVA-DOTAP) respectively, and incubated at 37° C. for 3 h in the dark.

(4) The cells in Step (3) were washed twice with PBS, stabilized with 4% paraformaldehyde for 10 min, washed twice with PBS, sealed. Fluorecytes were observed under a confocal microscope and the images were saved.

4 Test of Increased Lysosomal Membrane Permeability of A549 Cells Synergistically Induced by pMVA-1/DOTAP Complex Based on CathepsinB Intracellular Localization Method (1) Inoculation of A549 cells in plates: round sterilized cell slides were placed at the bottom of a 6-well plate, inoculated A549 cells into the 6-well plate as per 1×10$^5$ cells/well, 2 ml of medium was added to each well, and incubated overnight.

(2) The medium (blank control group), pMVA-1 plasmid (control group PMVA), DOTAP cationic lipid (control group DOTAP) and pMVA-1/DOTAP complex (experimental group PMVA-DOTAP) were added to A549 cells cultured in the Step (1), and incubated at 37° C. for 3 h.

(3) A549 cells treated by different groups in Step (2) were washed twice with PBS, stabilized with ice methanol for 3 min, washed twice with PBS, and sealed with PBST containing 0.3% Triton of 5% FBS for 20 min.

(4) The cells in Step (3) were washed once with PBS, and the human CathepsinB antibody (made by Abcam) was diluted at a ratio of 1:300. Incubating at room temperature for 1 h, washing with PBS three times for 5 minutes each time, adding 1:1000 fluorescent secondary antibody, and incubating at room temperature for 1 h in the dark.

(5) The cells in Step (4) were washed with PBS for three times, the films were washed with ultrapure water to remove excess water, and sealed with anti-fluorescence quencher, then cured for 6 h. Fluorescent cells were observed under a confocal microscope and the images were saved.

Figure 12:
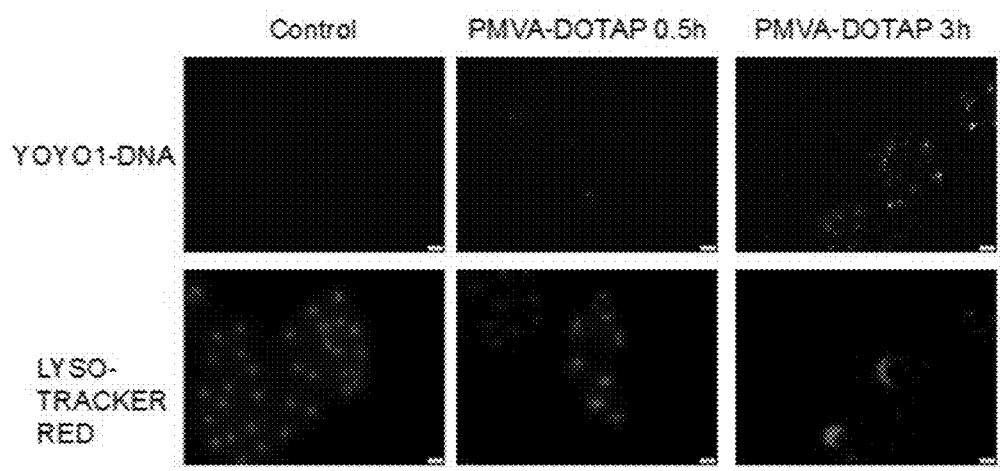
FIG. 12 is a fluorescence micrograph of pMVA-1/DOTAP complexes entering A549 cells and co-inducing loss of lysosomal acidity gradient after the pMVA-1/DOTAP complexes react with A549 cells for 0.5 h and 3 h.

5 Experimental Results of Lysosomal Rupture of Tumor Cells Synergistically Induced by pMVA-1/DOTAP Complex;

(1) pMVA-1/DOTAP Complex Enters A549 Cells and Synergistically Induces Loss of Lysosomal Acidity Gradient in Cells A549 cells were treated with the complex formed by YOYO1 fluorescence probe labeled pMVA-1 plasmid and DOTAP cationic lipid, which could be used as the tracer of pMVA-1/DOTAP complex. Then, lysosomes of A549 cells were labeled with Lysotracker Red, and fluorescence cell images were collected under a fluorescence microscope at 0.5 h and 3 h respectively. As shown in FIG. 12, A549 cells in the blank control group had high Lysotracker Red fluorescence intensity. However, after treated with the pMVA-1/DOTAP complex for 0.5 h, A549 cells began to show YOYO1 labeled pMVA-1 plasmid at the cell membrane and cytoplasmic edge, and lysosomal Lysotracker Red fluorescence intensity slightly decreased. When these cells were treated with the pMVA-1/DOTAP complex for 3 h, large quantities of YOYO1 labeled pMVA-1 plasmid entered the cytoplasm, and the fluorescence intensity of Lysotracker Red in lysosomes decreased significantly, indicating that the pMVA-1/DOTAP complex entered A549 cells and induced acidity gradient changes in lysosomes.

Figure 13:
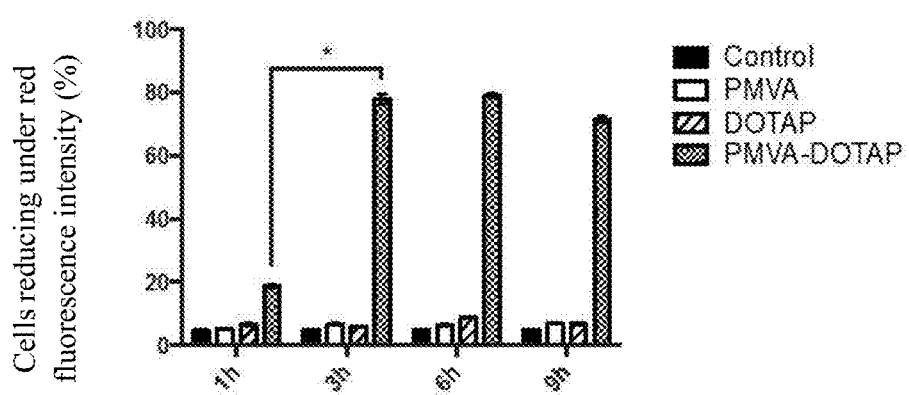
FIG. 13 is a graph showing quantitative determination of changes of Lysotracker red fluorescence intensity in lysosomes of A549 cells exposed to different samples for 1 h, 3 h, 6 h and 9 h respectively by flow cytometry. The percentage of A549 cells with decreased Lysotracker red fluorescence intensity in each group was statistically analyzed. Wherein, for a blank control group: only medium was added to A549 cells; for a PMVA control group: pMVA-1 plasmids were added to A549 cells; for the DOTAP control group: DOTAP was added to A549 cells; and for the PMVA-DOTAP treatment group: pMVA-1/DOTAP complex was added to A549 cells. All results were expressed as mean relative expression ±SD, *P<0.05.

(2) Quantitative Test of Lysotracker Red Fluorescence Intensity in Lysosomes of A549 Cells in Different Groups Based on Flow Cytometry As shown in FIG. 13, Lysotracker Red fluorescence intensity did not change significantly after the cells of the blank control group, the pMVA-1 plasmid group and DOTAP cationic lipid group were treated for 1 h, 3 h, 6 h and 9 h respectively. In the pMVA-1/DOTAP complex group, Lysotracker Red fluorescence intensity of 18.49% A549 cells decreased 1 h after treatment, and that of 76.18% A549 cells decreased 3 h after treatment.

The experimental results show that the pMVA-1/DOTAP complex can enter tumor cells and synergistically induce the imbalance of lysosomal acidity gradient in tumor cells; moreover, as the cells are treated with the complex over time, the loss degree of lysosomal acidity gradient gradually increases and lysosomes is gradually dissolved. Loss of lysosomal acidity gradient in tumor cells occurs 1 h after the complex takes effect, and reaches the maximum when the cells were treated with the complex for 3 h.

Figure 14A:
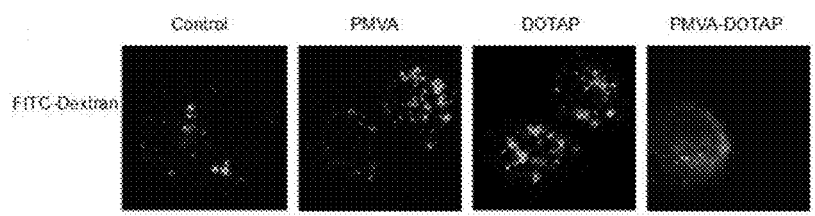
FIGS. 14A and 14B are fluorograms of increased lysosoma membrane permeabilization of A549 cells co-induced by pMVA-1/DOTAP complexes.

(3) Experimental Results of Lysosomal Membrane Permeability Changes in A549 Cells Tested by FITC-Dextran Cell Localization Method FITC-Dextran is a 20 kD dextran that can enter lysosomes through endocytosis. A549 cells are exposed to 1 mg/ml of FITC-Dextran for 3 h and treated with different groups of samples, and the fluorescent cells were observed under a confocal microscope. As shown in FIG. 14A, FITC-Dextran of the cytoplasm of A549 cells was distributed in dots in the blank control group (control), pMVA-1 plasmid group (PMVA) and DOTAP cationic lipid group (DOTAP); and FITC-Dextran was distributed dispersedly in the pMVA-1/DOTAP complex group (PMVA-DOTAP), indicating increased lysosomal membrane permeability (LMP).

Figure 14B:
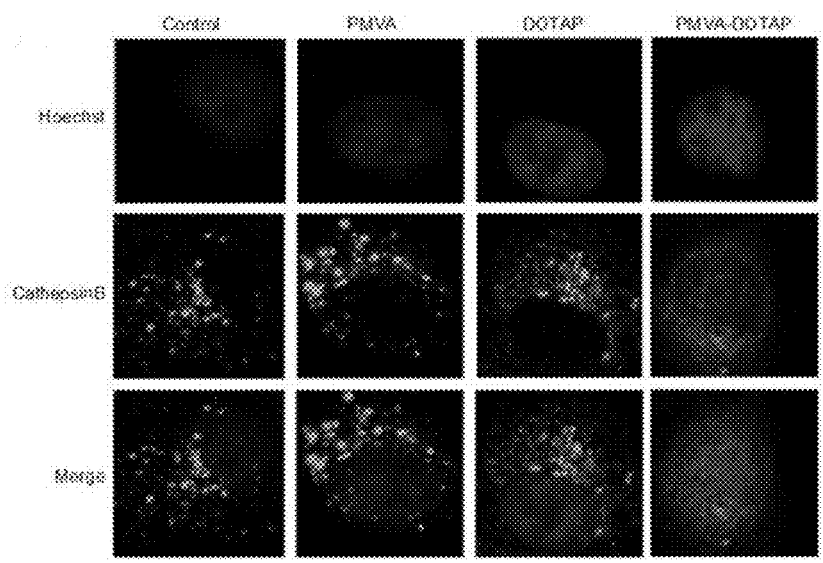

(4) Experimental Results of CathepsinB Released from Lysosomes Due to Changes in Lysosomal Membrane Permeability of A549 Cells Based on CathepsinB Intracellular Localization Method If the lysosomal membrane permeability changes, hydrolase in lysosomes will transfer to cell cytoplasm. Therefore, in order to further prove the increase of lysosomal membrane permeability, Cathepsin B in lysosomes was immunofluorescence stained and traced. As shown in FIG. 14B, Cathepsin B in the cytoplasm of A549 cells was distributed in dots in the blank control group and control groups pMVA-1 plasmid group (PMVA) and DOTAP cationic lipid group (DOTAP), while Cathepsin B in cytoplasm and nucleus was distributed dispersedly in the pMVA-1/DOTAP complex group (PMVA-DOTAP), indicating that the pMVA-1/DOTAP complex can synergistically induce the increased lysosomal membrane permeability of A549 cells and release lysosomal hydrolase into cytoplasm.

The experimental results show that after entering the tumor cells, the pMVA-1/DOTAP complex can synergistically induce the increase of lysosomal membrane permeability of cells, promote lysosomal rupture, and release hydrolase in lysosomes into cytoplasm.

Example 16 μMVA-1/DOTAP Complex Synergically Induces the Decrease of Mitochondrial Membrane Potential in Tumor Cells (1) Inoculation of tumor cells in plates: A549 cells and CT26 cells in the logarithmic growth phase were prepared into a cell suspension respectively, inoculated into a 6-well plate as per 1×10⁵ cells/well, 2 ml of medium was added to each well, and cultured overnight in a 5% $CO_2$ incubator at 37° C.

(2) Different samples added to act on tumor cells: the pMVA-1 plasmid, the DOTAP cationic lipid and the pMVA-1/DOTAP complex were added to the tumor cells cultured in Step (1) respectively, and incubated at 37° C. for 15 h, 18 h, 21 h and 24 h.

(3) Preparation of TMRM dyeing working fluid (made by Life Technologies): the TMRM mother liquor was diluted with PBS at a ratio of 1:100000 to obtain the TMRM dyeing working fluid.

(4) Discarding the cell culture fluid in Step (2), the preheated TMRM staining working fluid prepared in Step (3) was added along the wall of the hole plate, and incubated at 37° C. for 20 min in the dark.

(5) The tumor cells in Step (4) were collected and treated with different samples for different times, and the tumor cells with mitochondrial membrane potential changes were analyzed by flow cytometry.

As a potentiometric fluorescence probe, tetramethylrhodamine methyl ester (TMRM) entered the cells and was cleaved by cell lactonase to produce tetramethylrhodamine, indicating strong fluorescence after they had entered mitochondria. When the mitochondrial membrane channel pores were open, tetramethylrhodamine was released from mitochondria into cytoplasm, and its fluorescence intensity was also significantly reduced. Therefore, the open state of mitochondrial membrane channel pores can be verified by testing the changes of fluorescence intensity in mitochondria of tumor cells.

Figure 15A:
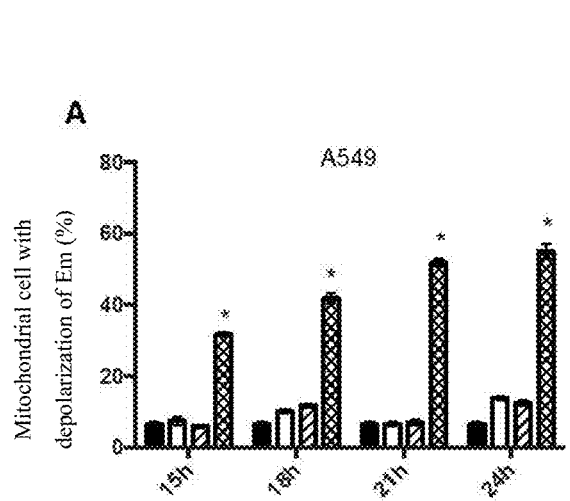
FIGS. 15A and 15B are graphs showing the determination of changes of the mitochondrial membrane potential of tumor cells by the TMRM fluorescence marker method.
Figure 15B:
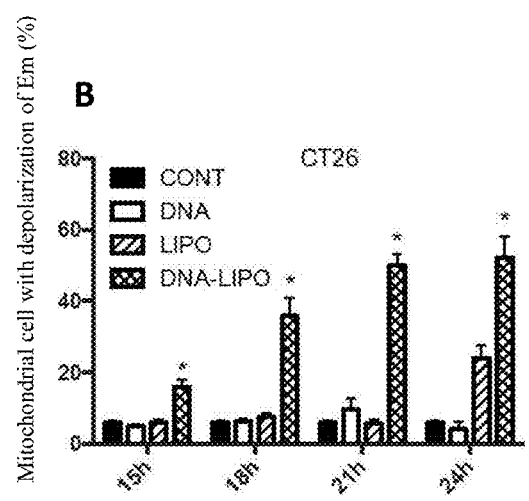

As shown in FIG. 15A, 31.73%, 41.80%, 51.76% and 55.03% of the A549 cells treated with the pMVA-1/DOTAP complex showed a decrease in mitochondrial membrane potential at 15 h, 18 h, 21 h, 24 h respectively; whereas, the mitochondrial membrane potential of A549 cells in the blank control group as well as the control groups (pMVA-1 plasmid group and DOTAP cationic lipid group) did not change significantly. As shown in FIG. 15B, 15.95%, 35.85%, 50.18% and 52.18% of the CT26 cells treated with the pMVA-1/DOTAP complex showed a decrease in mitochondrial membrane potential at 15 h, 18 h, 21 h and 24 h respectively; whereas, the mitochondrial membrane potential of CT26 cells in blank control group and control group did not change significantly.

The experimental results show that the pMVA-1/DOTAP complex can cause depolarization of mitochondrial membrane potential of tumor cells after it synergistically induces lysosomal rupture of tumor cells, thereby opening the mitochondrial membrane channel pores, significantly changing mitochondrial permeability, and releasing mitochondrial contents into cytoplasm.

Example 17 μMVA-1/DOTAP Complex Induces Caspase Protease Activation in Tumor Cells (1) Inoculation of A549 cells in plates: A549 cells in the logarithmic growth phase were prepared into a cell suspension, inoculated into a 6-well plate as per 1×10⁵ cells/well, 2 ml of medium was added to each well, and cultured overnight in a 5% CO2 incubator at 37° C.

(2) Sample loading: the pMVA-1/DOTAP complex was added to A549 cells cultured in Step (1) for 12 h and 24 h, and a blank control group was made.

(3) Preparation of test sample: pipetting the cell culture fluid obtained in Step (2), collecting A549 cells obtained in Step (2), and suspending the pipetted cell culture fluid. Collecting cells by centrifugation at 600 g and at 4° C. for 5 min, extracting the supernatant, washing the cells once with PBS and extracting the supernatant again, adding lysate, resuspending and precipitation, and lysing in an ice bath for 15 min. Then, transferring the supernatant to a centrifuge tube precooled by an ice bath.

(4) Taking a small amount of sample described in Step (3) and measuring the protein concentration by Bradford method.

(5) Detection of Caspase 3, caspase8 and caspase9 enzyme activities in the test sample prepared in Step (3) above:

a. Taking out a proper amount of substrate and placing on an ice bath for later use.

b. Creating the reaction system as shown in Table 8:

TABLE 8

Reaction system for Caspase activity assay

| | Blank control | Sample |
| --- | --- | --- |
| Test buffer | 40 μl | 40 μl |
| Test sample | 0 μl | 50 μl |
| Lysate | 50 μl | 0 μl |
| Ac-DEVD-pNA (2 mM)/ Ac-IETD-pNA (2 mM)/ Ac-LEHD-pNA (2 mM) | 10 μl | 10 μl |
| Bulk volume | 100 μl | 100 μl | c. The substrate in Step a was added to the reaction system in Step b, mixed uniformly, incubated at 37° C. for 60-120 min, so as to determine A405 in case of obvious color development.

d. The absorbance of pNA catalyzed by Caspase3, Caspase8 and Caspase9 in the sample was obtained by subtracting A405 of the blank control from A405 of the sample. The amount of pNA generated by catalysis in the sample was calculated by comparing the standard curves.

e. The protein concentration of the test sample was tested according to Bradford method in Step (3), and the enzyme activity unit of caspase contained in the protein per unit weight of the sample was calculated.

Figure 16:
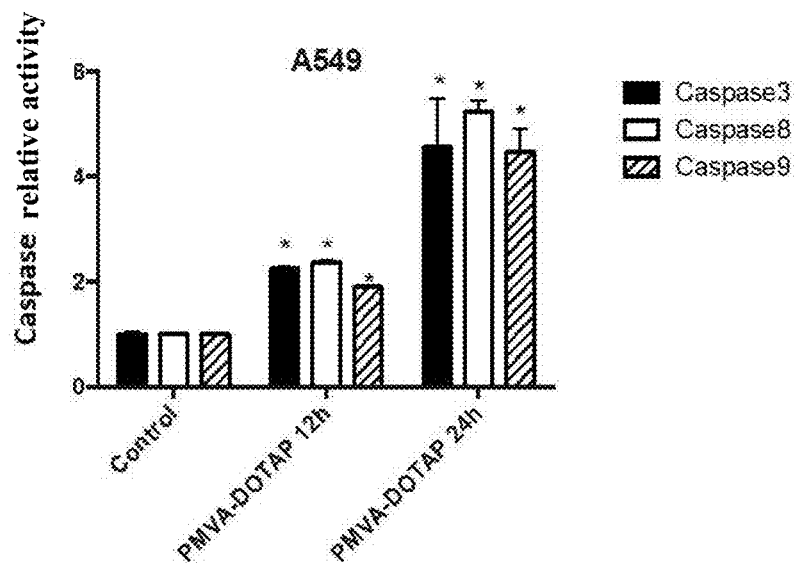
FIG. 16 is a graph showing the activation of Caspase protease in A549 cells induced by pMVA-1/DOTAP complexes. All results were expressed as mean relative expression ±SD, *P<0.05.

Cysteine-requiring Aspartate Protease (Caspase) is a protease family that plays an important role in the process of cell apoptosis. As shown in FIG. 16, compared with the blank control group, Caspase3, Caspase8 and Caspase9 all increased significantly and they were time-dependent after the cells had been treated with the pMVA-1/DOTAP complex for 12 h and 24 h.

Example 18 μMVA-1/DOTAP Complex Synergically Induces Anti-Tumor Innate Immune Response (1) Separation and Culture of Bone Marrow-Derived Dendritic Cells (BMDC) from Mouse Bone Marrow Precursor Cells a. Bone marrow cells were obtained from the femur and tibia of mouse, sieved and collected in a centrifuge tube, centrifuged at 280 g and at room temperature for 5 min, and the supernatant was discarded.

b. 10 ml of red cell lysate was added to the cells described in Step a, standing for 3 min at room temperature, centrifuged at 280 g and at room temperature for 5 min, and the supernatant was discarded.

c. The bone marrow cells described in Step b were washed twice with PRMI-1640 medium, centrifuged at 280 g and at room temperature for 10 min, live cell count was carried out, the cell concentration was adjusted to $1\times10^6$ cells/ml by RPMI-1640 complete medium.

d. In Step c, the recombinant mouse GM-CS with a final concentration of 10 ng/ml was added and 4 ml/well cell suspension was inoculated into a 6-well plate, and cultured in a 37° C., 5% $CO_2$ incubator. When cell colonies grew on the bottom of the plate, the medium was pipetted, washed once with the medium, and 1640 complete medium containing 10 ng/ml of GM-CSF was added to each well.

e. The cells separated in Step d, namely BMDC were collected, centrifuged at 280 g and at room temperature for 5 min, the supernatant was discarded, the cells were suspended in 1640 complete culture containing 10 ng/ml of GM-CSF, and the cells were inoculated into a 6 well plate as per $1\times10^6$ cells/ml for use.

(2) FITC-Dextran Uptake Test by BMDC Based on Flow Cytometry a. The BMDC cultured in Step 1 were collected and treated with the medium, pMVA-1 plasmid, DOTAP cationic lipid and pMVA-1/DOTAP complex for 24 h respectively. CT26 cell stimulation DC group (including CT26 cells, CT26 cells treated with pMVA-1 plasmid, CT26 cells treated with DOTAP cationic lipid, CT26 cells treated with pMVA-1/DOTAP complex) was made and incubated for 24 h.

b. Cells described in Step a were laid into a 24-well plate as per $1\times10^6$ cells/ml per well, FITC-Dextran with a final concentration of 1 mg/ml was added and incubated at 37° C. for 1 h.

c. The cells described in Step b were washed once with PBS, anti-CD11b-PE and anti-CD11c-Percp5.5 were added for staining the cells. The cells were washed with PBS, resuspended, and kept at 4° C. in the dark for test.

d. Test and analysis of fluorescence intensity of BMDC based on flow cytometry.

(3) Test of Cytokines Secreted by BMDC Based on Flow Cytometry a. The BMDC cultured in Step 1 to the $6^{th}$ day were collected. The medium, CT26 cells, CT26 cells treated with pMVA-1 plasmid for 3 h, CT26 cells treated with DOTAP lipid for 3 h and CT26 cells treated with pMVA-1/DOTAP complex for 3 h were added and incubated for 24 h.

b. The cells described in Step a were collected and washed once with PBS. The anti-CD11b-PE and anti-CD11c-Percp5.5 antibodies were added to the flow tube and incubated at 4° C. for 30 min in the dark.

c. The BMDC in Step b was washed twice with PBS, the indirectly labeled intercellular cytokine antibody was stained, 1 μl of antibody was added to each tube, and incubated overnight at 4° C.

d. The stained and incubated BMDC in Step c was washed twice with PBS, the indirectly labeled fluorescent secondary antibody and directly labeled antibody were stained, incubated at room temperature for 30 min in the dark and washed twice with PBS, the secretion of IFN-β and IL-1β of BMDC was tested and analyzed by flow cytometry.

Figure 17:
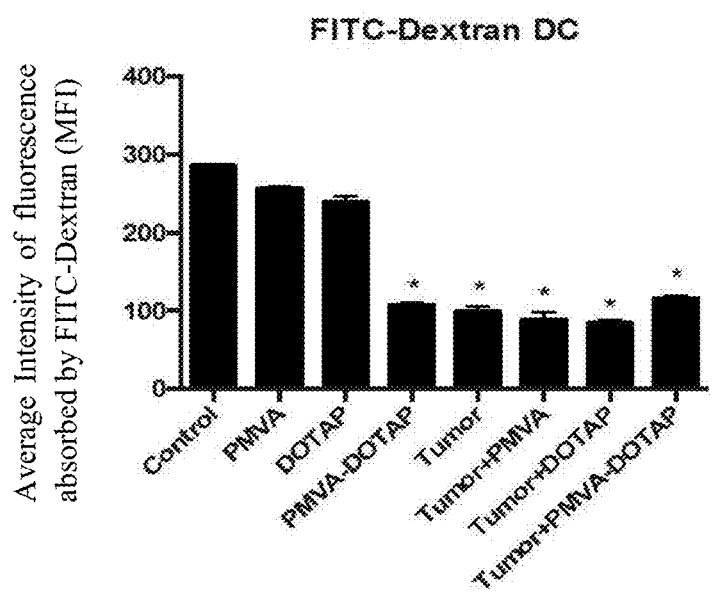
FIG. 17 is a graph showing the inhibitory effects of stimulation of pMVA-1/DOTAP complexes and tumor cells on antigen uptake of DC cells. FITC-Dextran was the model antigen taken up by DC cells. The phagocytic ability of DC cells was judged by determining the FITC mean fluorescence intensity of CD11c positive DC cells, thereby analyzing whether DC was induced to mature. *P<0.05. For the Control group (Control): only medium was added to BMDC cells, for the PMVA group: only pMVA-1 plasmids were added to BMDC cells, for the DOTAP group: only DOTAP cationic lipids were added to BMDC cells, for the PMVA- DOTAP group: only pMVA-1/DOTAP complex was added to BMDC cells; for the Tumor group: CT26 cells were added to BMDC cells, for the Tumor+PMVA group: CT26 cells treated with pMVA-1 plasmid vector were added to BMDC cells, for the Tumor+DOTAP group: CT26 cells treated with DOTAP cationic lipid were added to BMDC cells, and for the Tumor+PMVA-DOTAP group: CT26 cells treated with pMVA-1/DOTAP complex were added to BMDC cells.

DC maturation is positively correlated with the decreased antigen uptake capacity. So, whether DC is induced to mature can be judged by testing its antigen uptake capacity. DC's antigen uptake ability is judged by taking FITC-Dextran as the model antigen of DC phagocytosis, and testing the FITC average fluorescence intensity of CD11c positive DC. As shown in FIG. 17, DC treated only with pMVA-1 plasmid or DOTAP cationic lipid have similar FITC average fluorescence intensity values to that of the blank control group. For DC treated with the pMVA-1/DOTAP complex, DC stimulated by CT26 cells, and DC stimulated by CT26 cells which had been treated with pMVA-1 plasmid, DOTAP cationic lipid and pMVA-1/DOTAP complex respectively, the FITC average fluorescence intensity decreased significantly. The experimental results show that stimulation of the pMVA-1/DOTAP complex and tumor cells can inhibit the antigen uptake of DC and promote the maturation of DC.

Figure 18A:
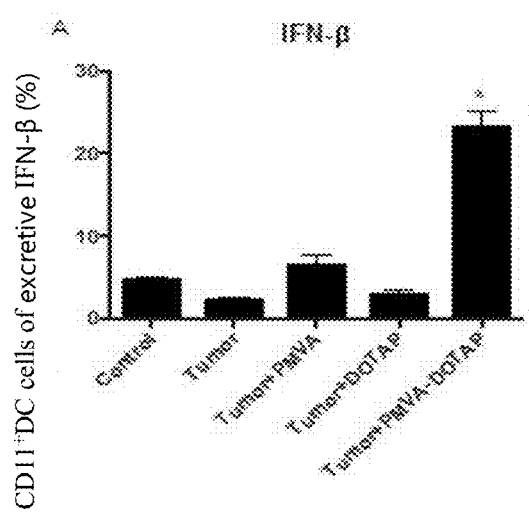
FIGS. 18A and 18B are graphs showing the statistical analysis of the percentage of BMDC cells secreting cytokines after stimulation by CT26 cells determined by flow cytometry.
Figure 18B:
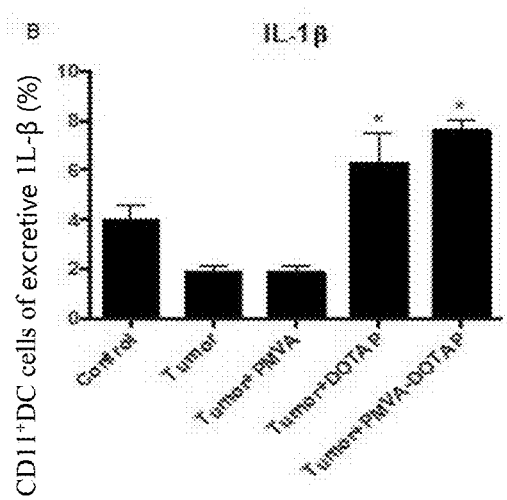
Figure 19A:
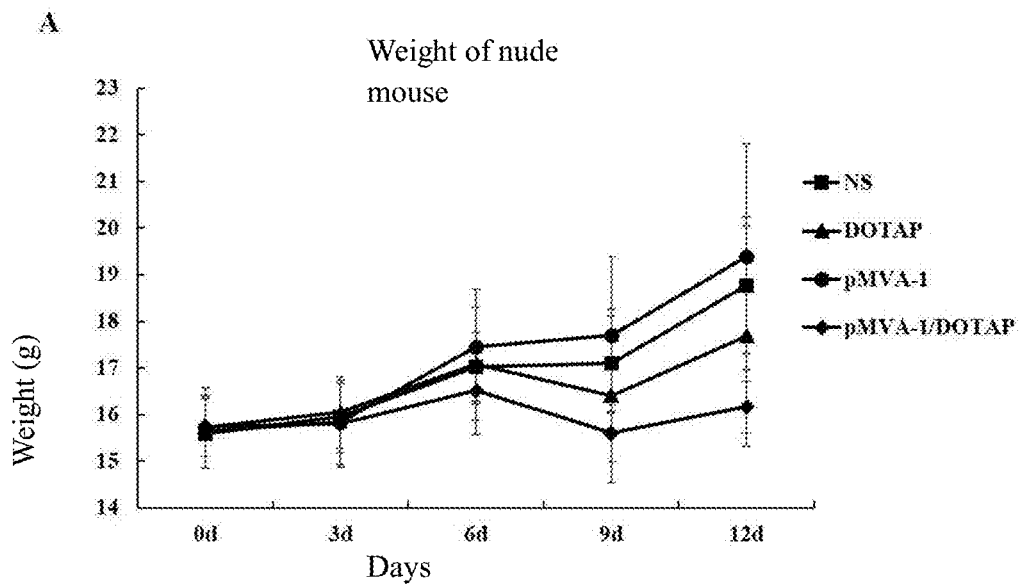
FIGS. 19A-19D are graphs showing the pMVA-1/DOTAP complex significantly inhibited tumor growth in nude mouse models with peritoneal metastasis of cervical cancer.
Figure 19B:
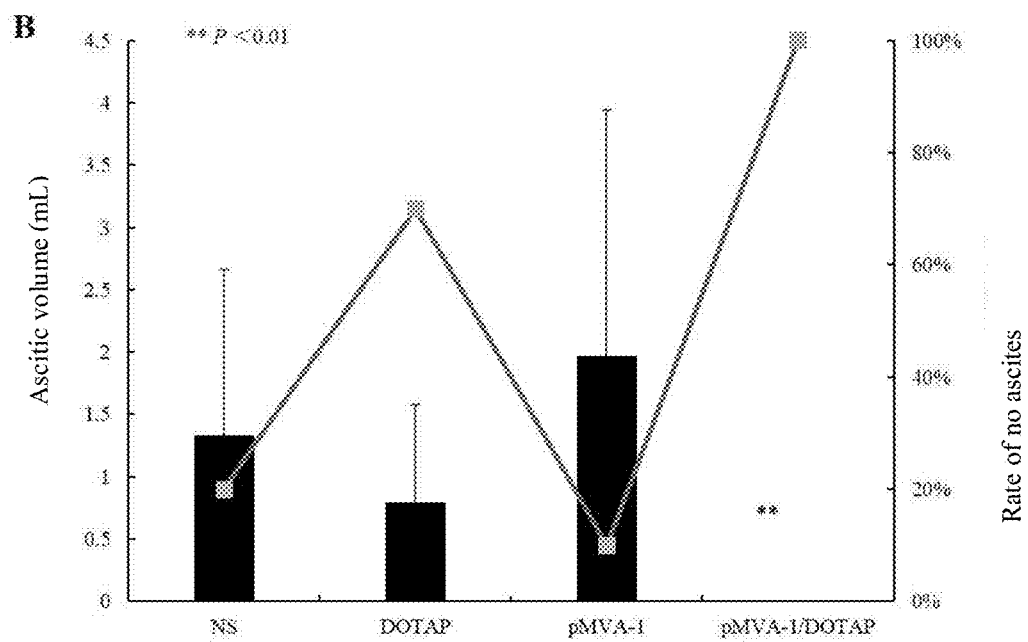
Figure 19C:
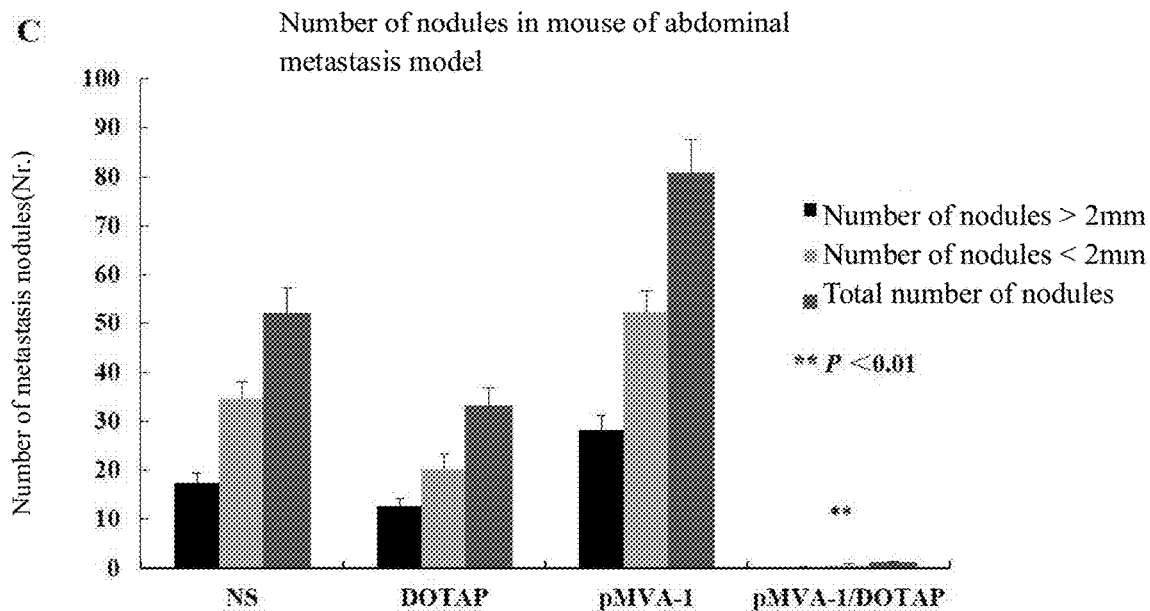
Figure 19D:
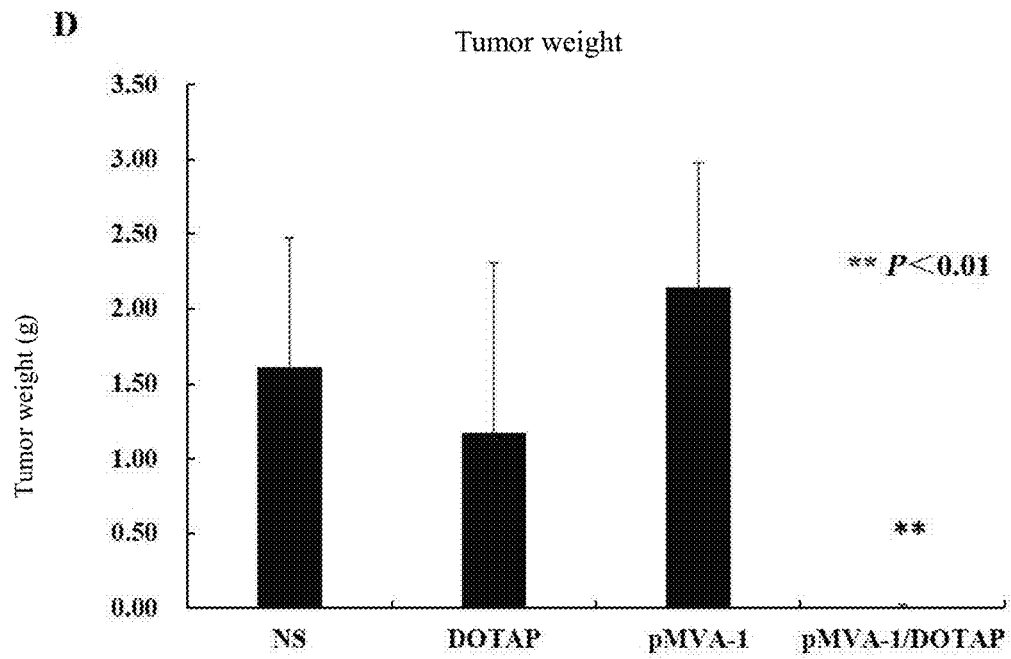

FIG. 18 provides the experimental results about whether CT26 cells treated with the pMVA-1/DOTAP complex can stimulate BMDC cultured in vitro to secrete cytokines. Based on the comparison of blank control group, pMVA-1 plasmid group and DOTAP cationic lipid group, the secretion of IFN-(3 and IL-10 significantly increased after BMDC was stimulated by CT26 cells treated with the pMVA-1/DOTAP complex. The experimental results show that tumor cells treated with the pMVA-1/DOTAP complex can effectively activate the STING pathway and induce DC to secrete cytokines that kill tumor cells.

The experimental data shows that the pMVA-1/DOTAP complex can not only directly induce the maturation of DC, but also the tumor cells treated with the pMVA-1/DOTAP complex can better activate the function of DC secreting anti-tumor cytokines to perform innate immune response.

Example 19 Experiments on Different Tumor Model of Mice Treated with DNA/Cationic Biomaterial Complex 1 μMVA-1/DOTAP complex can inhibit tumor growth of nude mice with abdominal metastasis of cervical cancer Balb/c female nude mice aged 6-8 weeks were raised. Human cervical cancer Hela cells cultured to the logarithmic growth phase were prepared into a cell suspension, and the nude mice with abdominal metastasis of cervical cancer were modeled by intraperitoneal injection. The number of cells injected into each nude mouse was $1\times10^7$, and the injection system was 200 μl for each nude mouse.

The nude mice that had been successfully modeled were randomly divided into 4 groups as described in Table 9, i.e. normal saline group (NS), DOTAP group (empty vector group), pMVA-1 group (empty drug group) and pMVA-1/DOTAP group (treatment group). On the $3^{rd}$ day after inoculation of Hela cells, each experimental group was intraperitoneally administrated every 3 days separately according to Table 9, and the body weight of each experimental group was recorded. After intraperitoneal administration for 4 times, that is, on 12 d, one nude mouse in control group (pMVA-1) died, and all the other 3 groups of nude mice except the treatment group existed obvious ascites, and all nude mice were killed. Ascites of nude mice were taken to measure its volume and count the number of cancer cells. The apoptotic cells in ascites were tested by flow cytometry, and ascites cells were observed by Giemsa staining. The tumor was removed and its weight was weighed. Tumor, tissues and organs were fixed with paraformaldehyde and then immunohistochemistry tested.

TABLE 9

Grouping and dosage of administration of nude mice with abdominal metastasis of cervical cancer treated with pMVA-1/DOTAP complex

| Group | | Number of mice (Nr.) | Dosage of administration | |
|---|---|---|---|---|
| | | | pMVA-1 (μg/mouse) | DOTAP (μg/mouse) |
| Negative control group | NS | 10 | — | — |
| Lipid material control group | DOTAP | 10 | — | 100 |
| Plasmid DNA control group | pMVA-1 | 10 | 10 | — |
| Treatment group | pMVA-1/DOTAP | 10 | 10 | 100 |

Figure 20:
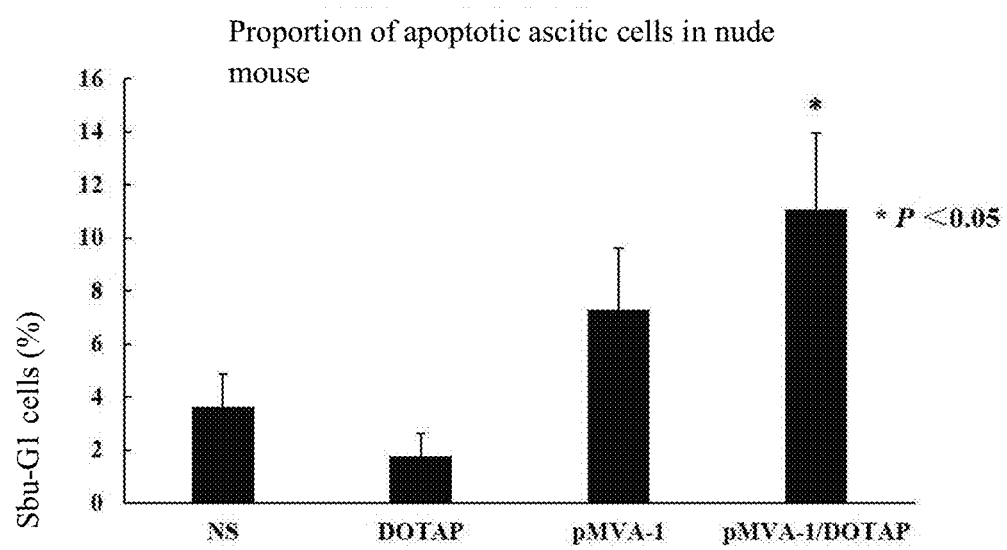
FIG. 20. is a statistical analysis chart of the percentage of apoptotic cells in ascites of nude mouse models with peritoneal metastasis of cervical cancer determined by flow cytometry.

FIG. 19 provides the experimental results as follows: weight (FIG. 19A), ascites volume (FIG. 19B), number of tumor nodules (FIG. 19C) and tumor weight (FIG. 19D) of nude mice in pMVA-1/DOTAP treatment group are significantly lower than those in other control groups (P<0.01). As shown in FIG. 20, the percentage of apoptotic cells in ascites in the treatment group was significantly higher than that in other control groups (p<0.05). In addition, HE staining results of tumor tissue sections showed that there was a large amount of inflammatory cell infiltration in tumor tissue of the treatment group, while there was no or a little inflammatory cell infiltration in other control groups. The Giemsa staining of the cells in ascites revealed that the pMVA-1/DOTAP complex significantly inhibited the generation of tumor cells and red blood cells in abdominal cavity of nude mice, compared with the control group. HE staining of heart, liver, spleen, lung and kidney of nude mice indicated that there was no treatment-related tissue lesion in each group of nude mice. Thus, it can be considered that the pMVA-1/DOTAP complex may have better biological safety.

Thus, compared with the control groups, the pMVA-1/DOTAP complex can directly induce apoptosis of cervical cancer cells through innate immune response, and significantly inhibit the growth of cervical cancer cells.

2 Plasmid DNA/DOTAP complex can inhibit tumor growth of nude mice with abdominal metastasis of ovarian cancer.

Balb/c nude mice aged 6-8 weeks were raised. The human ovarian cancer cell line SKOV3 cultured to the logarithmic growth phase was prepared into a cell suspension, and the mice with abdominal tumor were modeled by intraperitoneal injection. The number of cells injected into each mouse was $1\times10^7$, and the injection system was 200 μl for each mouse.

The nude mice that had been successfully modeled were randomly divided into 8 groups as described in Table 10. Intraperitoneal administration began 2 days after tumor inoculation as follows: 10 μg of plasmid for each mouse in the control group of the plasmid DNA group; 100 μg of DOTAP for each mouse in the control group of the DOTAP group; 10 μg of DNA and 100 μg of DOTAP for each mouse in the treatment group (plasmid DNA/DOTAP complex group), i.e. the mass ratio of plasmid DNA to DOTAP was 1:10. After that, mice were administered every three days. All the mice were killed on the $35^{th}$ day after inoculation of the tumor, with a total of 10 times of administration.

TABLE 10

Grouping and dosage of administration of nude mice with abdominal metastasis of cervical cancer treated with plasmid DNA/DOTAP complex

| Group | | Number of mice | Dosage of administration | |
|---|---|---|---|---|
| | | | Plasmid DNA (μg) | DOTAP (μg) |
| Negative control group | Normal saline (NS) | 6 | — | — |
| Lipid material control group | DOTAP | 6 | — | 100 |
| Plasmid DNA control group | pMVA-1 | 5 | 10 | — |
| | pMVA-2 | 5 | 10 | — |
| | pMVA-3 | 5 | 10 | — |
| Treatment group | pMVA-1/DOTAP | 6 | 10 | 100 |
| | pMVA-2/DOTAP | 6 | 10 | 100 |
| | pMVA-3/DOTAP | 6 | 10 | 100 |

After intraperitoneal administration for 10 times, only one mouse in negative control group died naturally and all mice in other experimental groups were killed. Ascites of mice were taken to measure its volume and count the amount of cancer cells there.

Figure 21A:
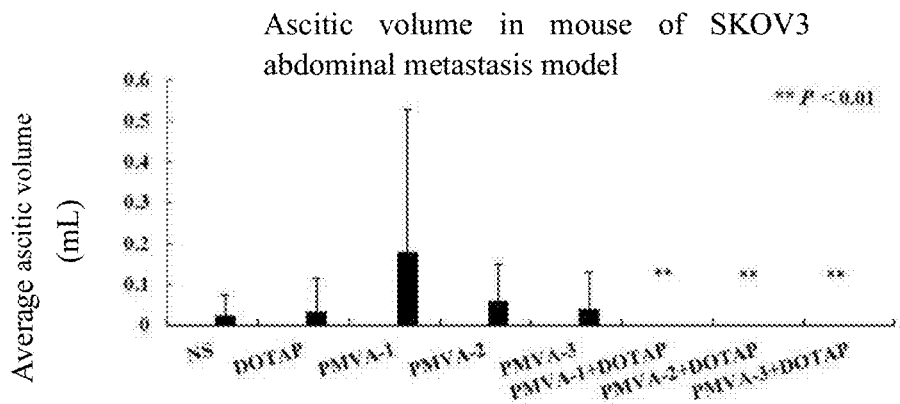
FIGS. 21A-21C are graphs showing the DNA/DOTAP complex inhibited tumor growth in model mice with peritoneal metastasis of ovarian cancer.
Figure 21B:
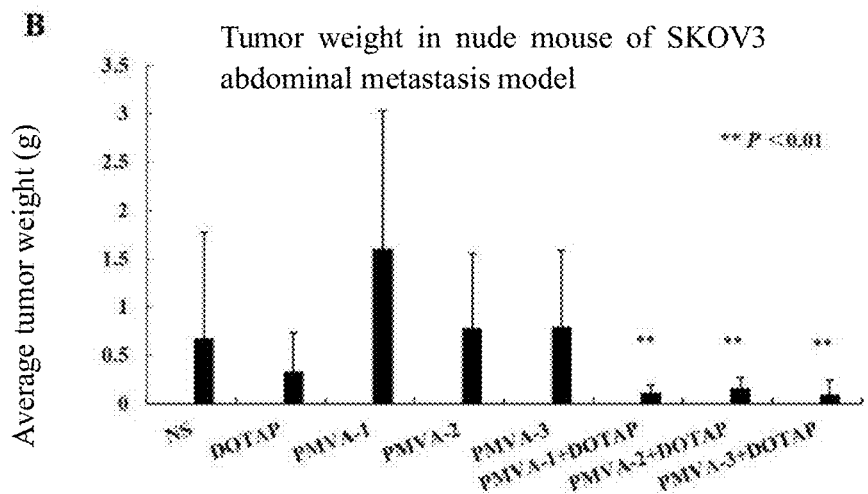
Figure 21C:
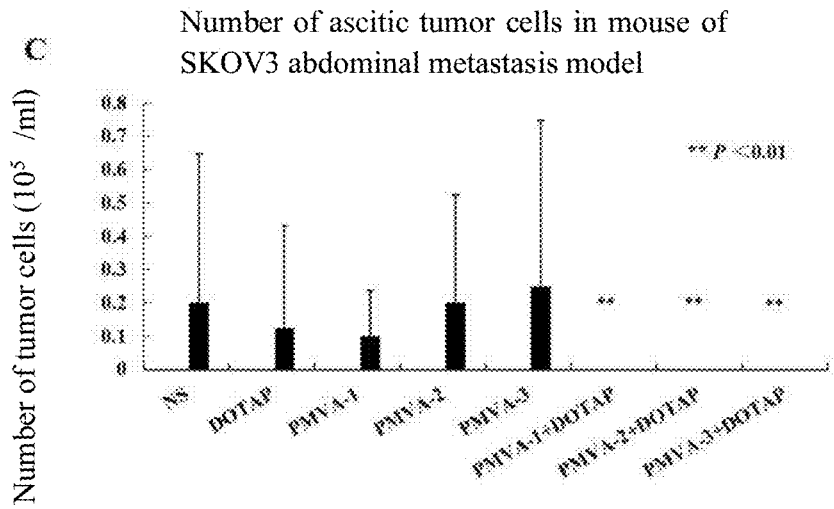
Figure 22A:
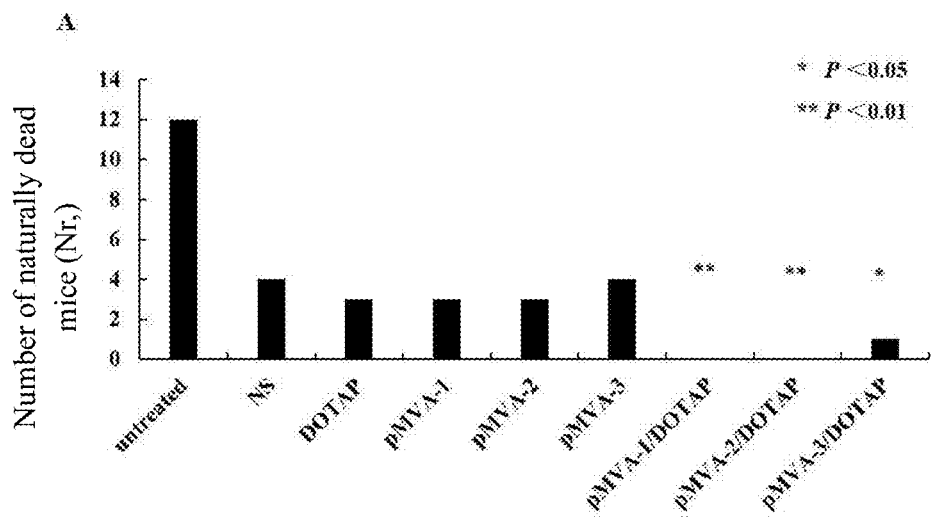
FIGS. 22A-22E are graphs showing the plasmid DNA/DOTAP complex inhibited tumor growth in model mice with peritoneal metastasis of CT26.
Figure 22B:
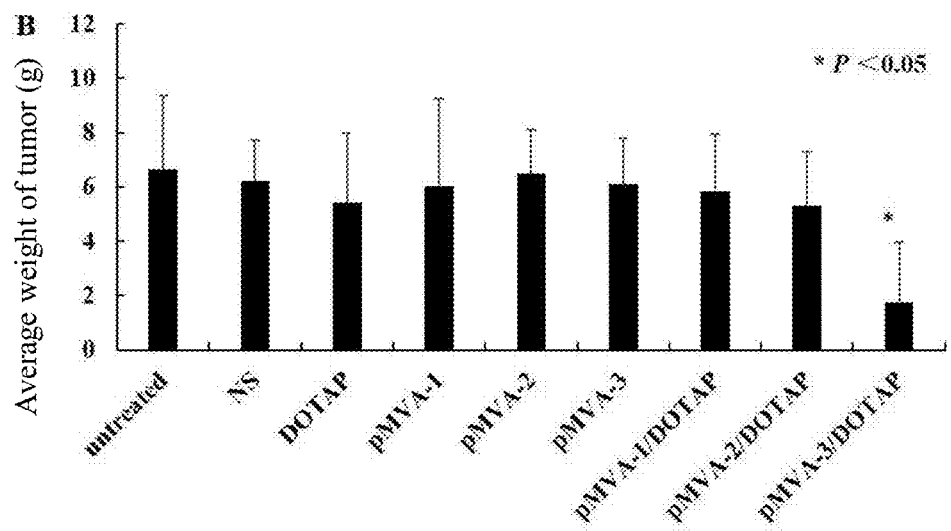
Figure 22C:
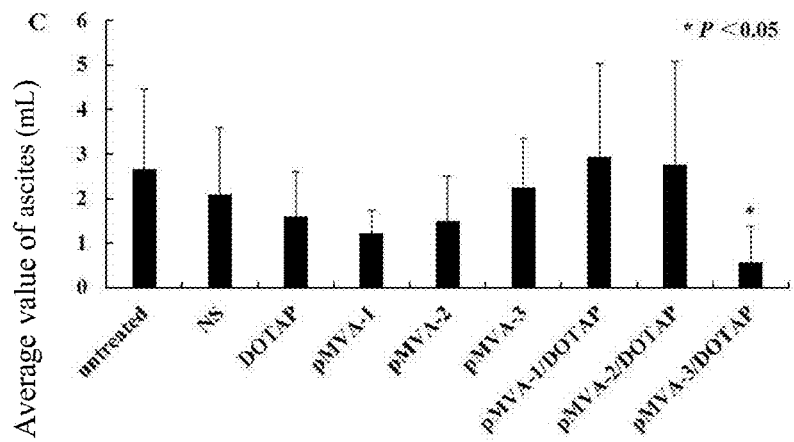
Figure 22D:
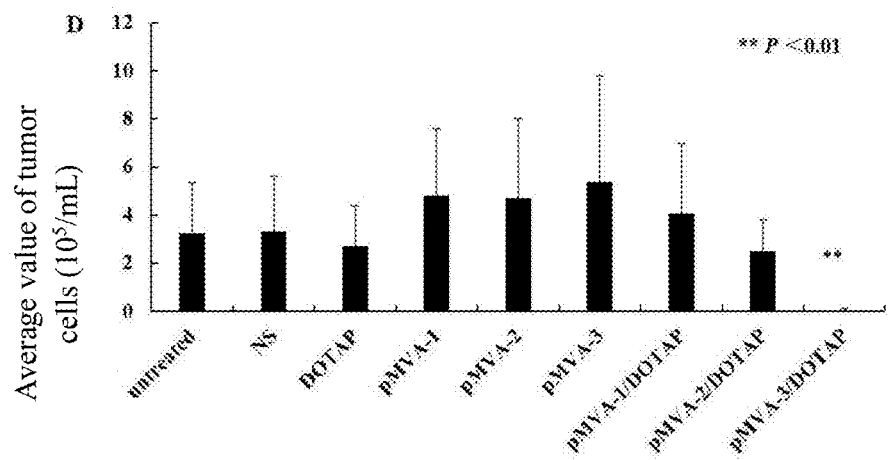
Figure 22E:
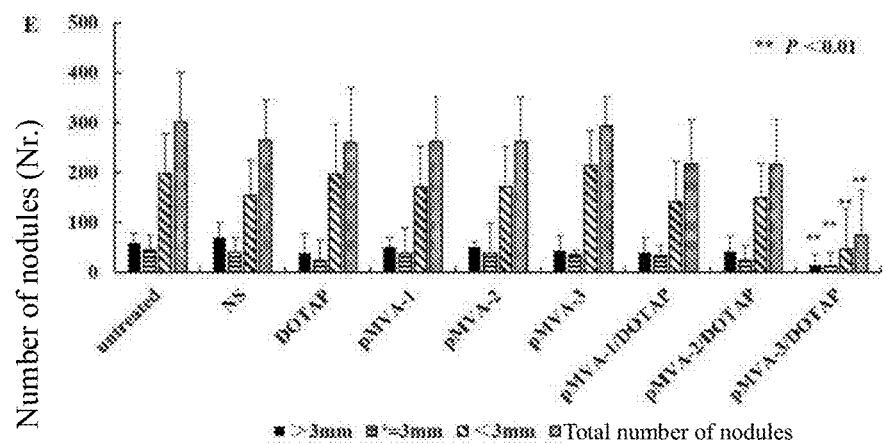

FIG. 21 provides the experimental results as follows: the ascites volume (FIG. 21A), tumor weight (FIG. 21B) and the number of ascites cancer cells (FIG. 21C) of nude mice administrated with plasmid DNA/DOTAP in the three treatment groups were significantly lower than those in other control groups (p<0.01).

Therefore, compared with the control groups, the plasmid DNA/DOTAP complex in the treatment group can directly induce ovarian cancer cell apoptosis through innate immune response, and can significantly inhibit the growth of ovarian cancer cells.

3 Plasmid DNA/DOTAP complex can inhibit tumor growth of mice with CT26 abdominal metastasis Balb/c mice aged 6-8 weeks were raised. The mouse colon cancer cell line CT26 cultured to the logarithmic growth phase was prepared into a cell suspension, and the mice with abdominal tumor were modeled by intraperitoneal injection. The number of cells injected into each mouse was $1\times10^6$, and the injection system was 100 μl for each mouse.

The mice that had been successfully modeled were divided into groups as described in Table 11. They were intraperitoneally administrated on the $5^{th}$ day after inoculation of the tumor as follows: 10 μg of DNA for each mouse in the control group of the plasmid DNA group; 100 μg of DOTAP for each mouse in the DOTAP control group; 10 μg of DNA and 100 μg of DOTAP for each mouse in the treatment group of plasmid DNA/DOTAP complex group, i.e. the mass ratio of plasmid DNA to DOTAP was 1:10. After that, they were administered every three days for a total of 5 times.

TABLE 11

Grouping and dosage of administration of model
mice with abdominal metastasis of CT26 colon
cancer treated with plasmid DNA/DOTAP complex

| Group | | Number of mice (Nr.) | Dosage of administration | |
|---|---|---|---|---|
| | | | Plasmid DNA (µg) | DOTAP (µg) |
| Blank control group | Untreated | 22 | — | — |
| Negative control group | Normal saline (NS) | 10 | — | — |
| Lipid material control group | DOTAP | 10 | — | 100 |
| Plasmid DNA control group | pMVA-1 | 10 | 10 | — |
| | pMVA-2 | 10 | 10 | — |
| | pMVA-3 | 10 | 10 | — |
| Treatment group | pMVA-1/DOTAP | 10 | 10 | 100 |
| | pMVA-2/DOTAP | 10 | 10 | 100 |
| | pMVA-3/DOTAP | 10 | 10 | 100 |

Mice were intraperitoneally administered for 5 times, and 2 mice in each group were killed on the $2^{nd}$ day after the $3^{rd}$ administration, i.e. the $13^{th}$ day after inoculation of the tumor. On the $1^{st}$ day after the fourth administration, that is, on the $15^{th}$ day after inoculation of the tumor, 3 mice in each group were killed. On the $4^{th}$ day after the fifth administration, i.e. 21 days after inoculation of the tumor, 5 mice in each group were killed. Ascites of mice were taken to measure its volume and count the number of ascites cancer cells. Apoptotic cells in ascites were tested by flow cytometry. The tumor was removed and weighed. Tumors, tissues and organs were fixed with paraformaldehyde and then immunohistochemistry tested. The rest of the mice were allowed to die naturally, and tumor-free statistics were carried out.

FIG. 22 provides the experimental results as follows: the number of natural deaths of mice in the three plasmid DNA/DOTAP treatment groups was significantly lower than that in other control groups ($p<0.01$ or $p<0.05$) (FIG. 22A); the tumor weight (FIG. 22B), ascites volume (FIG. 22C), number of ascites cancer cells (FIG. 22D), and number of tumor nodules (FIG. 22E) of mice in the pMVA-3/DOTAP treatment group were significantly lower than those in other control groups ($p<0.01$ or $p<0.05$).

Therefore, compared with the control groups, the plasmid DNA/DOTAP complex in the treatment group inhibits the growth of colorectal cancer CT26 cells.

4 µMVA-1/DOTAP complex can inhibit the growth of sarcoma in mice.

KM mice aged 6-8 weeks were raised. The mouse sarcoma cell line S180 cultured to the logarithmic growth phase was prepared into a cell suspension, and mouse subcutaneous tumor was modeled by subcutaneous injection in the right axilla of each mouse. The number of cells injected into each mouse was $1\times10^7$, and the injection system was 200 µl for each mouse.

On the $5^{th}$ day after inoculation of S180 sarcoma cells, when the tumor could be palpated, 40 tumor-bearing mice were randomly divided into 4 groups according to Table 12: i.e. negative control group (NS), DOTAP control group, pMVA-1 control group, and treatment group pMVA-1/DOTAP group. Then, the mice were subcutaneously administrated according to Table 12: 2.5 µg of plasmid pMVA-1 for each mouse in the pMVA-1 control group; 25 µg of DOTAP for each mouse in DOTAP control group; 2.5 µg of DNA and 25 µg of DOTAP for each mouse in the treatment group of the pMVA-1/DOTAP complex group; that is, the mass ratio of plasmid DNA to DOTAP was 1:10. After that, they were administered every three days for a total of 5 times. The mice were killed and the tumor-free rate of the mice was counted 21 days after inoculation of the tumor.

TABLE 12

Grouping and dosage of administration of subcutaneous model of
mice with S180 sarcoma cells treated with pMVA-1/DOTAP complex

| Group | | Number of mice (Nr.) | Dosage of administration | |
|---|---|---|---|---|
| | | | pMVA-1 (µg/mouse) | DOTAP (µg/mouse) |
| Negative control group | NS | 10 | — | — |
| Lipid material control group | DOTAP | 10 | — | 25 |
| Plasmid DNA control group | pMVA-1 | 10 | 2.5 | — |
| Treatment group | pMVA-1/DOTAP | 10 | 2.5 | 25 |

Figure 23:
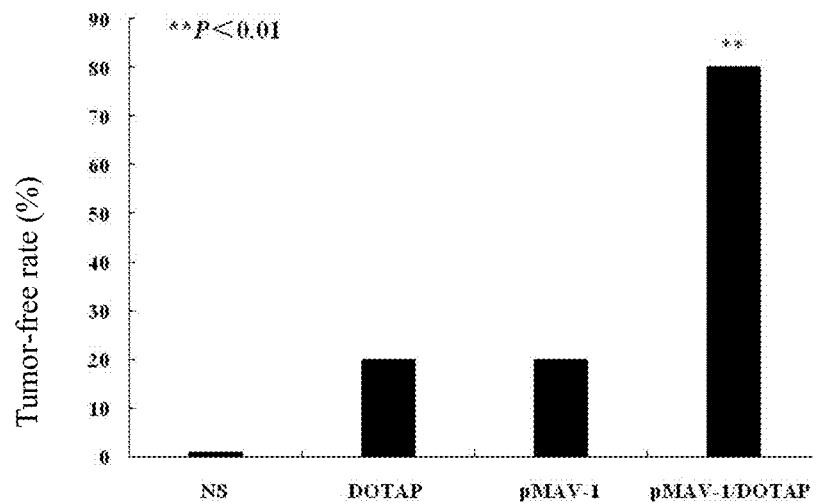
FIG. 23 is a graph showing the pMVA-1/DOTAP complex significantly inhibited the growth of sarcoma in mice. The tumor-free rate of mice in pMVA-1/DOTAP treatment group was 90%, which was significantly higher than 1% of NS group, 20% of DOTAP group and 20% of pMVA-1 group. P<0.01.

As shown in FIG. 23, the experiment results indicate that the tumor-free rate of mice in the pMVA-1/DOTAP treatment group is 90%, which is significantly higher than that of other control groups; the tumor-free rate of NS group is 1%, and that of DOTAP group and pMVA-1 group is 20%.

It can be seen that pMVA-1/DOTAP complex could significantly inhibit the growth of sarcoma in mice.

5 µMVA-1/DOTAP complex could inhibit the growth of nasopharyngeal carcinoma in mice.

Balb/c nude mice aged 6-8 weeks were raised. The human nasopharyngeal carcinoma cell line CNE-2 cultured to the logarithmic growth phase was prepared into a cell suspension. mouse subcutaneous tumor was modeled by subcutaneous injection in the right axilla of each mouse. The number of cells injected into each mouse was $1\times10^7$, and the injection system was 200 µl for each mouse.

The nude mice that had been successfully modeled were randomly divided into 4 groups as described in Table 13. When the tumor could be palpated five days after inoculation of the tumor, mice were subcutaneously administered as follows: 4 µg of plasmid for each mouse in the control group of pMVA-1 group; 40 µg of DOTAP for each mouse in the control group of DOTAP group; 4 µg of plasmid DNA and 40 µg of DOTAP for each mouse in the treatment group of pMVA-1/DOTAP complex group, i.e. the mass ratio of plasmid DNA to DOTAP was 1:10. After that, the mice were administrated every three days, all the mice were killed on the 21st day after inoculation of the tumor, and the tumor volume of the mice in each group was measured after administration for five times.

TABLE 13

Grouping and dosage of administration of subcutaneous model
mice with CNE-2 cells treated with pMVA-1/DOTAP complex

| Group | | Number of mice (Nr.) | Dosage of administration | |
|---|---|---|---|---|
| | | | pMVA-1 (μg/mouse) | DOTAP (μg/mouse) |
| Negative control group | NS | 10 | — | — |
| Lipid material control group | DOTAP | 10 | — | 40 |
| Plasmid DNA control group | pMVA-1 | 10 | 4 | — |
| Treatment group | pMVA-1/DOTAP | 10 | 4 | 40 |

Figure 24:
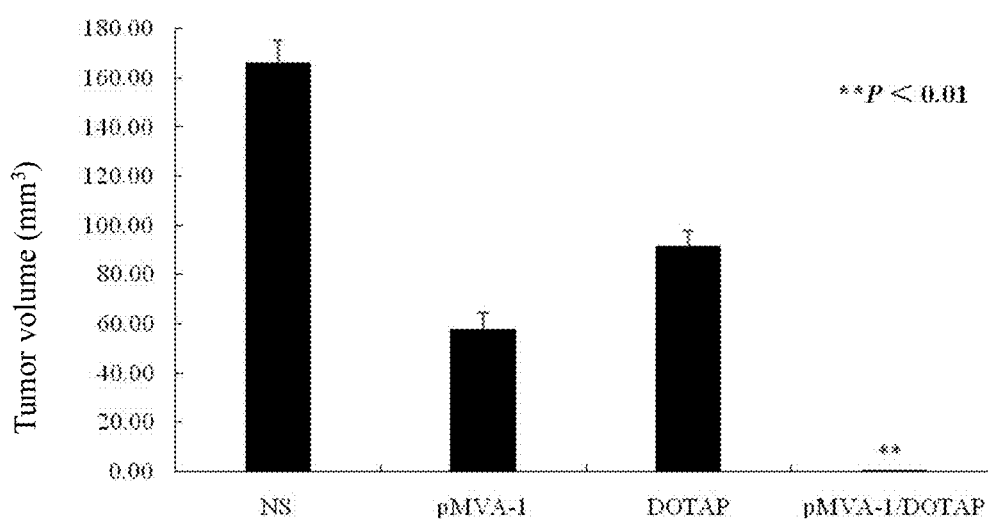
FIG. 24 is a graph showing the pMVA-1/DOTAP complex significantly inhibited tumor growth in subcutaneous model mice with human nasopharyngeal carcinoma cells. P<0.01.

As shown in FIG. 24, the experimental results show that the tumor volume of mice in the pMVA-1/DOTAP treatment group is significantly lower than that of other control groups, indicating that the pMVA-1/DOTAP complex can significantly inhibit the tumor growth of subcutaneous model mice of human nasopharyngeal carcinoma cells.

6 Long-term immune response of mice with CT26 abdominal metastasis activated by DNA/DOTAP complex Experiment (1): Model Mice with Abdominal
Metastasis of CT26 Treated with Plasmid
DNA/DOTAP Complex Balb/c mice aged 6-8 weeks were raised. The mouse colorectal cancer cell line CT26 cultured to the logarithmic growth phase was prepared into a cell suspension, and mouse abdominal tumor was modeled by intraperitoneal injection. The number of cells injected into each mouse was $2 \times 10^5$, and the injection system was 100 μl for each mouse.

As described in Table 14, the mice that had been successfully modeled were divided into groups as follows: Normal group was not inoculated with tumor cell nor administrated with drugs; untreated group was intraperitoneally inoculated with CT26 cells instead of drugs; NS group was intraperitoneally inoculated with tumor cells and administrated with normal saline. After inoculation of the tumor, mice were intraperitoneally administrated on the $3^{rd}$ day as follows: 15 μg of plasmid DNA and 75 μg of DOTAP for each mouse in the treatment group of plasmid DNA/DOTAP complex group; i.e. the mass ratio of plasmid DNA to DOTAP was 1:5. After that, they were administrated every three days for a total of 9 times.

TABLE 14

Grouping and dosage of administration of model
mice with abdominal metastasis of CT26 colorectal
cancer treated with plasmid DNA/DOTAP complex

| Group | | Number of mice (Nr.) | Dosage of administration | |
|---|---|---|---|---|
| | | | Plasmid DNA (μg) | DOTAP (μg) |
| Normal control group | Normal | 16 | — | — |
| Negative control group | Normal saline (NS) | 17 | — | — |
| DOTAP control group | DOTAP | 16 | — | 75 |

TABLE 14-continued

Grouping and dosage of administration of model
mice with abdominal metastasis of CT26 colorectal
cancer treated with plasmid DNA/DOTAP complex

| Group | | Number of mice (Nr.) | Dosage of administration | |
|---|---|---|---|---|
| | | | Plasmid DNA (μg) | DOTAP (μg) |
| Plasmid DNA control group | pMVA-1 | 16 | 15 | — |
| Treatment group | pMVA-1/DOTAP | 37 | 15 | 75 |

The mice were administrated for 9 times in total and allowed to die naturally. The natural death dates of the mice in each experimental group were recorded, and the body weight and survival time of the mice in each experimental group were counted. The volume of ascites were counted, tumors were removed and weighed.

Figure 25A:
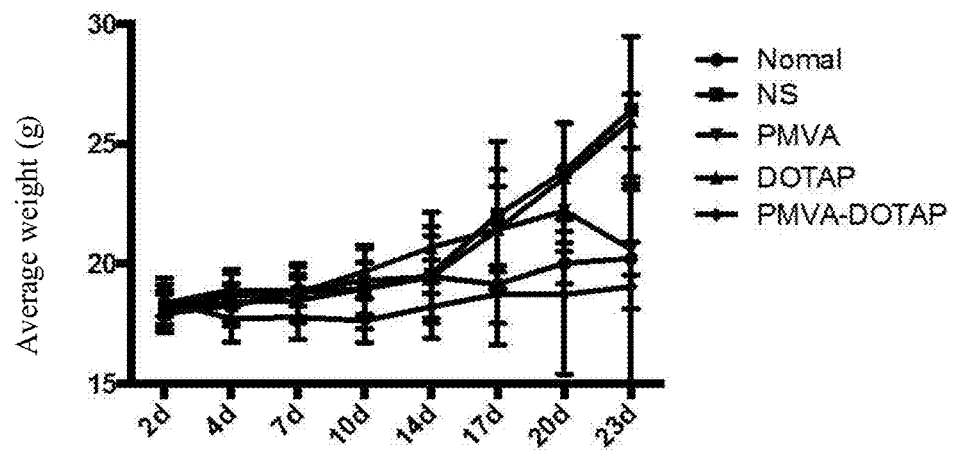
FIGS. 25A-25D are graphs showing the pVMA-1/DOTAP complex inhibited tumor growth in model mice with peritoneal metastasis of CT26.
Figure 25B:
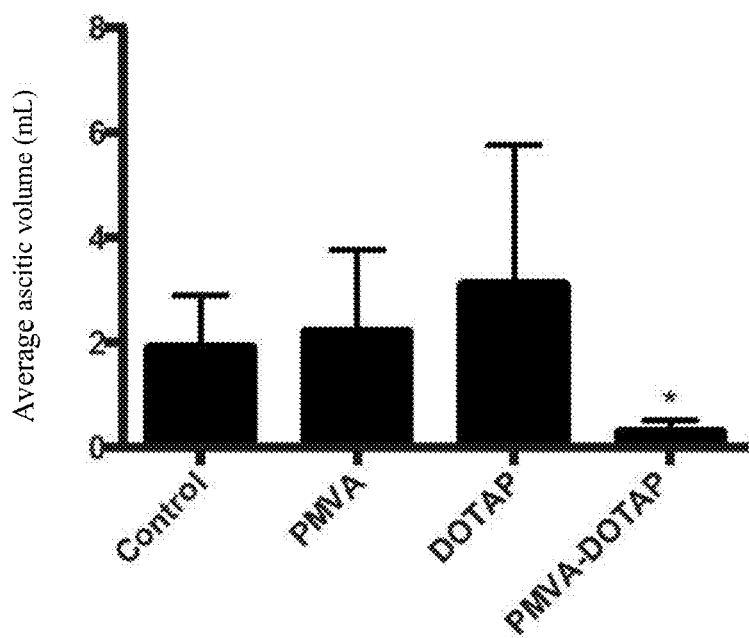
Figure 25C:
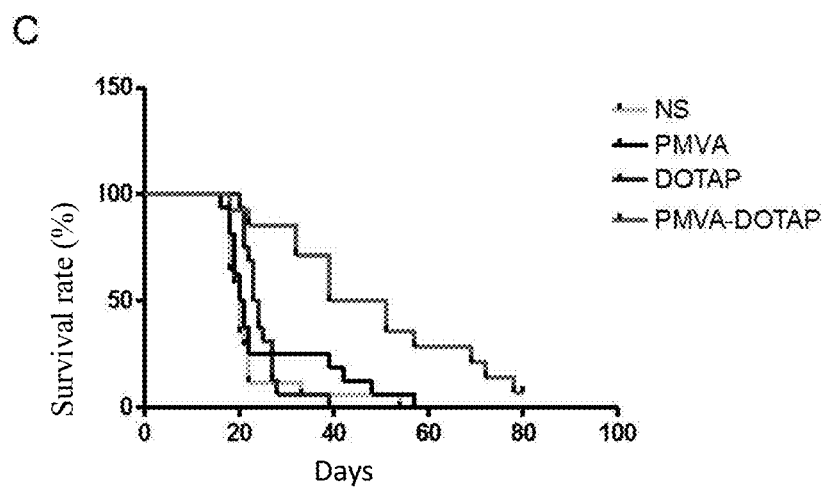
Figure 25D:
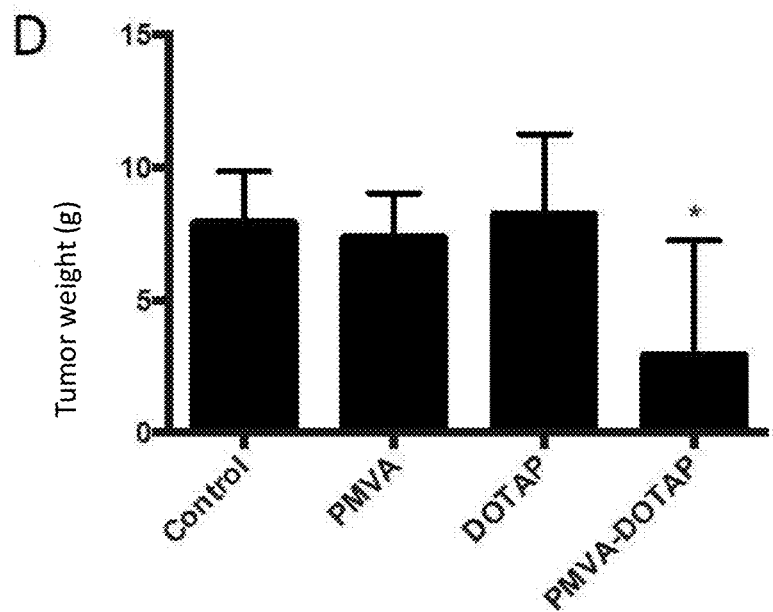

As shown in FIG. 25, the experimental results show that the weight of mice in the pMVA-1/DOTAP treatment group is not significantly different from that of mice in the normal group, indicating that the pMVA-1/DOTAP complex has no obvious toxicity to mice (FIG. 25a); moreover, the average ascites volume of mice in the pMVA-1/DOTAP group was 0.3 ml, which was significantly lower than the average ascites volume of mice in the negative control group of 1.91 ml, the average ascites volume of mice in the pMVA-1 group of 2.22 ml and the average ascites volume of mice in the DOTAP group of 3.11 ml (FIG. 25B). The negative control group, pMVA-1 group and DOTAP group all died on the $54^{th}$, $57^{th}$ and $39^{th}$ days after inoculation of the tumor cells, and some of mice in the pMVA-1/DOTAP group still survived on the $78^{th}$ day after inoculation of the tumor cells. The survival time of mice in the pMVA-1/DOTAP group was significantly longer than that in other experimental groups (FIG. 25C). Abdominal tumor was taken and weighed after the mice died. The average tumor weight of mice was 2.92 g in the pMVA-1/DOTAP group, 7.91 g in the negative control group, 7.35 g in the pMVA-1 group, and 8.23 g in the DOTAP group. The tumor weight of mice in the pMVA-1/DOTAP group was significantly reduced (FIG. 25 D) compared with the negative control group, pMVA-1 group and DOTAP group.

Thus, it can be seen that the pMVA-1/DOTAP complex can significantly inhibit the growth of tumor cells in vivo.

Experiment (2): Long-Term Immune Response to
Tumor Cell Re-Stimulation of Model Mice with
Abdominal Metastasis of CT26 after Treatment
with Plasmid DNA/DOTAP Complex For the above experiment (1), abdominal tumors of 27 mice in the treatment group of pMVA-1/DOTAP were completely eliminated after administration for 9 times, and the 27 mice were regrouped as described in Table 15. In addition, 14 mice in the same batch of Normal group were selected and grouped according to Table 15. In the above experiment (1), on the $2^{nd}$ day after the $9^{th}$ administration, the mice were subcutaneously inoculated with $1 \times 10^6$ of colorectal cancer cells CT26 and $1 \times 10^6$ mice breast cancer cells 4T1 respectively according to the grouping conditions in Table 15. The subcutaneous tumor volume of mice in each group was measured every 3 days. The tumor volume was calculated according to the following formula: $V = a \times b^2 \times 0.52$, wherein, a is the long diameter of the tumor and b is the short diameter of the tumor.

TABLE 15

Long-term immune response experiment group and subcutaneous inoculation of tumor cells

| First treatment group | Immune model group | Number of mice (Nr.) | Tumor cells subcutaneously inoculated | |
|---|---|---|---|---|
| | | | CT26 cells | 4T1 cells |
| Normal | Control group 1 | 7 | 1 × 10$^6$/mouse | — |
| | Control group 2 | 7 | — | 1 × 10$^6$/mouse |
| pMVA-1/DOTAP | Control group | 9 | — | — |
| | Treatment group 1 | 9 | 1 × 10$^6$/mouse | — |
| | Treatment group 2 | 9 | — | 1 × 10$^6$/mouse |

Figure 26A:
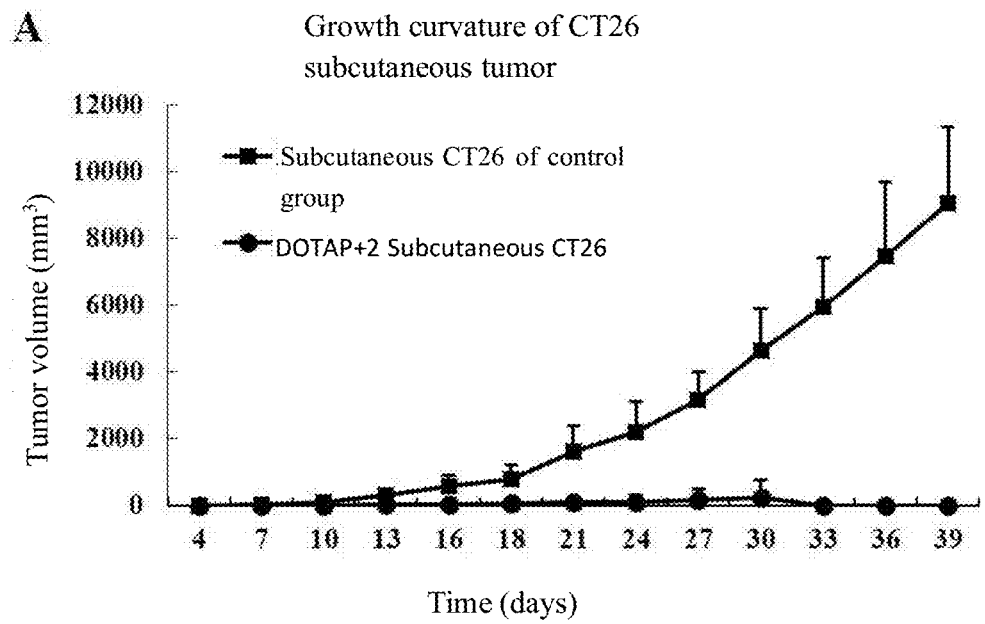
FIGS. 26A and 26B are graphs showing the pMVA-1/DOTAP complex can induce the mice to generate systemic anti-tumor memory immune response after treating model mice with peritoneal metastasis of CT26. Under further stimulation of tumor cells, including tumor cells of the same type and different types, the growth of tumor cells can be inhibited through memory T cells and a large amount of immune cytokines secreted by the memory T cells so as to break the immune tolerance of tumors.

According to the above experiments (1) and (2), the anti-CT26 colorectal cancer effect of the model mice with abdominal metastasis of CT26 was more than 90% after treated with the pMVA-1/DOTAP complex. The mice in the treatment group were subcutaneously inoculated with colon cancer CT26 cells and breast cancer 4T1 cells respectively, so as to observe the growth of CT26 subcutaneous tumor and 4T1 subcutaneous tumor. The same batch of normal mice (Normal group) was divided into two groups, which were inoculated with the same tumor as a control group respectively. The experimental results are shown in FIG. 26.

(1) After the mice were treated with the plasmid DNA/DOTAP complex, the growth of CT26 subcutaneous tumor in mice was significantly inhibited, and the mice in CT26 subcutaneous tumor experimental group were almost tumor-free (FIG. 26A), and the survival time of mice in treatment group was significantly prolonged compared with that in the control groups.

Figure 26B:
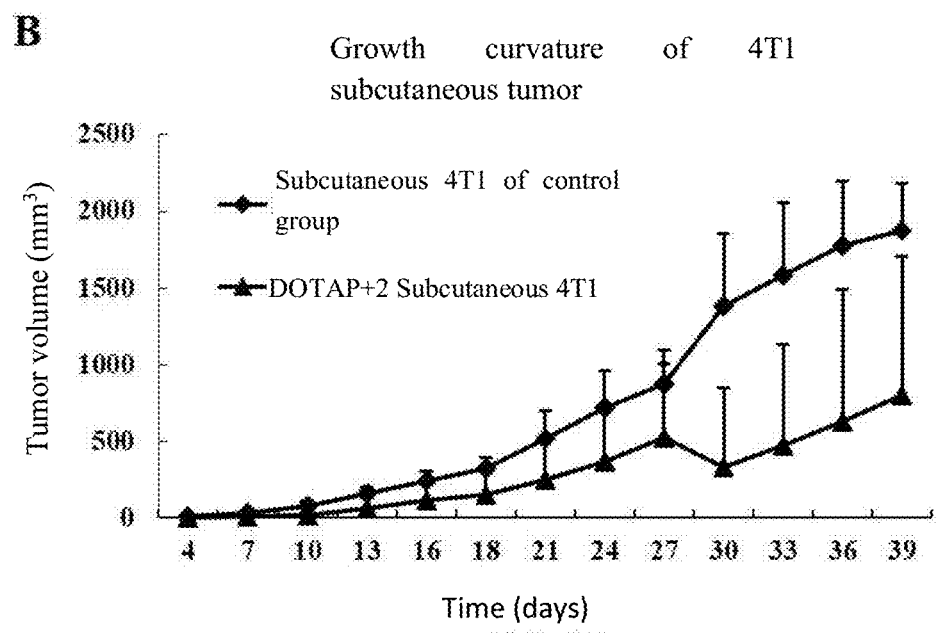

(2) The 4T1 subcutaneous tumor of the mice treated with the plasmid DNA/DOTAP complex grew more slowly than the 4T1 subcutaneous tumor of the control group (FIG. 26B).

In addition, the analysis of tumor tissues showed that there was a large amount of lymphocyte infiltration in CT26 subcutaneous tumor and 4T1 subcutaneous tumor tissues, mainly CD4$^+$ and CD8$^+$T lymphocytes, which was less in the control group, indicating that the pMVA-1/DOTAP complex could significantly improve the anti-tumor adaptive immune response of the body. The experiment further indicated that the splenic NK cell activity and CTL tumor killing activity of mice treated with the pMVA-1/DOTAP complex were higher than those of the control group.

The above experimental results show that for the model mice with abdominal metastasis of CT26, the pMVA-1/DOTAP complex can result in systemic anti-tumor memory immune response of the treated mice. After re-stimulated by tumor cells, including tumor cells of the same type and different types, it can inhibit the growth of tumor cells through memory T cells and a large amount of immune cytokines secreted by the memory T cells, so as to break the immune tolerance of tumors.

Example 20 Combined pMVA-1/DOTAP Complex and Chemotherapy for Treating Mice U14 Subcutaneous Model C57 female mice aged 6-8 weeks were raised. The mouse cervical cancer cell line U14 cultured to the logarithmic growth phase was prepared into a cell suspension and the cell density was 2×10$^7$/ml. Experimental animals were subcutaneously injected on the right back, with an injection system of 100 μl per mouse. When the tumor could be palpated (tumor volume is about 4 mm×4 mm×3 mm, i.e. the 5$^{th}$ day after inoculation), the mice were randomly divided into 6 groups, and administrated every 3 days for a total of 8 times according to the grouping and treatment scheme in Table 16. The tumor volume was measured every three days. After administration for 8 times, the mice were killed and subcutaneous tumors were dissected for examination.

TABLE 16

Grouping and treatment schemes of mice U14 subcutaneous model treated by combined PMVA-1/DOTAP complex and chemotherapy

| Group | Number of cases | Treatment | Dose | Route of administration | Course of treatment |
|---|---|---|---|---|---|
| 1 | 11 | NS (10% sucrose) | — | — | — |
| 2 | 11 | DOTAP | 100 ug/mouse | sc | — |
| 2 | 11 | pMVA-1 | 10 ug/mouse | sc | Q3d × 8 |
| 3 | 11 | DDP | 100 ug/mouse | ip | Q3d × 8 |
| 4 | 11 | DOTAP + pMVA1 | 100 ug + 100 ug/mouse | sc | Q3d × 8 |
| 5 | 12 | DOTAP/pMVA1 + DDP | 100 ug + 10 ug/mouse + 100 ug/mouse | sc | Q3d × 8 |

Wherein, the administration volume is 100 μl per mouse, DDP is intraperitoneally administrated once a week. DDP is Cisplatin and LP is pMVA-1/DOTAP complex.

Figure 27:
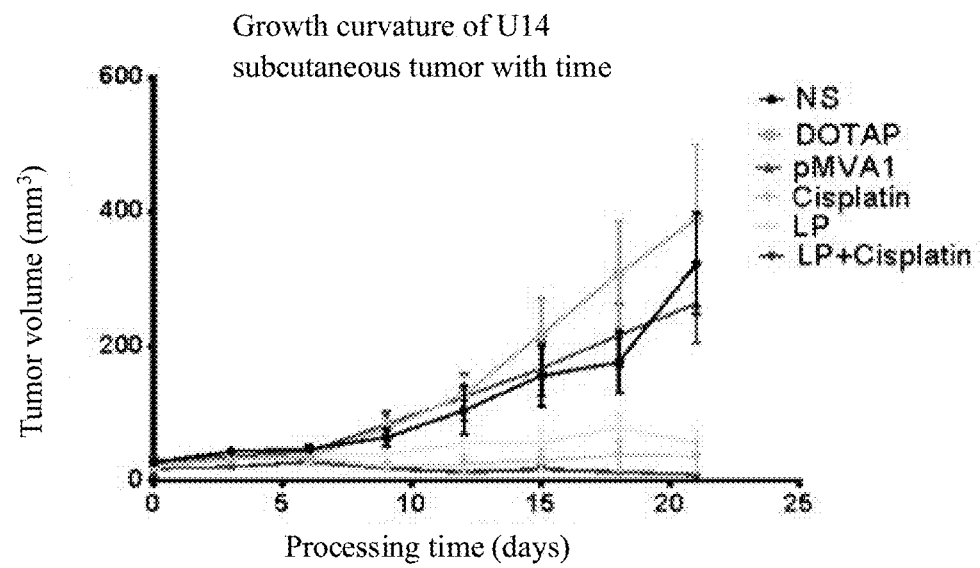
FIG. 27. is a graph showing the pMVA-1/DOTAP complex in combination with Cisplatin significantly inhibited the growth of tumor cells in mouse models with subcutaneously inoculated U14. *P<0.05. Wherein, for the NS group: only 10% sucrose was injected, for the DOTAP group: only DOTAP was injected, for the pMVA1 group: only pMVA-1 plasmids were injected, for Cisplatin: only Cisplatin was injected, for the LP group: pMVA-1/DOTAP complex was injected, and for the LP+Cisplatin group: pMVA-1/DOTAP complex in combination with Cisplatin was injected.

As shown in FIG. 27, the experimental results show that slow tumor growth is observed in the Cisplatin group, pMVA-1/DOTAP complex group, combined pMVA-1/DOTAP complex and Cisplatin treatment group. In particular, the combined treatment group show the slowest tumor growth, and the tumor volume of the above three groups are significantly lower than NS group, DOTAP group and pMVA-1 group. In addition, the combined pMVA-1/DOTAP complex and Cisplatin treatment group has significantly smaller tumor volume than the Cisplatin group and pMVA-1/DOTAP complex group alone.

The analysis of tumor tissue shows that a large number of lymphocyte infiltration is observed in the pMVA-1/DOTAP complex group, and combined pMVA-1/DOTAP complex and Cisplatin treatment group, which is less common in the chemotherapy group, DOTAP group, pMVA-1 group and NS group, indicating that the combined pMVA-1/DOTAP complex and Cisplatin treatment can further enhance the anti-tumor adaptive immune response of the pMVA-1/DOTAP complex.

Thus, the pMVA-1/DOTAP complex can significantly improve the anti-tumor immune response of the body and enhance the anti-tumor effect of chemotherapy. Both of them are combined to significantly inhibit the growth of tumor, and the anti-tumor effect of combined treatment is superior to that of Cisplatin alone.

Example 21 Combined pMVA-1/DOTAP Complex and Radiotherapy for Treating Hela Subcutaneous Model in Nude Mice Nude mice aged 6-8 weeks were raised. The human cervical cancer cell line Hela cultured to the logarithmic growth phase was prepared into a cell suspension, and the cell density was $1\times10^7$/ml. Experimental animals were subcutaneously injected on the right back, with an injection system of 100 μl per mouse. When the tumor could be palpated (tumor volume is about 5 mm×5 mm×5 mm, i.e. the $7^{th}$ day after inoculation), the mice were randomly divided into 4 groups. See Table 17 for specific dosage regimen. On the $7^{th}$ day of inoculation, mice were administrated as follows: the combined treatment group and pMVA-1/DOTAP group were intratumorally injected with 100 μl of plasmid pMVA-1/DOTAP complex (the complex formed by 10 μg of plasmid pMVA-1 and 100 μg of DOTAP) respectively; and NS group was injected with 100 μl of normal saline. Both were intratumorally injected at multiple points, twice a week, and a total of 5 times. The radiotherapy group and the combined treatment group received radiotherapy 24 h after the first dose (i.e. the $8^{th}$ day after inoculation), with a total dose of 2Gy for each radiotherapy, a frequency of 200 cGy/min, a depth of 2 mm from the skin source, and every 2 days, for a total of 3 times. After intratumoral administration for 5 times, tumor volume was measured, mice were killed, and tumor tissues were taken for examination.

TABLE 17

Grouping and therapeutic regimen of Hela subcutaneous model of nude mice treated with pMVA-1/DOTAP complex combined with radiotherapy

| Group | Number of mice (Nr.) | Plasmid DNA (μg) | DOTAP (μg) | Total dose of radiotherapy (Gy) |
|---|---|---|---|---|
| Normal saline (NS) | 10 | — | — | — |
| pMVA-1/DOTAP | 10 | 10 | 100 | — |
| Radiotherapy | 10 | — | — | 2 |
| pMVA-1/DOTAP + radiotherapy | 10 | 10 | 100 | 2 |

Figure 28:
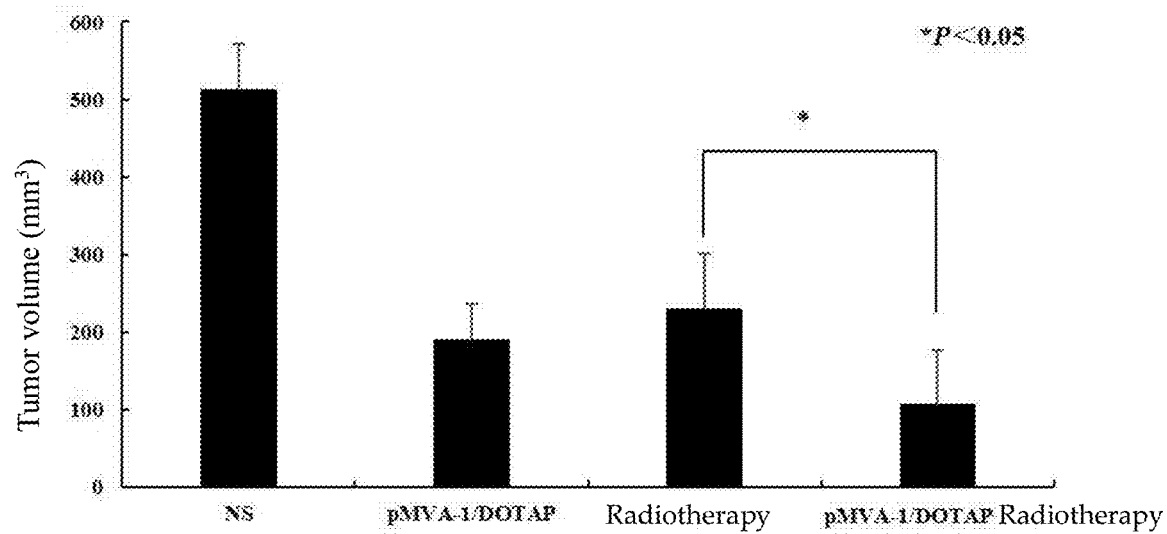
FIG. 28 is a graph showing the pMVA-1/DOTAP complex in combination with radiotherapy significantly inhibited the growth of tumor cells in mouse models with subcutaneous U14. *P<0.05.

As shown in FIG. 28, the experimental results show that the tumor volumes of radiotherapy group, pMVA-1/DOTAP complex group, and combined pMVA-1/DOTAP complex and radiotherapy treatment group are significantly lower than that of NS group. In addition, the tumor volume of combined pMVA-1/DOTAP complex and radiotherapy treatment group is significantly lower than that of the radiotherapy group alone.

In addition, the analysis of tumor tissues shows that a large number of lymphocyte infiltration is observed in the pMVA-1/DOTAP complex group, combined pMVA-1/DOTAP complex and radiotherapy treatment group, which is less common in the radiotherapy group and NS group, indicating that the combined pMVA-1/DOTAP complex and radiotherapy treatment can further enhance the anti-tumor specific immune response of the pMVA-1/DOTAP complex.

Thus, the pMVA-1/DOTAP complex can significantly improve the anti-tumor immune response of the body and enhance the anti-tumor effect of radiotherapy. Both of them are combined to significantly inhibit the growth of tumor, and the anti-tumor effect of combined treatment is superior to that of radiotherapy alone.

In the in vivo experiment of the tumor treatment through combined pMVA-1/DOTAP complex and immune response regulator, we found the experimental results similar to those of Examples 20 and 21: the pMVA-1/DOTAP complex can significantly improve the immune response of the body against tumor, and strengthen the anti-tumor effect of immune response regulators (e.g., cytokines, class II HLA protein binding helper molecules, CD40 agonists, checkpoint receptor antagonists (e.g., CTLA-4, PD-1, Stat3), B7 costimulatory molecules, FLt3 agonists, CD40L agonists, etc.). Both of them are combined to significantly inhibit tumor growth, and the anti-tumor effect of the combined treatment is superior to that of the treatment with the immune response regulators alone.

Example 22 Anti-Tumor Effect of Tumor Cell Vaccine Prepared by Taking DNA/Cationic Biomaterial Complex as Adjuvant (1) Preparation of CT26 Colon Cancer Cell In Situ Vaccine:

a. Preparation of pVAX1/DOTAP Complex: Refer to Example 3 b. Preparation of Apoptosis and Necrosis CT26 Colon Cancer Cells:

The CT26 colon cancer cells cultured to the logarithmic growth phase were inoculated into a 6-well plate as per $1\times10^6$ cells/well and cultured at 37° C. and 5% $CO_2$ until the cells were adhered to the wall. Then, the actinomycin D medium containing 200 ng/ml was added and cultured for 12 h to induce apoptosis. After the apoptosis cell suspension was collected, 5 μl of Annexin V-FITC and 10 μl of propidium iodide (PI, made by Sigma) were added, mixed, incubated at room temperature for 15 min in the dark, tested for the apoptosis by a flow cytometer, enriched and diluted for later use.

In addition, CT26 cells in the logarithmic growth phase were prepared into necrotic tumor cells by the heating method, i.e. water bath at 56° C. for 1 h. The necrotic morphology of the cells was observed under a microscope. The cell death rate was tested by the trypan blue exclusion. The suspension of necrotic tumor cells was collected, mixed with 0.4% trypan blue in equal volume, and left for 5-15 min.

c. Preparation of CT26 Colon Cancer Cell Vaccine:

The pVAX1/DOTAP complex was used as vaccine and mixed with necrotic or apoptotic CT26 colon cancer cells to prepare CT26 cell vaccine.

(2) Evaluation of Anti-Tumor Effect of CT26 Colon Cancer Cell Vaccine in Mouse Colon Cancer CT26 Abdominal Model Mice were injected intraperitoneally as per $1\times10^6$ CT26 cells/mouse. From the $3^{rd}$ day after injection, they were intraperitoneally administrated and divided into a normal saline group (NS), a pVAX1/DOTAP necrotic cell vaccine group (NECRO) and a pVAX1/DOTAP apoptotic cell vaccine group (APOP). The mice were intraperitoneally administrated once a week. The survival time of mice was recorded.

Figure 29:
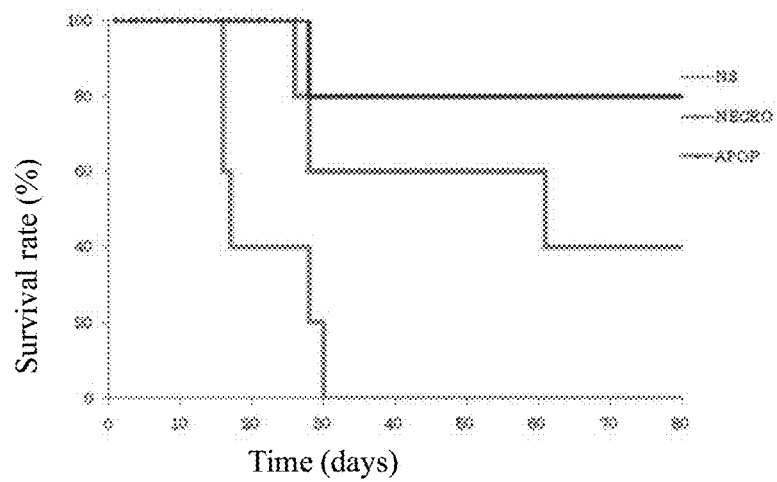
FIG. 29 is a graph showing the pVAX1/DOTAP complex was used as an adjuvant and mixed with apoptotic or necrotic CT26 cells to prepare a tumor cell vaccine, which significantly prolonged the survival time of tumor-bearing mice and had good anti-tumor effects. Wherein, NS: normal saline group; NECRO: necrotic tumor cell vaccine group prepared by pVAX1/DOTAP complex mixed with necrotic CT26 cells; and APOP: apoptotic cell vaccine group prepared by pVAX1/DOTAP complex mixed with apoptotic CT26 cells.

As shown in FIG. 29, the survival time of mice in the vaccine groups (including NECRO and APOP) significantly prolonged compared with that in the normal saline group (NS). In particular, the survival rate of the NS group on 30 d was 0, while that of the NECRO group and APOP group at 80 d was 40% and 80% respectively. The pVAX1/DOTAP complex can significantly improve the immunogenicity of necrotic or apoptotic tumor cells, and the tumor cell vaccine prepared by mixing them has good anti-tumor effect.

The above experimental results show that the DNA/cationic biomaterial complex can be used as adjuvant for tumor cell vaccine, and can significantly improve the immune response of necrosis/apoptosis cell vaccine to activate the anti-tumor of the body and achieve the purpose of effectively inhibiting tumor growth and prolonging the survival time.

The above examples show that the DNA/cationic biomaterial complex formed by the replicable DNA that does not express exogenous genes and cationic biomaterials of the present invention, or the oxidized DNA/cationic biomaterial complex formed by oxidized DNA and cationic biomaterials formed by the oxidation of these DNA in vitro, can play a synergistic role in directly killing tumors as an adjuvant of tumor vaccines or tumor cell vaccines, and can also synergistically activate the anti-tumor effects of innate immune response and adaptive reactions of the body, induce the body to generate anti-tumor long-term memory immunity and break tumor immune tolerance. Therefore, the DNA/cationic biomaterial composite of the present invention can be used as a tumor vaccine alone or in combination with other tumor treatment methods for treating different types of tumor.

The above embodiments are the preferred embodiments of the present invention, but the embodiments of the present invention are not limited by the above embodiments, and any other changes, modifications, substitutions, combinations, and simplifications made without departing from the spirit and principles of the present invention shall be equivalent replacement methods, and shall be included in the scope of protection of the present invention.

```
                              Sequence table

<210> 1
<211> 1978
<212> DNA
<213> Artificial Sequence
<220>
<223> nucleotide sequence of pMVA
<400> 1
gactcttcgc gatgtacggg ccagatatac gccttctact gggcggtttt atggacagca   60
agcgaaccgg aattgccagc tggggcgccc tctggtaagg ttgggaagcc ctgcaaagta  120
aactggatgg cttctcgcc gccaaggatc tgatggcgca ggggatcaag ctctgatcaa  180
gagacaggat gaggatcgtt tcgcatgatt gaacaagatg gattgcacgc aggttctccg  240
gccgcttggg tggagaggct attcggctat gactgggcac aacagacaat cggctgctct  300
gatgccgccg tgttccggct gtcagcgcag gggcgcccgg ttcttttttgt caagaccgac  360
ctgtccggtg ccctgaatga actgcaagac gaggcagcgc ggctatcgtg gctggccacg  420
acgggcgttc cttgcgcagc tgtgctcgac gttgtcactg aagcgggaag ggactggctg  480
ctattgggcg aagtgccggg gcaggatctc ctgtcatctc accttgctcc tgccgagaaa  540
gtatccatca tggctgatgc aatgcggcgg ctgcatacgc ttgatccggc tacctgccca  600
ttcgaccacc aagcgaaaca tcgcatcgag cgagcacgta ctcggatgga agccggtctt  660
gtcgatcagg atgatctgga cgaagagcat caggggctcg cgccagccga actgttcgcc  720
aggctcaagg cgagcatgcc cgacggcgag gatctcgtcg tgacccatgg cgatgcctgc  780
ttgccgaata tcatggtgga aaatggccgc ttttctggat tcatcgactg tggccggctg  840
ggtgtggcgg accgctatca ggacatagcg ttggctaccc gtgatattgc tgaagagctt  900
ggcggcgaat gggctgaccg cttcctcgtg ctttacggta tcgccgctcc cgattcgcag  960
cgcatcgcct tctatcgcct tcttgacgag ttcttctgaa ttattaacgc ttacaatttc 1020
ctgatgcggt attttctcct tacgcatctg tgcggtattt cacaccgcat acaggtggca 1080
cttttcgggg aaatgtgcgc ggaacccta tttgtttatt tttctaaata cattcaaata 1140
tgtatccgct catgagacaa taaccctgat aaatgcttca ataatagcac gtgctaaaac 1200
ttcattttta atttaaaagg atctaggtga agatccttt tgataatctc atgaccaaaa 1260
tcccttaacg tgagttttcg ttccactgag cgtcagaccc cgtagaaaag atcaaaggat 1320
cttcttgaga tcctttttt ctgcgcgtaa tctgctgctt gcaaacaaaa aaaccaccgc 1380
taccagcggt ggtttgtttg ccggatcaag agctaccaac tcttttttccg aaggtaactg 1440
gcttcagcag agcgcagata ccaaatactg tccttctagt gtagccgtag ttaggccacc 1500
acttcaagaa ctctgtagca ccgcctacat acctcgctct gctaatcctg ttaccagtgg 1560
ctgctgccag tggcgataag tcgtgtctta ccgggttgga ctcaagacga tagttaccgg 1620
ataaggcgca gcggtcgggc tgaacggggg gttcgtgcac acagcccagc ttggagcgaa 1680
cgacctacac cgaactgaga tacctacagc gtgagctatg agaaagcgcc acgcttcccg 1740
aagggagaaa ggcggacagg tatccggtaa gcggcagggt cggaacagga gagcgcacga 1800
gggagcttcc aggggggaaac gcctggtatc tttatagtcc tgtcgggttt cgccacctct 1860
gacttgagcg tcgatttttg tgatgctcgt cagggggggcg gagcctatgg aaaaacgcca 1920
gcaacgcggc ctttttacgg ttcctgggct tttgctggcc ttttgctcac atgactt     1978

<210> 2
<211> 1977
<212> DNA
<213> Artificial Sequence
<220>
<223> nucleotide sequence of pMVA-1
<400> 2
gctgcttcgc gatgtacggg ccagatatac gccttctact gggcggtttt atggacagca   60
agcgaaccgg aattgccagc tggggcgccc tctggtaagg ttgggaagcc ctgcaaagta  120
aactggatgg cttctcttgcc gccaaggatc tgatggcgca ggggatcaag ctctgatcaa  180
gagacaggat gaggatcgtt tcgcatgatt gaacaagatg gattgcacgc aggttctccg  240
gccgcttggg tggagaggct attcggctat gactgggcac aacagacaat cggctgctct  300
gatgccgccg tgttccggct gtcagcgcag gggcgcccgg ttcttttttgt caagaccgac  360
ctgtccggtg ccctgaatga actgcaagac gaggcagcgc ggctatcgtg gctggccacg  420
```

-continued

| Sequence table | | | | | |
|---|---|---|---|---|---|
| acgggcgttc | cttgcgcagc | tgtgctcgac | gttgtcactg | aagcgggaag ggactggctg | 480 |
| ctattgggcg | aagtgccggg | gcaggatctc | tgtcatctc | accttgctcc tgccgagaaa | 540 |
| gtatccatca | tggctgatgc | aatgcggcgg | ctgcatacgc | ttgatccggc tacctgccca | 600 |
| ttcgaccacc | aagcgaaaca | tcgcatcgag | cgagcacgta | ctcggatgga agccggtctt | 660 |
| gtcgatcagg | atgatctgga | cgaagagcat | caggggctcg | cgccagccga actgttcgcc | 720 |
| aggctcaagg | cgagcatgcc | cgacggcgag | gatctcgtcg | tgacccatgg cgatgcctgc | 780 |
| ttgccgaata | tcatggtgga | aaatgccgc | ttttctggat | tcatcgactg tggccggctg | 840 |
| ggtgtggcgg | accgctatca | ggacatagcg | ttggctaccc | gtgatattgc tgaagagctt | 900 |
| ggcggcgaat | gggctgaccg | cttcctcgtg | ctttacggta | tcgccgctcc cgattcgcag | 960 |
| cgcatcgcct | tctatcgcct | tcttgacgag | ttccttctgaa | ttattaacgc ttacaatttc | 1020 |
| ctgatgcggt | attttctcct | tacgcatctg | tgcggtattt | cacaccgcat caggtggcac | 1080 |
| ttttcgggga | aatgtgcgcg | gaaccccctat | ttgttttattt | ttctaaatac attcaaatat | 1140 |
| gtatccgctc | atgagacaat | aaccctgata | aatgcttcaa | taatagcacg tgctaaaact | 1200 |
| tcatttttaa | tttaaaagga | tctaggtgaa | gatcctttt | gataatctca tgaccaaaat | 1260 |
| cccttaacgt | gagttttcgt | tccactgagc | gtcagacccc | gtagaaaaga tcaaaggatc | 1320 |
| ttcttgagat | ccttttttc | tgcgcgtaat | ctgctgcttg | caaacaaaaa aaccaccgct | 1380 |
| accagcggtg | gtttgtttgc | cggatcaaga | gctaccaact | cttttccga aggtaactgg | 1440 |
| cttcagcaga | gcgcagatac | caaatactgt | tcttctagtg | tagccgtagt taggccacca | 1500 |
| cttcaagaac | tctgtagcac | cgcctacata | cctcgctctg | ctaatcctgt taccagtggc | 1560 |
| tgctgccaga | ggcgataagt | cgtgtcttac | cgggttggac | tcaagacgat agttaccgga | 1620 |
| taaggcgcag | cggtcgggct | gaacggggg | ttcgtgcaca | cagcccagct tggagcgaac | 1680 |
| gacctacacc | gaactgagat | acctacagcg | tgagctatga | gaaagcgcca cgcttcccga | 1740 |
| agggagaaag | gcggacaggt | atccggtaag | cggcagggtc | ggaacaggag agcgcacgag | 1800 |
| ggagcttcca | gggggaaacg | cctggtatct | ttatagtcct | gtcgggtttc gccacctcgg | 1860 |
| acttgagcgt | cgatttttgt | gatgctcgtc | aggggggcgg | agcctatgga aaaacgccag | 1920 |
| caacgcggcc | tttttacggt | tcctggcctt | ttgctggcct | tttgctcaca tgactt | 1977 |

<210> 3
<211> 120
<212> DNA
<213> Artificial Sequence
<220>
<223> nucleotide sequence 1 of mtDNA
<400> 3

| cccattattc | ctagaaccag | gcgacctgcg | actccttgac | gttgacaatc gagtagtact | 60 |
| cccgattgaa | gccccattc | gtataataat | tacatcacaa | gacgtcttgc actcatgagc | 120 |

<210> 4
<211> 600
<212> DNA
<213> Artificial Sequence
<220>
<223> nucleotide sequence 2 of mtDNA
<400> 4

| ctgaactatc | ctgcccgcca | tcatcctagt | cctcatcgcc | ctcccatccc tacgcatcct | 60 |
| ttacataaca | gacgaggtca | acgatccctc | cctaccatc | aaatcaattg gccaccaatg | 120 |
| gtactgaacc | tacgagtaca | ccgactacgg | cggactaatc | ttcaactcct acatacttcc | 180 |
| cccattattc | ctagaaccag | gcgacctgcg | actccttgac | gttgacaatc gagtagtact | 240 |
| cccgattgaa | gccccattc | gtataataat | tacatcacaa | gacgtcttgc actcatgagc | 300 |
| tgtccccaca | ttaggcttaa | aaacagatgc | aattcccgga | cgtctaaacc aaaccacttt | 360 |
| caccgctaca | cgaccgggg | tatactacgg | tcaatgctct | gaaatctgtg gagcaaacca | 420 |
| cagttttcatg | cccatcgtcc | tagaattaat | tcccctaaaa | atctttgaaa tagggcccgt | 480 |
| attaccctta | tagcaccccc | tctacccct | ctagagccca | ctgtaaagct aacttagcat | 540 |
| taacctttta | agttaaagat | taagagaacc | aacacctctt | tacagtgaaa tgccccaact | 600 |

<210> 5
<211> 2000
<212> DNA
<213> Artificial Sequence
<220>
<223> nucleotide sequence 3 of mtDNA
<400> 5

| tacgttgtag | ctcacttcca | ctatgtccta | tcaataggag | ctgtatttgc catcatagga | 60 |
| ggcttcattc | actgatttcc | cctattctca | ggctacaccc | tagaccaaac ctacgccaaa | 120 |
| atccatttca | ctatcatatt | catcggcgta | aatctaactt | tcttcccaca acactttctc | 180 |
| ggcctatccg | gaatgccccg | acgttactcg | gactaccga | atgcatacac cacatgaaac | 240 |
| atcctatcat | ctgtaggctc | attcatttct | ctaacagcag | taatattaat aattttcatg | 300 |
| atttgagaag | ccttcgcttc | gaagcgaaaa | gtcctaatag | tagaagaacc ctccataaac | 360 |
| ctggagtgac | tatatggatg | ccccccaccc | taccacacat | tcgaagaacc cgtatacata | 420 |
| aaatctagac | aaaaaaggaa | ggaatcgaac | cccccaaagc | tggtttcaag ccaaccccat | 480 |
| ggcctccatg | acttttttcaa | aaaggtatta | gaaaaaccat | ttcataactt tgtcaaagtt | 540 |
| aaattatagg | ctaaatccta | tatatcttaa | tggcacatgc | agcgcaagta ggtctacaag | 600 |
| acgctacttc | ccctatcata | gaagagctta | tcacctttca | tgatcacgcc tcataatca | 660 |
| ttttccttat | ctgcttccta | gtcctgtatg | ccctttttcct | aacactcaca caaaactaa | 720 |
| ctaatactaa | catctcagac | gctcaggaaa | tagaaaccgt | ctgaactatc ctgcccgcca | 780 |
| tcatcctagt | cctcatcgcc | ctcccatccc | tacgcatcct | ttacataaca gacgaggtca | 840 |
| acgatccctc | cctaccatc | aaatcaattg | gccaccaatg | gtactgaacc tacgagtaca | 900 |

-continued

| Sequence table | | | | | |
|---|---|---|---|---|---|
| ccgactacgg | cggactaatc | ttcaactcct | acatacttcc | cccattattc | ctagaaccag   960 |
| gcgacctgcg | actccttgac | gttgacaatc | gagtagtact | cccgattgaa | gcccccattc  1020 |
| gtataataat | tacatcacaa | gacgtcttgc | actcatgagc | tgtccccaca | ttaggcttaa  1080 |
| aaacagatgc | aattcccgga | cgtctaaacc | aaaccacttt | caccgctaca | cgaccggggg  1140 |
| tatactacgg | tcaatgctct | gaaatctgtg | gagcaaacca | cagtttcatg | cccatcgtcc  1200 |
| tagaattaat | tccctaaaa | atctttgaaa | tagggcccgt | atttacccta | tagcaccccc  1260 |
| tctacccct | ctagagccca | ctgtaaagct | aacttagcat | taaccttta | agttaaagat  1320 |
| taagagaacc | aacacctctt | tacagtgaaa | tgccccaact | aaatactacc | gtatggccca  1380 |
| ccataattac | ccccatactc | cttacactat | tcctcatcac | ccaactaaaa | atattaaaca  1440 |
| caaactacca | cctacctccc | tcaccaaagc | ccataaaaat | aaaaaattat | aacaaaccct  1500 |
| gagaaccaaa | atgaacgaaa | atctgttcgc | ttcattcatt | gcccccacaa | tcctaggcct  1560 |
| acccgccgca | gtactgatca | ttctatttcc | ccctctattg | atccccacct | ccaaatatct  1620 |
| catcaacaac | cgactaatca | ccacccaaca | atgactaatc | aaactaacct | caaaacaaat  1680 |
| gataaccata | cacaacacta | aaggacgaac | ctgatctctt | atactagtat | ccttaatcat  1740 |
| ttttattgcc | acaactaacc | tcctcggact | cctgcctcac | tcatttacac | caaccaccca  1800 |
| actatctata | aacctagcca | tggccatccc | tttatgagcg | ggcgcagtga | ttataggctt  1860 |
| tcgctctaag | attaaaaatg | ccctagccca | cttcttacca | caaggcacac | ctacaccct  1920 |
| tatccccata | ctagttatta | tcgaaaccat | cagcctactc | attcaaccaa | tagccctggc  1980 |
| cgtacgccta | accgctaaca | | | | 2000 |

<210> 6
<211> 2098
<212> DNA
<213> Artificial Sequence
<220>
<223> nucleotide sequence of pMVA-2
<400> 6

| gactcttcgc | gatgtacggg | ccagatatac | gccccattat | tcctagaacc | aggcgacctg   60 |
|---|---|---|---|---|---|
| cgactccttg | acgttgacaa | tcgagtagta | ctcccgattg | aagcccccat | tcgtataata  120 |
| attcatcac | aagacgtctt | gcactcatga | gccttctact | gggcggtttt | atggacagca  180 |
| agcgaaccgg | aattgccagc | tggggcgccc | tctggtaagg | ttgggaagcc | ctgcaaagta  240 |
| aactggatgg | ctttctcgcc | gccaaggatc | tgatggcgca | ggggatcaag | ctctgatcaa  300 |
| gagacaggat | gaggatcgtt | tcgcatgatt | gaacaagatg | gattgcacgc | aggctctccg  360 |
| gccgcttggg | tggagaggct | attcggctat | gactgggcac | aacagacaat | cggctgctct  420 |
| gatgccgccg | tgttccggct | gtcagcgcag | gggcgcccgg | ttcttttgt | caagaccgac  480 |
| ctgtccggtg | ccctgaatga | actgcaagac | gaggcagcgc | ggctatcgtg | gctggccacg  540 |
| acgggcgttc | cttgcgcagc | tgtgctcgac | gttgtcactg | aagcgggaag | ggactggctg  600 |
| ctattgggcg | aagtgccggg | gcaggatctc | ctgtcatctc | accttgctcc | tgccgagaaa  660 |
| gtatccatca | tggctgatgc | aatgcggcgg | ctgcatacgc | ttgatccggc | tacctgccca  720 |
| ttcgaccacc | aagcgaaaca | tcgcatcgag | cgagcacgta | ctcggatgga | agccggtctt  780 |
| gtcgatcagg | atgatctgga | cgaagagcat | caggggctcg | cgccagccga | actgttcgcc  840 |
| aggctcaagg | cgagcatgcc | cgacggcgag | gatctcgtcg | tgacccatgg | cgatgcctgc  900 |
| ttgccgaata | tcatggtgga | aaatggccgc | ttttctggat | tcatcgactg | tggccggctg  960 |
| ggtgtggcgg | accgctatca | ggacatagcg | ttggctaccc | gtgatattgc | tgaagagctt 1020 |
| ggcggcgaat | gggctgaccg | cttcctcgtg | ctttacggta | tcgccgctcc | cgattcgcag 1080 |
| cgcatcgcct | tctatcgcct | tcttgacgag | ttcttctgaa | ttattaacgc | ttacaatttc 1140 |
| ctgatgcggt | attttctcct | tacgcatctg | tgcggtattt | cacaccgcat | acaggtggca 1200 |
| cttttcgggg | aaatgtgcgc | ggaaccccta | tttgtttatt | tttctaaata | cattcaaata 1260 |
| tgtatccgct | catgagacaa | taaccctgat | aaatgcttca | ataatagcac | gtgctaaaac 1320 |
| ttcatttta | atttaaaagg | atctaggtga | agatccttt | tgataatctc | atgaccaaaa 1380 |
| tcccttaacg | tgagttttcg | ttccactgag | cgtcagaccc | cgtagaaaag | atcaaaggat 1440 |
| cttcttgaga | tccttttttt | ctgcgcgtaa | tctgctgctt | gcaaacaaaa | aaaccaccgc 1500 |
| taccaggcggt | ggtttgtttg | ccggatcaag | agctaccaac | tctttttccg | aaggtaactg 1560 |
| gcttcagcag | agcgcagata | ccaaatactg | tccttctagt | gtagccgtag | ttaggccacc 1620 |
| acttcaagaa | ctctgtagca | ccgcctacat | acctcgctct | gctaatcctg | ttaccagtgg 1680 |
| ctgctgccaa | tggcgataag | tcgtgtctta | ccgggttgga | ctcaagacga | tagttaccgg 1740 |
| ataaggcgca | gcggtcgggc | tgaacggggg | gttcgtgcac | acagcccagc | ttggagcgaa 1800 |
| cgacctacac | cgaactgaga | tacctacagc | gtgagctatg | agaaagcgcc | acgcttcccg 1860 |
| aagggagaaa | ggcggacagg | tatccggtaa | gcggcagggt | cggaacagga | gagcgcacga 1920 |
| gggagcttcc | agggggaaac | gcctggtatc | tttatagtcc | tgtcgggttt | cgccacctct 1980 |
| gacttgagcg | tcgatttttg | tgatgctcgt | caggggggcg | gagcctatgg | aaaaacgcca 2040 |
| gcaacgcggc | cttttacgg | ttcctggcct | tttgctggcc | ttttgctcac | atgactt    2098 |

<210> 7
<211> 2578
<212> DNA
<213> Artificial Sequence
<220>
<223> nucleotide sequence of pMVA-3
<400> 7

| gactcttcgc | gatgtacggg | ccagatatac | gcctgaacta | tcctgcccgc | catcatccta   60 |
|---|---|---|---|---|---|
| gtcctcatcg | ccctcccatc | cctacgcatc | ctttacataa | cagacgaggt | caacgatccc  120 |
| tcccttacca | tcaaatcaat | tggccaccaa | tggtactgaa | cctacgagta | caccgactac  180 |
| ggcggactaa | tcttcaactc | ctacatactt | ccccccattat | tcctagaacc | aggcgacctg  240 |
| cgactccttg | acgttgacaa | tcgagtagta | ctcccgattg | aagcccccat | tcgtataata  300 |
| attcatcac | aagacgtctt | gcactcatga | gctgtcccca | cattaggctt | aaaaacagat  360 |
| gcaattcccg | gacgtctaaa | ccaaaccact | ttcaccgcta | cacgaccggg | ggtatactac  420 |

```
                             Sequence table ggtcaatgct ctgaaatctg tggagcaaac cacagtttca tgcccatcgt cctagaatta   480
attcccctaa aaatctttga aatagggccc gtatttaccc tatagcaccc cctctacccc   540
ctctagagcc cactgtaaag ctaacttagc attaacctttt aagttaaag attaagagaa   600
ccaacacctc tttacagtga aatgcccaa ctcttctact gggcggtttt atggacagca   660
agcgaaccgg aattgccagc tggggcgccc tctggtaagg ttgggaagcc ctgcaaagta   720
aactggatgt ctttctcgcc gccaaggatc tgatggcgca ggggatcaag ctctgatcaa   780
gagacaggat gaggatcgtt tcgcatgatt gaacaagatg gattgcacgc aggttctccg   840
gccgcttggg tggagaggct attcggctat gactgggcac aacagacaat cggctgctct   900
gatgccgccg tgttccggct gtcagcgcag gggcgcccgg ttcttttttgt caagaccgac   960
ctgtccggtg ccctgaatga actgcaagac gaggcagcgc ggctatcgtg gctggccacg  1020
acgggcgttc cttgcgcagc tgtgctcgac gttgtcactg aagcgggaag ggactggctg  1080
ctattgggcg aagtgccggg gcaggatctc ctgtcatctc accttgctcc tgccgagaaa  1140
gtatccatca tggctgatgc aatgcggcgg ctgcatacgc ttgatccggc tacctgccca  1200
ttcgaccacc aagcgaaaca tcgcatcgag cgagcacgta ctcggatgga agccggtctt  1260
gtcgatcagg atgatctgga cgaagagcat caggggctcg cgccagccga actgttcgcc  1320
aggctcaagg cgagcatgcc cgacggcgag gatctcgtcg tgacccatgg cgatgcctgc  1380
ttgccgaata tcatggtgga aaatggccgc ttttctggat tcatcgactg tggccggctg  1440
ggtgtggcgg accgctatca ggacatagcg ttggctaccc gtgatattgc tgaagagctt  1500
ggcggcgaat gggctgaccg cttcctcgtg ctttacggta tcgccgctcc cgattcgcag  1560
cgcatcgcct tctatcgcct tcttgacgag ttcttctgaa ttattaacgc ttacaatttc  1620
ctgatgcggt atttttctcct tacgcatctg tgcggtattt cacaccgcat acaggtggca  1680
cttttcgggg aaatgtgcgc ggaacccta tttgtttatt tttctaaata cattcaaata  1740
tgtatccgct catgagacaa taaccctgat aaatgcttca ataatagcac gtgctaaaac  1800
ttcattttta atttaaaagg atcaggtga agatccttt tgataatctc atgaccaaaa  1860
tcccttaacg tgagttttcg ttccactgag cgtcagaccc cgtagaaaag atcaaaggat  1920
cttcttgaga tcctttttttt ctgcgcgtaa tctgctgctt gcaaacaaaa aaaccaccgc  1980
taccagcggt ggtttgtttg ccggatcaag agctaccaac tttttttccg aaggtaactg  2040
gcttcagcag agcgcagata ccaaatactg tccttctagt gtagccgtag ttaggccacc  2100
acttcaagaa ctctgtagca ccgcctacat acctcgctct gctaatcctg ttaccagtgg  2160
ctgctgccag tggcgataag tcgtgtctta ccgggttgga ctcaagacga tagttaccgg  2220
ataaggcgca gcggtcgggc tgaacggggg gttcgtgcac acagcccagc ttggagcgaa  2280
cgacctacac cgaactgaga tacctacagc gtgagctatg agaaagcgcc acgcttcccg  2340
aagggagaaa ggcggacagg tatccggtaa gcggcagggt cggaacagga gagcgcacga  2400
gggagcttcc agggggaaac gcctggtatc tttatagtcc tgtcgggttt cgccacctct  2460
gacttgagcg tcgatttttg tgatgctcgt caggggggcg gagcctatgg aaaaacgcca  2520
gcaacgcggc cttttacgg ttcctgggct tttgctggcc ttttgctcac atgactt      2578

<210> 8
<211> 3978
<212> DNA
<213> Artificial Sequence
<220>
<223> nucleotide sequence of pMVA-4
<400> 8
gactcttcgc gatgtacggg ccagatatac gctacgttgt agctcacttc cactatgtcc    60
tatcaatagg agctgtattt gccatcatag gaggcttcat tcactgattt cccctattct   120
caggctacac cctagaccaa acctacgcca aaatccattt cactatcata ttcatcggcg   180
taaatctaac tttcttccca caacactttc tcggcctatc tggaatgccc cgacgttact   240
cggactaccc cgatgcatac accacatgaa acatcctatc atctgtaggc tcattcattt   300
ctctaacagc agtaatatta ataattttca tgatttgaga agccttcgct tcgaagcgaa   360
aagtcctaat agtagaagaa cctaccataa acctggagtg actatatgga tgccccccac   420
cctaccacac attcgaagaa cccgtataca taaaatctag acaaaaaagg aaggaatcga   480
acccccaaa gctggtttca agccaacccc atggcctcca tgacttttttc aaaaaggtat   540
tagaaaaacc atttcataac tttgtcaaag ttaaattata ggctaaatcc tatatatctt   600
aatggcacat gcagcgcaag taggtctaca agacgctact tccccatca tagaagagct   660
tatcaccttt catgatcacg ccctcataat catttttcctt atctgcttcc tagtcctgta   720
tgcccttttc ctaacactca caacaaaact aactaatact aacatctac acgctcagga   780
aatagaaacc gtctgaacta tcctgcccgc catcatccta gtcctcatcg ccctcccatc   840
cctacgcatc ctttacataa cagacgaggt caacgatccc tcccttacca tcaaatcaat   900
tggccaccaa tggtactgaa cctacgagta caccgactac ggcggactaa tcttcaactc   960
ctacatactt cccccattat tcctagaacc aggcgacctc gactccttg acgttgacaa  1020
tcgagtagta ctcccgattg aagcccccat tcgtataata attacatcac aagacgtctt  1080
gcactcatga gctgtcccca cattaggctt aaaaacagat gcaattcccg gacgtctaaa  1140
ccaaaccact ttcaccgcta cacgaccggg ggtatactac ggtcaatgct ctgaaatctg  1200
tggagcaaac cacagtttca tgcccatcgt cctagaatta ttcccctaa aaatctttga  1260
aatagggccc gtatttaccc tatagcaccc cctctacccc ctctagagcc cactgtaaag  1320
ctaacttagc attaaccttt taagttaaag attaagagaa ccaacacctc tttacagtga  1380
aatgccccaa ctaaatacta ccgtatggcc caccataatt ccccctatac tccttacact  1440
attcctcatc acccaactaa aaatattaaa cacaaactac cacctacctc cctcaccaaa  1500
gcccataaaa ataaaaaatt ataacaaacc ctgagaacca aaatgaacga aatctgttcc  1560
gcttcattca ttgcccccac aatcctaggc ctacccgccg cagtactgat cattctattt  1620
cccccctctat tgatccccac ctccaaatat tcatcatcaaca accgactaat caccacccaa  1680
caatgactaa tcaaactaac ctcaaaacaa atgataacca tacacaacac taaaggacga  1740
acctgatctc ttatactagt atccttaatc atttttattg ccacaactaa cctcctcgga  1800
ctcctgcctc actcatttac accaaccacc caactatcta taaacctagc catggccatc  1860
cccttatgag cgggcgcagt gattataggc tttcgctcta agattaaaaa tgccctagcc  1920
cacttcttac cacaaggcac acctacaccc cttatccca tactagttat tatcgaaacc  1980
```

-continued

| Sequence table | | | | | |
|---|---|---|---|---|---|
| atcagcctac | tcattcaacc | aatagccctg | gccgtacgcc | taaccgctaa | cacttctact 2040 |
| gggcggtttt | atgdacagca | agcgaaccgg | aattgccagc | tggggcgccc | tctggtaagg 2100 |
| ttgggaagcc | ctgcaaagta | aactggatgg | ctttcttgcc | gccaaggatc | tgatggcgca 2160 |
| ggggatcaag | ctctgatcaa | gagacaggat | gaggatcgtt | tcgcatgatt | gaacaagatg 2220 |
| gattgcacgc | aggttctccg | gccgcttggg | tggagaggct | attcggctat | gactgggcac 2280 |
| aacagacaat | cggctgctct | gatgccgccg | tgttccggct | gtcagcgcag | gggcgcccgg 2340 |
| ttcttttgt | caagaccgac | ctgtccggtg | ccctgaatga | actgcaagac | gaggcagcgc 2400 |
| ggctatcgtg | gctggccacg | acgggcgttc | cttgcgcagc | tgtgctcgac | gttgtcactg 2460 |
| aagcgggaag | ggactggctg | ctattgggcg | aagtgccggg | caggatctc | ctgtcatctc 2520 |
| accttgctcc | tgccgagaaa | gtatccatca | tggctgatgc | aatgcggcgg | ctgcatacgc 2580 |
| ttgatccggc | tacctgccca | ttcgaccacc | aagcgaaaca | tcgcatcgag | cgagcacgta 2640 |
| ctcggatgga | agccggtctt | gtcgatcagg | atgatctgga | cgaagagcat | caggggctcg 2700 |
| cgccagccga | actgttcgcc | aggctcaagg | cgagcatgcc | cgacggcgag | gatctcgtcg 2760 |
| tgacccatgg | cgatgcctgc | ttgccgaata | tcatggtgga | aaatggccgc | ttttctggat 2820 |
| tcatcgactg | tggccggctg | ggtgtggcgg | accgctatca | ggacatagcg | ttggctaccc 2880 |
| gtgatattgc | tgaagagctt | ggcggcgaat | gggctgaccg | cttcctcgtg | ctttacggta 2940 |
| tcgccgctcc | cgattcgcag | cgcatcgcct | tctatcgcct | tcttgacgag | ttcttctgaa 3000 |
| ttattaacgc | ttacaatttc | ctgatgcggt | attttctcct | tacgcatctg | tgcggtattt 3060 |
| cacaccgcat | acaggtggca | cttttcgggg | aaatgtgcgc | ggaacccta | tttgtttatt 3120 |
| tttctaaata | cattcaaata | tgtatccgct | catgagacaa | taaccctgat | aaatgcttca 3180 |
| ataatagcac | gtgctaaaac | ttcatttta | atttaaaagg | atctaggtga | agatcctttt 3240 |
| tgataatctc | atgaccaaaa | tcccttaacg | tgagttttcg | ttccactgag | cgtcagaccc 3300 |
| cgtagaaaag | atcaaaggat | cttcttgaga | tcctttttt | ctgcgcgtaa | tctgctgctt 3360 |
| gcaaacaaaa | aaaccaccgc | taccagcggt | ggtttgtttg | ccggatcaag | agctaccaac 3420 |
| tcttttccg | aaggtaactg | gcttcagcag | agcgcagata | ccaaatactg | tccttctagt 3480 |
| gtagccgtag | ttaggccacc | acttcaagaa | ctctgtagca | ccgcctacat | acctcgctct 3540 |
| gctaatcctg | ttaccagtgg | ctgctgccag | tggcgataag | tcgtgtctta | ccgggttgga 3600 |
| ctcaagacga | tagttaccgg | ataaggcgca | gcggtcgggc | tgaacggggg | gttcgtgcac 3660 |
| acagcccagc | ttggagcgaa | cgacctacac | cgaactgaga | tacctacagc | gtgagctatg 3720 |
| agaaagcgcc | acgcttcccg | aagggagaaa | ggcggacagg | tatccggtaa | gcggcagggt 3780 |
| cggaacagga | gagcgcacga | gggagcttcc | aggggggaaac | gcctggtatc | tttatagtcc 3840 |
| tgtcgggttt | cgccacctct | gacttgagcg | tcgatttttt | tgatgctcgt | caggggggcg 3900 |
| gagcctatgg | aaaaacgcca | gcaacgcggc | cttttacgg | ttcctgggct | tttgctggcc 3960 |
| ttttgctcac | atgactt | | | | 3978 |

<210> 9
<211> 2097
<212> DNA
<213> Artificial Sequence
<220>
<223> nucleotide sequence of pMVA-5
<400> 9

| | | | | | |
|---|---|---|---|---|---|
| gctgcttcgc | gatgtacggg | ccagatatac | gcccattat | tcctagaacc | aggcgacctg 60 |
| cgactccttg | acgttgacaa | tcgagtagta | ctcccgattg | aagcccccat | tcgtataata 120 |
| attacatcac | aagacgtctt | gcactcatga | gccttctact | gggcggtttt | atggacagca 180 |
| agcgaaccgg | aattgccagc | tggggcgccc | tctggtaagg | ttgggaagcc | ctgcaaagta 240 |
| aactggatgg | ctttcttgcc | gccaaggatc | tgatggcgca | ggggatcaag | ctctgatcaa 300 |
| gagacaggat | gaggatcgtt | tcgcatgatt | gaacaagatg | gattgcacgc | aggttctccg 360 |
| gccgcttggg | tggagaggct | attcggctat | gactgggcac | aacagacaat | cggctgctct 420 |
| gatgccgccg | tgttccggct | gtcagcgcag | gggcgcccgg | ttcttttgt | caagaccgac 480 |
| ctgtccggtg | ccctgaatga | actgcaagac | gaggcagcgc | ggctatcgtg | gctggccacg 540 |
| acgggcgttc | cttgcgcagc | tgtgctcgac | gttgtcactg | aagcgggaag | ggactggctg 600 |
| ctattgggcg | aagtgccggg | caggatctc | ctgtcatctc | accttgctcc | tgccgagaaa 660 |
| gtatccatca | tggctgatgc | aatgcggcgg | ctgcatacgc | ttgatccggc | tacctgccca 720 |
| ttcgaccacc | aagcgaaaca | tcgcatcgag | cgagcacgta | ctcggatgga | agccggtctt 780 |
| gtcgatcagg | atgatctgga | cgaagagcat | caggggctcg | cgccagccga | actgttcgcc 840 |
| aggctcaagg | cgagcatgcc | cgacggcgag | gatctcgtcg | tgacccatgg | cgatgcctgc 900 |
| ttgccgaata | tcatggtgga | aaatggccgc | ttttctggat | tcatcgactg | tggccggctg 960 |
| ggtgtggcgg | accgctatca | ggacatagcg | ttggctaccc | gtgatattgc | tgaagagctt 1020 |
| ggcggcgaat | gggctgaccg | cttcctcgtg | ctttacggta | tcgccgctcc | cgattcgcag 1080 |
| cgcatcgcct | tctatcgcct | tcttgacgag | ttcttctgaa | ttattaacgc | ttacaatttc 1140 |
| ctgatgcggt | attttctcct | tacgcatctg | tgcggtattt | cacaccgcat | acaggtggca 1200 |
| cttttcgggg | aaatgtgcgc | ggaacccctat | ttgtttattt | ttctaaatac | attcaaatat 1260 |
| gtatccgctc | atgagacaat | aaccctgata | aatgcttcaa | taatagcacg | tgctaaaact 1320 |
| tcatttttaa | tttaaaagga | tctaggtgaa | gatcctttt | gataatctca | tgaccaaaat 1380 |
| cccttaacgt | gagttttcgt | tccactgagc | gtcagacccc | gtagaaaaga | tcaaaggatc 1440 |
| ttcttgagat | cctttttc | tgcgcgtaat | ctgctgcttg | caaacaaaaa | aaccaccgct 1500 |
| accagcggtg | gtttgtttgc | cggatcaaga | gctaccaact | cttttccga | aggtaactgg 1560 |
| cttcagcaga | gcgcagatac | caaatactgt | tcttctagtg | tagccgtagt | taggccacca 1620 |
| cttcaagaac | tctgtagcac | cgcctacata | cctcgctctg | ctaatcctgt | taccagtggc 1680 |
| tgctgccagt | ggcgataagt | cgtgtcttac | cgggttggac | tcaagacgat | agttaccgga 1740 |
| taaggcgcag | cggtcgggct | gaacggggg | ttcgtgcaca | cagcccagct | tggagcgaac 1800 |
| gacctacacc | gaactgagat | acctacagcg | tgagctatga | gaaagcgcca | cgcttccga 1860 |
| agggagaaag | gcggacaggt | atccggtaag | cggcagggtc | ggaacaggag | agcgcacgag 1920 |
| ggagcttcca | gggggaaacg | cctggtatct | ttatagtcct | gtcgggtttc | gccacctctg 1980 |
| acttgagcgt | cgatttttgt | gatgctcgtc | aggggggcgg | agcctatgga | aaaacgccag 2040 |
| caacgcggcc | ttttacggt | tcctggcctt | ttgctggcct | tttgctcaca | tgactt 2097 |

```
                          Sequence table

<210> 10
<211> 2577
<212> DNA
<213> Artificial Sequence
<220>
<223> nucleotide sequence of pMVA-6
<400> 10
gctgcttcgc gatgtacggg ccagatatac gcctgaacta tcctgcccgc catcatccta    60
gtcctcatcg ccctcccatc cctacgcatc cttacataa cagacgaggt caacgattcc   120
tcccttacca tcaaatcaat tggccaccaa tggtactgaa cctacgagta caccgactac   180
ggcggactaa tcttcaactc ctacatactt ccccattat tcctagaacc aggcgacctg   240
cgactccttg acgttgacaa tcgagtagta ctcccgattg aagcccccat tcgtataata   300
attacatcac aagacgtctt gcactcatga gctgtcccca cattaggctt aaaaacagat   360
gcaattcccg gacgtctaaa ccaaaccact ttcaccgcta cacgaccggg ggtatactac   420
ggtcaatgct ctgaaatctg tggagcaaac cacagtttca tgcccatcgt cctagaatta   480
attcccctaa aaatctttga aatagggccc gtatttaccc tatagcaccc cctctaccct   540
ctctagagcc cactgtaaag ctaacttagc attaaccttt taagttaaag attaagagaa   600
ccaacacctc tttacagtga aatgcccaa ctcttctact gggcggtttt atggacagca   660
agcgaaccgg aattgccagc tggggcgccc tctggtaagg ttgggaagcc ctgcaaagta   720
aactggatgg ccttcttgcc gccaaggatc tgatggcgca ggggatcaag ctctgatcaa   780
gagacaggat gaggatcgtt tcgcatgatt gaacaagatg gattgcacgc aggttcttcg   840
gccgcttggg tggagaggct attcggctat gactgggcac aacagacaat cggctgctct   900
gatgccgccg tgttccggct gtcagccgag gggcgcccgg ttcttttttgt caagaccgac   960
ctgtccggtg ccctgaatga actgcaagac gaggcagcgc ggctatcgtg gctggccacg  1020
acgggcgttc cttgcgcagc tgtgctcgac gttgtcactg aagcgggaag ggactggctg  1080
ctattgggcg aagtgccggg gcaggatctc ctgtcatctc accttgctcc tgccgagaaa  1140
gtatccatca tggctgatgc aatgcggcgg ctgcatacgc ttgatccgac tacctgccca  1200
ttcgaccacc aagcgaaaca tcgcatcgag cgagcacgta ctcggatgga agccggtctt  1260
gtcgatcagg atgatctgga cgaagagcat caggggctcg cgccagccga actgttcgcc  1320
aggctcaagg cgagcatgcc cgacggcgag gatctcgtcg tgacccatgg cgatgcctgc  1380
ttgccgaata tcatggtgga aaatggccgc ttttctggat tcatcgactg tggccggctg  1440
ggtgtggcgg accgctatca ggacatagcg ttggctaccc gtgatattgc tgaagagctt  1500
ggcggcgaat gggctgaccg cttcctcgtg ctttacggta tcgccgctcc cgattcgcag  1560
cgcatcgcct tctatcgcct tcttgacgag ttcttctgaa ttattaacgc ttacaatttc  1620
ctgatgcggt attttctcct tacgcatctg tgcggtattt cacaccgcat caggtggcac  1680
ttttcgggga aatgtgcgcg gaaccctat ttgttttattt ttctaaatac attcaaatat  1740
gtatccgctc atgagacaat aaccctgata aatgcttcaa taatagcacg tgctaaaact  1800
tcatttttaa tttaaaagga tctaggtgaa gatcctttt gataatctca tgaccaaaat  1860
cccttaacgt gagttttcgt tccactgagc gtcagacccc gtagaaaaga tcaaaggatc  1920
ttcttgagat cctttttttc tgcgcgtaat ctgctgcttg caaacaaaaa aaccaccgct  1980
accagcggtg gtttgtttgc cggatcaaga gctaccaact ctttttccga aggtaactgg  2040
cttcagcaga gcgcagatac caaatactgt tcttctagtg tagccgtagt taggccacca  2100
cttcaagaac tctgtagcac cgcctacata cctcgctctg ctaatcctgt taccagtggc  2160
tgctgccagt ggcgataagt cgtgtcttac cgggttggac tcaagacgat agttaccgga  2220
taaggcgcag cggtcgggct gaacgggggg ttcgtgcaca cagcccagct tggagcgaac  2280
gacctacacc gaactgagat acctacagcg tgagctatga gaaagcgcca cgcttcccga  2340
agggagaaag gcggacaggt atccggtaag cggcagggtc ggaacaggag agcgcacgag  2400
ggagcttcca gggggaaacg cctggtatct ttatagtcct gtcgggtttc gccacctctg  2460
acttgagcgt cgatttttgt gatgctcgtc aggggggcgg agcctatgga aaaacgccag  2520
caacgcggcc tttttacggt tcctggcctt ttgctggcct tttgctcaca tgactt      2577

<210> 11
<211> 3977
<212> DNA
<213> Artificial Sequence
<220>
<223> nucleotide sequence of pMVA-7
<400> 11
gctgcttcgc gatgtacggg ccagatatac gctacgttgt agctcacttc cactatgtcc    60
tatcaatagg agctgtattt gccatcatag gaggcttcat tcactgattt cccctattct   120
caggctacac cctagaccaa acctacgcca aaatcattt cactatcata ttcatcggcg   180
taaatctaac tttcttccca caacacttc tcggcctatc cggaatgccc cgacgttact   240
cggactaccc cgatgcatac accacatgaa acatcctatc atctgtaggc tcattcattt   300
ctctaacagc agtaatatta ataattttca tgatttgaga agccttcgct tcgaagcgaa   360
aagtcctaat agtagaagaa ccctccataa acctggagtg actatatgga tgcccccac   420
cctaccacac attcgaagaa cccgtataca taaaatctag acaaaaaagg aaggaatcga   480
accccccaaa gctggtttca agccaacccc atggcctcca tgactttttc aaaaaggtat   540
tagaaaaacc atttcataac tttgtcaaag ttaaattata ggctaaatcc tatatatctt   600
aatggcacat gcagcgcaag taggtctaca agacgctact tcccctatca tagaagagct   660
tatcaccttt catgatcacg ccctcataat cattttcctt atctgcttcc tagtcctgta   720
tgccctttc ctaacactca caacaaaact aactaatact aacatctcag acgctcagga   780
aatagaaaacc gtctgaacta tcctgcccgc catcatccta gtcctcatcg ccctcccatc   840
cctacgcatc ctttacataa cagacgaggt caacgatccc tcccttacca tcaaatcaat   900
tggccaccaa tggtactgaa cctacgagta caccgactac ggcggactaa tcttcaactc   960
ctacatactt ccccattat tcctagaacc aggcgacctg cgactccttg acgttgacaa  1020
tcgagtagta ctcccgattg aagcccccat tcgtataata attacatcac aagacgtctt  1080
```

| Sequence table | | | | |
|---|---|---|---|---|
| gcactcatga | gctgtcccca | cattaggctt | aaaaacagat | gcaattcccg gacgtctaaa 1140 |
| ccaaaccact | ttcaccgcta | cacgaccggg | ggtatactac | ggtcaatgct ctgaaatctg 1200 |
| tggagcaaac | cacagtttca | tgcccatcgt | cctagaatta | attcccctaa aaatctttga 1260 |
| aatagggccc | gtatttaccc | tatagcaccc | cctttacccc | ctctagagcc cactgtaaag 1320 |
| ctaacttagc | attaaccttt | taagttaaag | attaagagaa | ccaacacctc tttacagtga 1380 |
| aatgccccaa | ctaaatacta | ccgtatggcc | caccataatt | accccatac tccttacact 1440 |
| attcctcatc | acccaactaa | aaatattaaa | cacaaactac | cacctacctc cctcaccaaa 1500 |
| gcccataaaa | ataaaaaatt | ataacaaacc | ctgagaacca | aaatgaacga aaatctgttc 1560 |
| gcttcattca | ttgccccccac | aatcctaggc | ctacccgccg | cagtactgat cattctattt 1620 |
| cccctctat | tgatccccac | ctccaaatat | ctcatcaaca | accgactaat caccacccaa 1680 |
| caatgactaa | tcaaactaac | ctcaaaacaa | atgataacca | tacacaacac taaaggacga 1740 |
| acctgatctc | ttatactagt | atccttaatc | atttttattg | ccacaactaa cctcctcgga 1800 |
| ctcctgcctc | actcatttac | accaaccacc | caactatcta | taaacctagc catggccatc 1860 |
| cccttatgag | cgggcgcagt | gattataggc | tttcgcttta | agattaaaaa tgccctagcc 1920 |
| cacttcttac | cacaaggcac | acctacaccc | cttatcccca | tactagttat tatcgaaacc 1980 |
| atcagcctac | tcattcaacc | aatagccctg | gccgtacgcc | taaccgctaa cacttctact 2040 |
| gggcggtttt | atggacagca | agcgaaccgg | aattgccagc | tggggcgccc tctggtaagg 2100 |
| ttgggaagcc | ctgcaaagta | aactggatgg | ctttctcgcc | gccaaggatc tgatggcgca 2160 |
| ggggatcaag | ctctgatcaa | gagacaggat | gaggatcgtt | tcgcatgatt gaacaagatg 2220 |
| gattgcacgc | aggttctccg | gccgcttggg | tggagaggct | attcggctat gactgggcac 2280 |
| aacagacaat | cggctgctct | gatgccgccg | tgttccggct | gtcagcgcag gggcgcccgg 2340 |
| ttcttttttgt | caagaccgac | ctgtccggtg | ccctgaatga | actgcaagac gaggcagcgc 2400 |
| ggctatcgtg | gctggccacg | acgggcgttc | cttgcgcagc | tgtgctcgac gttgtcactg 2460 |
| aagcgggaag | ggactggctg | ctattgggcg | aagtgccggg | gcaggatctc ctgtcatctc 2520 |
| accttgctcc | tgccgagaaa | gtatccatca | tggctgatgc | aatgcggcgg ctgcatacgc 2580 |
| ttgatccggc | tacctgccca | ttcgaccacc | aagcgaaaca | tcgcatcgag cgagcacgta 2640 |
| ctcggatgga | agccggtctt | gtcgatcagg | atgatctgga | cgaagagcat caggggctcg 2700 |
| cgccagccga | actgttcgcc | aggctcaagg | cgagcatgcc | cgacggcgag gatctcgtcg 2760 |
| tgacccatgg | cgatgcctgc | ttgccgaata | tcatggtgga | aaatggccgc ttttctggat 2820 |
| tcatcgactg | tggccggctg | ggtgtggcgg | accgctatca | ggacatagcg ttggctaccc 2880 |
| gtgatattgc | tgaagagctt | ggcggcgaat | gggctgaccg | cttcctcgtg ctttacggta 2940 |
| tcgccgctcc | cgattcgcag | cgcatcgcct | tctatcgcct | tcttgacgag ttcttctgaa 3000 |
| ttattaacgc | ttacaatttc | ctgatgcggt | attttctcct | tacgcatctg tgcggtattt 3060 |
| cacaccgcat | caggtggcac | ttttcgggga | aatgtgcgcg | gaacctctat ttgtttattt 3120 |
| ttctaaatac | attcaaatat | gtatccgctc | atgagacaat | aaccctgata aatgcttcaa 3180 |
| taatagcacg | tgctaaaact | tcatttttaa | tttaaaagga | tctaggtgaa gatccttttt 3240 |
| gataatctca | tgaccaaaat | cccttaacgt | gagttttcgt | tccactgagc gtcagaccc 3300 |
| gtagaaaaga | tcaaaggatc | ttcttgagat | cctttttttc | tgcgcgtaat ctgctgcttg 3360 |
| caaacaaaaa | aaccaccgct | accagcggtg | gtttgtttgc | cggatcaaga gctaccaact 3420 |
| cttttccga | aggtaactgg | cttcagcaga | gcgcagatac | caaatactgt tcttctagtg 3480 |
| tagccgtagt | taggccacca | cttcaagaac | tctgtagcac | cgcctacata cctcgctctg 3540 |
| ctaatcctgt | taccagtggc | tgctgccagt | ggcgataagt | cgtgtcttac cgggttggac 3600 |
| tcaagacgat | agttaccgga | taaggcgcag | cggtcgggct | gaacggggg ttcgtgcaca 3660 |
| cagcccagct | tggagcgaac | gacctacacc | gaactgagat | acctacagcg tgagctatga 3720 |
| gaaagcgcca | cgcttcccga | agggagaaag | gcggacaggt | atccgtaag cggcaggtc 3780 |
| ggaacaggag | agcgcacgag | ggagcttcca | gggggaaacg | cctggtatct ttatagtcct 3840 |
| gtcgggtttc | gccacctctg | acttgagcgt | cgatttttgt | gatgctcgtc aggggggcgg 3900 |
| agcctatgga | aaaacgccag | caacgcggcc | ttttacggt | tcctggcctt ttgctggcct 3960 |
| tttgctcaca | tgactt | | | 3977 |

SEQUENCE LISTING

<160> NUMBER OF SEQ ID NOS: 11

<210> SEQ ID NO 1
<211> LENGTH: 1978
<212> TYPE: DNA
<213> ORGANISM: Artificial Sequence
<220> FEATURE:
<223> OTHER INFORMATION: nucleotide sequence of pMVA

<400> SEQUENCE: 1
gactcttcgc gatgtacggg ccagatatac gccttctact gggcggtttt atggacagca     60
agcgaaccgg aattgccagc tggggcgccc tctggtaagg ttgggaagcc ctgcaaagta    120
aactggatgg ctttctcgcc gccaaggatc tgatggcgca ggggatcaag ctctgatcaa    180
gagacaggat gaggatcgtt tcgcatgatt gaacaagatg gattgcacgc aggttctccg    240
gccgcttggg tggagaggct attcggctat gactgggcac aacagacaat cggctgctct    300

```
gatgccgccg tgttccggct gtcagcgcag gggcgcccgg ttcttttttgt caagaccgac    360 ctgtccggtg ccctgaatga actgcaagac gaggcagcgc ggctatcgtg gctggccacg    420
acgggcgttc cttgcgcagc tgtgctcgac gttgtcactg aagcgggaag ggactggctg    480
ctattgggcg aagtgccggg gcaggatctc ctgtcatctc accttgctcc tgccgagaaa    540
gtatccatca tggctgatgc aatgcggcgg ctgcatacgc ttgatccggc tacctgccca    600
ttcgaccacc aagcgaaaca tcgcatcgag cgagcacgta ctcggatgga agccggtctt    660
gtcgatcagg atgatctgga cgaagagcat caggggctcg cgccagccga actgttcgcc    720
aggctcaagg cgagcatgcc cgacggcgag gatctcgtcg tgacccatgg cgatgcctgc    780
ttgccgaata tcatggtgga aaatggccgc ttttctggat tcatcgactg tggccggctg    840
ggtgtggcgg accgctatca ggacatagcg ttggctaccc gtgatattgc tgaagagctt    900
ggcggcgaat gggctgaccg cttcctcgtg ctttacggta tcgccgctcc cgattcgcag    960
cgcatcgcct tctatcgcct tcttgacgag ttccttctga ttattaacgc ttacaatttc   1020
ctgatgcggt atttctcct tacgcatctg tgcggtattt cacaccgcat acaggtggca   1080
cttttcgggg aaatgtgcgc ggaaccccta tttgtttatt tttctaaata cattcaaata   1140
tgtatccgct catgagacaa taaccctgat aaatgcttca ataatagcac gtgctaaaac   1200 ttcatttta atttaaaagg atctaggtga agatcctttt tgataatctc atgaccaaaa   1260
tcccttaacg tgagttttcg ttccactgag cgtcagaccc cgtagaaaag atcaaaggat   1320
cttcttgaga tcctttttt ctgcgcgtaa tctgctgctt gcaaacaaaa aaaccaccgc   1380
taccagcggt ggtttgtttg ccggatcaag agctaccaac tctttttccg aaggtaactg   1440
gcttcagcag agcgcagata ccaaatactg tccttctagt gtagccgtag ttaggccacc   1500
acttcaagaa ctctgtagca ccgcctacat acctcgctct gctaatcctg ttaccagtgg   1560
ctgctgccag tggcgataag tcgtgtctta ccgggttgga ctcaagacga tagttaccgg   1620
ataaggcgca gcggtcgggc tgaacggggg gttcgtgcac acagcccagc ttggagcgaa   1680
cgacctacac cgaactgaga tacctacagc gtgagctatg agaaagcgcc acgcttcccg   1740
aagggagaaa ggcggacagg tatccggtaa gcggcagggt cggaacagga gagcgcacga   1800
gggagcttcc agggggaaac gcctggtatc tttatagtcc tgtcgggttt cgccacctct   1860
gacttgagcg tcgatttttg tgatgctcgt cagggggggcg gagcctatgg aaaaacgcca   1920
gcaacgcggc ctttttacgg ttcctgggct tttgctggcc ttttgctcac atgttctt     1978

<210> SEQ ID NO 2
<211> LENGTH: 1977
<212> TYPE: DNA
<213> ORGANISM: Artificial Sequence
<220> FEATURE:
<223> OTHER INFORMATION: nucleotide sequence of pMVA-1

<400> SEQUENCE: 2
gctgcttcgc gatgtacggg ccagatatac gccttctact gggcggtttt atggacagca     60
agcgaaccgg aattgccagc tggggcgccc tctggtaagg ttgggaagcc ctgcaaagta    120
aactggatgg ctttcttgcc gccaaggatc tgatggcgca gggatcaag ctctgatcaa     180 agacaggat gaggatcgtt tcgcatgatt gaacaagatg gattgcacgc aggttctccg    240
gccgcttggg tggagaggct attcggctat gactgggcac aacagacaat cggctgctct    300
gatgccgccg tgttccggct gtcagcgcag gggcgcccgg ttcttttttgt caagaccgac    360 ctgtccggtg ccctgaatga actgcaagac gaggcagcgc ggctatcgtg gctggccacg    420
```

```
acgggcgttc cttgcgcagc tgtgctcgac gttgtcactg aagcgggaag ggactggctg    480
ctattgggcg aagtgccggg gcaggatctc ctgtcatctc accttgctcc tgccgagaaa    540
gtatccatca tggctgatgc aatgcggcgg ctgcatacgc ttgatccggc tacctgccca    600
ttcgaccacc aagcgaaaca tcgcatcgag cgagcacgta ctcggatgga agccggtctt    660
gtcgatcagg atgatctgga cgaagagcat caggggctcg cgccagccga actgttcgcc    720
aggctcaagg cgagcatgcc cgacggcgag gatctcgtcg tgacccatgg cgatgcctgc    780
ttgccgaata tcatggtgga aaatggccgc ttttctggat tcatcgactg tggccggctg    840
ggtgtggcgg accgctatca ggacatagcg ttggctaccc gtgatattgc tgaagagctt    900
ggcggcgaat gggctgaccg cttcctcgtg ctttacggta tcgccgctcc cgattcgcag    960
cgcatcgcct tctatcgcct tcttgacgag ttccttctga attattaacgc ttacaatttc   1020 ctgatgcggt attttctcct tacgcatctg tgcggtattt cacaccgcat caggtggcac   1080
ttttcgggga aatgtgcgcg gaacccctat ttgtttattt ttctaaatac attcaaatat   1140
gtatccgctc atgagacaat aaccctgata aatgcttcaa taatagcacg tgctaaaact   1200
tcatttttaa tttaaaagga tctaggtgaa gatccttttt gataatctca tgaccaaaat   1260
cccttaacgt gagttttcgt tccactgagc gtcagacccc gtagaaaaga tcaaaggatc   1320
ttcttgagat ccttttttc tgcgcgtaat ctgctgcttg caaacaaaaa accaccgct   1380 accagcggtg gtttgtttgc cggatcaaga gctaccaact cttttttccga aggtaactgg   1440 cttcagcaga gcgcagatac caaatactgt tcttctagtg tagccgtagt taggccacca   1500
cttcaagaac tctgtagcac cgcctacata cctcgctctg ctaatcctgt taccagtggc   1560
tgctgccagt ggcgataagt cgtgtcttac cgggttggac tcaagacgat agttaccgga   1620
taaggcgcag cggtcgggct gaacggggg ttcgtgcaca cagcccagct tggagcgaac   1680
gacctacacc gaactgagat acctacagcg tgagctatga aaagcgcca cgcttcccga   1740 agggagaaag gcggacaggt atccggtaag cggcagggtc ggaacaggag agcgcacgag   1800
ggagcttcca gggggaaacg cctggtatct ttatagtcct gtcgggtttc gccacctctg   1860
acttgagcgt cgattttgt gatgctcgtc aggggggcgg agcctatgga aaaacgccag   1920
caacgcggcc ttttacggtt cctggccttt tgctggcct tttgctcaca tgttctt       1977
```

<210> SEQ ID NO 3
<211> LENGTH: 120
<212> TYPE: DNA
<213> ORGANISM: Artificial Sequence
<220> FEATURE:
<223> OTHER INFORMATION: nucleotide sequence of mtDNA

<400> SEQUENCE: 3

```
cccattattc ctagaaccag gcgacctgcg actccttgac gttgacaatc gagtagtact     60
cccgattgaa gccccattc gtataataat tacatcacaa gacgtcttgc actcatgagc    120
```

<210> SEQ ID NO 4
<211> LENGTH: 600
<212> TYPE: DNA
<213> ORGANISM: Artificial Sequence
<220> FEATURE:
<223> OTHER INFORMATION: nucleotide sequence 2 of mtDNA

<400> SEQUENCE: 4

```
ctgaactatc ctgcccgcca tcatcctagt cctcatcgcc ctcccatccc tacgcatcct     60
```

```
ttacataaca gacgaggtca acgatccctc ccttaccatc aaatcaattg gccaccaatg    120
gtactgaacc tacgagtaca ccgactacgg cggactaatc ttcaactcct acatacttcc    180
cccattattc ctagaaccag gcgacctgcg actccttgac gttgacaatc gagtagtact    240
cccgattgaa gcccccattc gtataataat tacatcacaa gacgtcttgc actcatgagc    300
tgtccccaca ttaggcttaa aaacagatgc aattcccgga cgtctaaacc aaaccacttt    360
caccgctaca cgaccggggg tatactacgg tcaatgctct gaaatctgtg agcaaaacca    420
cagtttcatg cccatcgtcc tagaattaat tcccctaaaa atctttgaaa tagggcccgt    480
atttacccta tagcaccccc tctacccccct ctagagccca ctgtaaagct aacttagcat    540 taaccttta agttaaagat taagagaacc aacacctctt tacagtgaaa tgccccaact    600
```

<210> SEQ ID NO 5
<211> LENGTH: 2000
<212> TYPE: DNA
<213> ORGANISM: Artificial Sequence
<220> FEATURE:
<223> OTHER INFORMATION: nucleotide sequence 3 of mtDNA

<400> SEQUENCE: 5

```
tacgttgtag ctcacttcca ctatgtccta tcaataggag ctgtatttgc catcatagga     60
ggcttcattc actgatttcc cctattctca ggctacaccc tagaccaaac ctacgccaaa    120
atccatttca ctatcatatt catcggcgta aatctaactt tcttcccaca cactttctc    180 ggcctatccg gaatgccccg acgttactcg gactaccccg atgcatacac cacatgaaac    240
atcctatcat ctgtaggctc attcatttct ctaacagcag taatattaat aattttcatg    300
atttgagaag ccttcgcttc gaagcgaaaa gtcctaatag tagaagaacc ctccataaac    360
ctggagtgac tatatggatg ccccccaccc taccacacat tcgaagaacc cgtatacata    420
aaatctagac aaaaaaggaa ggaatcgaac cccccaaagc tggtttcaag ccaaccccat    480
ggcctccatg acttttttcaa aaaggtatta gaaaaaccat ttcataactt tgtcaaagtt    540
aaattatagg ctaaatccta tatatcttaa tggcacatgc agcgcaagta ggtctacaag    600
acgctacttc ccctatcata gaagagctta tcaccttttca tgatcacgcc tcataatca    660 ttttccttat ctgcttccta gtcctgtatg ccctttttcct aacactcaca acaaaactaa    720
ctaatactaa catctcagac gctcaggaaa tagaaaccgt ctgaactatc ctgcccgcca    780
tcatcctagt cctcatcgcc ctcccatccc tacgcatcct ttacataaca gacgaggtca    840
acgatccctc ccttaccatc aaatcaattg gccaccaatg gtactgaacc tacgagtaca    900
ccgactacgg cggactaatc ttcaactcct acatacttcc cccattattc ctagaaccag    960
gcgacctgcg actccttgac gttgacaatc gagtagtact cccgattgaa gcccccattc   1020
gtataataat tacatcacaa gacgtcttgc actcatgagc tgtccccaca ttaggcttaa   1080
aaacagatgc aattcccgga cgtctaaacc aaaccacttt caccgctaca cgaccggggg   1140
tatactacgg tcaatgctct gaaatctgtg agcaaaacca cagtttcatg cccatcgtcc   1200
tagaattaat tcccctaaaa atctttgaaa tagggcccgt atttacccta tagcaccccc   1260 tctacccccct ctagagccca ctgtaaagct aacttagcat taacctttta agttaaagat   1320
taagagaacc aacacctctt tacagtgaaa tgccccaact aaatactacc gtatggccca   1380
ccataattac ccccatactc cttacactat tcctcatcac ccaactaaaa atattaaaca   1440
caaactacca cctacctccc tcaccaaagc ccataaaaat aaaaaattat aacaaaccct   1500
gagaaccaaa atgaacgaaa atctgttcgc ttcattcatt gcccccacaa tcctaggcct   1560
```

-continued

| | |
|---|---|
| acccgccgca gtactgatca ttctatttcc ccctctattg atccccacct ccaaatatct | 1620 |
| catcaacaac cgactaatca ccacccaaca atgactaatc aaactaacct caaaacaaat | 1680 |
| gataaccata cacaacacta aaggacgaac ctgatctctt atactagtat ccttaatcat | 1740 |
| ttttattgcc acaactaacc tcctcggact cctgcctcac tcatttacac caaccaccca | 1800 |
| actatctata aacctagcca tggccatccc cttatgagcg ggcgcagtga ttataggctt | 1860 |
| tcgctctaag attaaaaatg ccctagccca cttcttacca caaggcacac ctacacccct | 1920 |
| tatccccata ctagttatta tcgaaaccat cagcctactc attcaaccaa tagccctggc | 1980 |
| cgtacgccta accgctaaca | 2000 |

<210> SEQ ID NO 6
<211> LENGTH: 2098
<212> TYPE: DNA
<213> ORGANISM: Artificial Sequence
<220> FEATURE:
<223> OTHER INFORMATION: nucleotide sequence of pMVA-2

<400> SEQUENCE: 6

| | |
|---|---|
| gactcttcgc gatgtacggg ccagatatac gccccattat tcctagaacc aggcgacctg | 60 |
| cgactccttg acgttgacaa tcgagtagta ctcccgattg aagcccccat tcgtataata | 120 |
| attacatcac aagacgtctt gcactcatga gccttctact gggcggtttt atggacagca | 180 |
| agcgaaccgg aattgccagc tggggcgccc tctggtaagg ttgggaagcc ctgcaaagta | 240 |
| aactggatgg ctttctcgcc gccaaggatc tgatggcgca ggggatcaag ctctgatcaa | 300 |
| gagacaggat gaggatcgtt tcgcatgatt gaacaagatg gattgcacgc aggttctccg | 360 |
| gccgcttggg tggagaggct attcggctat gactgggcac aacagacaat cggctgctct | 420 |
| gatgccgccg tgttccggct gtcagcgcag gggcgcccgg ttcttttttgt caagaccgac | 480 |
| ctgtccggtg ccctgaatga actgcaagac gaggcagcgc ggctatcgtg gctggccacg | 540 |
| acgggcgttc cttgcgcagc tgtgctcgac gttgtcactg aagcgggaag ggactggctg | 600 |
| ctattgggcg aagtgccggg gcaggatctc ctgtcatctc accttgctcc tgccgagaaa | 660 |
| gtatccatca tggctgatgc aatgcggcgg ctgcatacgc ttgatccggc tacctgccca | 720 |
| ttcgaccacc aagcgaaaca tcgcatcgag cgagcacgta ctcggatgga agccggtctt | 780 |
| gtcgatcagg atgatctgga cgaagagcat caggggctcg cgccagccga actgttcgcc | 840 |
| aggctcaagg cgagcatgcc cgacggcgag gatctcgtcg tgacccatgg cgatgcctgc | 900 |
| ttgccgaata tcatggtgga aaatggccgc ttttctggat tcatcgactg tggccggctg | 960 |
| ggtgtggcgg accgctatca ggacatagcg ttggctaccc gtgatattgc tgaagagctt | 1020 |
| ggcggcgaat gggctgaccg cttcctcgtg ctttacggta tcgccgctcc cgattcgcag | 1080 |
| cgcatcgcct tctatcgcct tcttgacgag ttcttctgaa ttattaacgc ttacaatttc | 1140 |
| ctgatgcggt attttctcct tacgcatctg tgcggtattt cacaccgcat acaggtggca | 1200 |
| cttttcgggg aaatgtgcgc ggaacccctca tttgtttatt tttctaaata cattcaaata | 1260 |
| tgtatccgct catgagacaa taaccctgat aaatgcttca ataatagcac gtgctaaaac | 1320 |
| ttcattttta atttaaaagg atctaggtga agatcctttt tgataatctc atgaccaaaa | 1380 |
| tcccttaacg tgagttttcg ttccactgag cgtcagaccc cgtagaaaag atcaaaggat | 1440 |
| cttcttgaga tcctttttttt ctgcgcgtaa tctgctgctt gcaaacaaaa aaaccaccgc | 1500 |
| taccagcggt ggtttgtttg ccggatcaag agctaccaac tcttttttccg aaggtaactg | 1560 |

| | | |
|---|---|---|
| gcttcagcag agcgcagata ccaaatactg tccttctagt gtagccgtag ttaggccacc | 1620 | |
| acttcaagaa ctctgtagca ccgcctacat acctcgctct gctaatcctg ttaccagtgg | 1680 | |
| ctgctgccag tggcgataag tcgtgtctta ccgggttgga ctcaagacga tagttaccgg | 1740 | |
| ataaggcgca gcggtcgggc tgaacggggg gttcgtgcac acagcccagc ttggagcgaa | 1800 | |
| cgacctacac cgaactgaga tacctacagc gtgagctatg agaaagcgcc acgcttcccg | 1860 | |
| aagggagaaa ggcggacagg tatccggtaa gcggcagggt cggaacagga gagcgcacga | 1920 | |
| gggagcttcc aggggggaaac gcctggtatc tttatagtcc tgtcgggttt cgccacctct | 1980 | |
| gacttgagcg tcgatttttg tgatgctcgt caggggggcg agcctatgg aaaaacgcca | 2040 | |
| gcaacgcggc ctttttacgg ttcctgggct tttgctggcc ttttgctcac atgttctt | 2098 | |

<210> SEQ ID NO 7
<211> LENGTH: 2578
<212> TYPE: DNA
<213> ORGANISM: Artificial Sequence
<220> FEATURE:
<223> OTHER INFORMATION: nucleotide sequence of pMVA-3

<400> SEQUENCE: 7

| | | |
|---|---|---|
| gactcttcgc gatgtacggg ccagatatac gcctgaacta tcctgcccgc catcatccta | 60 | |
| gtcctcatcg ccctcccatc cctacgcatc ctttacataa cagacgaggt caacgatccc | 120 | |
| tcccttacca tcaaatcaat tggccaccaa tggtactgaa cctacgagta caccgactac | 180 | |
| ggcggactaa tcttcaactc ctacatactt cccccattat tcctagaacc aggcgacctg | 240 | |
| cgactccttg acgttgacaa tcgagtagta ctcccgattg aagcccccat tcgtataata | 300 | |
| attacatcac aagacgtctt gcactcatga gctgtcccca cattaggctt aaaaacagat | 360 | |
| gcaattcccg gacgtctaaa ccaaaccact ttcaccgcta cacgaccggg gtatactac | 420 | |
| ggtcaatgct ctgaaatctg tggagcaaac cacagtttca tgcccatcgt cctagaatta | 480 | |
| attccccctaa aaatctttga aataggggcc gtatttaccc tatagcaccc cctctacccc | 540 | |
| ctctagagcc cactgtaaag ctaacttagc attaaccttt taagttaaag attaagagaa | 600 | |
| ccaacacctc tttacagtga aatgcccccaa ctcttctact gggcggtttt atggacagca | 660 | |
| agcgaaccgg aattgccagc tggggcgccc tctggtaagg ttgggaagcc ctgcaaagta | 720 | |
| aactggatgg cttctcgcc gccaaggatc tgatggcgca ggggatcaag ctctgatcaa | 780 | |
| gagacaggat gaggatcgtt tcgcatgatt gaacaagatg gattgcacgc aggttctccg | 840 | |
| gccgcttggg tggagaggct attcggctat gactgggcac aacagacaat cggctgctct | 900 | |
| gatgccgccg tgttccggct gtcagcgcag gggcgcccgg ttcttttttgt caagaccgac | 960 | |
| ctgtccggtg ccctgaatga actgcaagac gaggcagcgc ggctatcgtg gctggccacg | 1020 | |
| acgggcgttc cttgcgcagc tgtgctcgac gttgtcactg aagcgggaag ggactggctg | 1080 | |
| ctattgggcg aagtgccggg gcaggatctc ctgtcatctc accttgctcc tgccgagaaa | 1140 | |
| gtatccatca tggctgatgc aatgcggcgg ctgcatacgc ttgatccggc tacctgccca | 1200 | |
| ttcgaccacc aagcgaaaca tcgcatcgag cgagcacgta ctcggatgga agccggtctt | 1260 | |
| gtcgatcagg atgatctgga cgaagagcat caggggctcg cgccagccga actgttcgcc | 1320 | |
| aggctcaagg cgagcatgcc cgacggcgag gatctcgtcg tgacccatgg cgatgcctgc | 1380 | |
| ttgccgaata tcatggtgga aaatggccgc ttttctggat tcatcgactg tggccggctg | 1440 | |
| ggtgtggcgg accgctatca ggacatagcg ttggctaccc gtgatattgc tgaagagctt | 1500 | |
| ggcggcgaat gggctgaccg cttcctcgtg ctttacggta tcgccgctcc cgattcgcag | 1560 | |

```
cgcatcgcct tctatcgcct tcttgacgag ttcttctgaa ttattaacgc ttacaatttc    1620
ctgatgcggt attttctcct tacgcatctg tgcggtattt cacaccgcat acaggtggca    1680
cttttcgggg aaatgtgcgc ggaacccta tttgtttatt tttctaaata cattcaaata    1740
tgtatccgct catgagacaa taaccctgat aaatgcttca ataatagcac gtgctaaaac    1800 ttcatttta atttaaaagg atctaggtga agatccttt tgataatctc atgaccaaaa    1860
tcccttaacg tgagttttcg ttccactgag cgtcagaccc cgtagaaaag atcaaaggat    1920
cttcttgaga tccttttttt ctgcgcgtaa tctgctgctt gcaaacaaaa aaaccaccgc    1980
taccagcggt ggtttgtttg ccggatcaag agctaccaac tcttttccg aaggtaactg    2040 gcttcagcag agcgcagata ccaaatactg tccttctagt gtagccgtag ttaggccacc    2100
acttcaagaa ctctgtagca ccgcctacat acctcgctct gctaatcctg ttaccagtgg    2160
ctgctgccag tggcgataag tcgtgtctta ccgggttgga ctcaagacga tagttaccgg    2220
ataaggcgca gcggtcgggc tgaacggggg gttcgtgcac acagcccagc ttggagcgaa    2280
cgacctacac cgaactgaga tacctacagc gtgagctatg agaaagcgcc acgcttcccg    2340
aagggagaaa ggcggacagg tatccggtaa gcggcagggt cggaacagga gagcgcacga    2400
gggagcttcc agggggaaac gcctggtatc tttatagtcc tgtcgggttt cgccacctct    2460
gacttgagcg tcgatttttg tgatgctcgt caggggggcg gagcctatgg aaaaacgcca    2520
gcaacgcggc cttttacgg ttcctgggct tttgctggcc ttttgctcac atgttctt    2578
```

<210> SEQ ID NO 8
<211> LENGTH: 3978
<212> TYPE: DNA
<213> ORGANISM: Artificial Sequence
<220> FEATURE:
<223> OTHER INFORMATION: nucleotide sequence of pMVA-4

<400> SEQUENCE: 8

```
gactcttcgc gatgtacggg ccagatatac gctacgttgt agctcacttc cactatgtcc      60
tatcaatagg agctgtattt gccatcatag gaggcttcat tcactgattt ccccctattct     120 caggctacac cctagaccaa acctacgcca aaatccattt cactatcata ttcatcggcg     180
taaatctaac tttcttccca caacactttc tcggcctatc cggaatgccc cgacgttact     240
cggactaccc cgatgcatac accacatgaa acatcctatc atctgtaggc tcattcattt     300
ctctaacagc agtaatatta ataattttca tgatttgaga agccttcgct tcgaagcgaa     360
aagtcctaat agtagaagaa ccctccataa acctggagtg actatatgga tgccccccac     420
cctaccacac attcgaagaa cccgtataca taaaatctag acaaaaaagg aaggaatcga     480
accccccaaa gctggtttca agccaacccc atggcctcca tgacttttc aaaaaggtat     540 tagaaaaacc atttcataac tttgtcaaag ttaaattata ggctaaatcc tatatatctt     600
aatggcacat gcagcgcaag taggtctaca agacgctact tcccctatca tagaagagct     660
tatcaccttt catgatcacg ccctcataat catttttctt atctgcttcc tagtcctgta     720 tgccctttc ctaacactca aacaaaact aactaatact aacatctcag acgctcagga     780
aatagaaacc gtctgaacta tcctgcccgc catcatccta gtcctcatcg ccctcccatc     840
cctacgcatc ctttacataa cagacgaggt caacgatccc tccttacca tcaaatcaat     900 tggccaccaa tggtactgaa cctacgagta caccgactac ggcggactaa tcttcaactc     960
ctacatactt ccccccattat tcctagaacc aggcgacctg cgactccttg acgttgacaa    1020
```

```
tcgagtagta ctcccgattg aagcccccat tcgtataata attacatcac aagacgtctt    1080
gcactcatga gctgtcccca cattaggctt aaaaacagat gcaattcccg gacgtctaaa    1140
ccaaaccact ttcaccgcta cacgaccggg ggtatactac ggtcaatgct ctgaaatctg    1200
tggagcaaac cacagtttca tgcccatcgt cctagaatta attcccctaa aaatctttga    1260
aatagggccc gtatttaccc tatagcaccc cctctacccc ctctagagcc cactgtaaag    1320
ctaacttagc attaaccttt taagttaaag attaagagaa ccaacacctc tttacagtga    1380
aatgccccaa ctaaatacta ccgtatggcc caccataatt accccatac tccttacact     1440 attcctcatc acccaactaa aaatattaaa cacaaactac cacctacctc cctcaccaaa    1500
gcccataaaa ataaaaaatt ataacaaacc ctgagaacca aaatgaacga aaatctgttc    1560
gcttcattca ttgcccccac aatcctaggc ctacccgccg cagtactgat cattctattt    1620 cccctctat tgatccccac ctccaaatat ctcatcaaca accgactaat caccacccaa     1680
caatgactaa tcaaactaac ctcaaaacaa atgataacca tacacaacac taaaggacga    1740
acctgatctc ttatactagt atccttaatc attttattg ccacaactaa cctcctcgga     1800
ctcctgcctc actcatttac accaaccacc caactatcta taaacctagc catggccatc    1860
cccttatgag cgggcgcagt gattataggc tttcgctcta agattaaaaa tgccctagcc    1920
cacttcttac cacaaggcac acctacaccc cttatcccca tactagttat tatcgaaacc    1980
atcagcctac tcattcaacc aatagccctg gccgtacgcc taaccgctaa cacttctact    2040
gggcggtttt atggacagca agcgaaccgg aattgccagc tggggcgccc tctggtaagg    2100
ttgggaagcc ctgcaaagta aactggatgg ctttctcgcc gccaaggatc tgatggcgca    2160
ggggatcaag ctctgatcaa gagacaggat gaggatcgtt tcgcatgatt gaacaagatg    2220
gattgcacgc aggttctccg gccgcttggg tggagaggct attcggctat gactgggcac    2280
aacagacaat cggctgctct gatgccgccg tgttccggct gtcagcgcag ggcgcccgg     2340 ttcttttgt caagaccgac ctgtccggtg ccctgaatga actgcaagac gaggcagcgc     2400
ggctatcgtg gctggccacg acgggcgttc cttgcgcagc tgtgctcgac gttgtcactg    2460
aagcgggaag ggactggctg ctattgggcg aagtgccggg gcaggatctc ctgtcatctc    2520
accttgctcc tgccgagaaa gtatccatca tggctgatgc aatgcggcgg ctgcatacgc    2580
ttgatccggc tacctgccca ttcgaccacc aagcgaaaca tcgcatcgag cgagcacgta    2640
ctcggatgga agccggtctt gtcgatcagg atgatctgga cgaagagcat caggggctcg    2700
cgccagccga actgttcgcc aggctcaagg cgagcatgcc cgacggcgag gatctcgtcg    2760
tgacccatgg cgatgcctgc ttgccgaata tcatggtgga aaatggccgc ttttctggat    2820
tcatcgactg tggccggctg ggtgtggcgg accgctatca ggacatagcg ttggctaccc    2880
gtgatattgc tgaagagctt ggcggcgaat gggctgaccg cttcctcgtg ctttacggta    2940
tcgccgctcc cgattcgcag cgcatcgcct tctatcgcct tcttgacgag ttcttctgaa    3000
ttattaacgc ttacaatttc ctgatgcggt attttctcct tacgcatctg tgcggtattt    3060
cacaccgcat acaggtggca cttttcgggg aaatgtgcgc ggaaccccta tttgtttatt    3120
tttctaaata cattcaaata tgtatccgct catgagacaa taaccctgat aaatgcttca    3180
ataatagcac gtgctaaaac ttcattttta atttaaaagg atctaggtga agatcctttt    3240
tgataatctc atgaccaaaa tcccttaacg tgagttttcg ttccactgag cgtcagaccc    3300
cgtagaaaag atcaaaggat cttcttgaga tcctttttt ctgcgcgtaa tctgctgctt     3360
gcaaacaaaa aaccaccgc taccagcggt ggtttgtttg ccggatcaag agctaccaac     3420
```

| | | |
|---|---|---|
| tcttttttccg aaggtaactg gcttcagcag agcgcagata ccaaatactg tccttctagt | 3480 | |
| gtagccgtag ttaggccacc acttcaagaa ctctgtagca ccgcctacat acctcgctct | 3540 | |
| gctaatcctg ttaccagtgg ctgctgccag tggcgataag tcgtgtctta ccgggttgga | 3600 | |
| ctcaagacga tagttaccgg ataaggcgca gcggtcgggc tgaacggggg gttcgtgcac | 3660 | |
| acagcccagc ttggagcgaa cgacctacac cgaactgaga tacctacagc gtgagctatg | 3720 | |
| agaaagcgcc acgcttcccg aagggagaaa ggcggacagg tatccggtaa gcggcagggt | 3780 | |
| cggaacagga gagcgcacga gggagcttcc aggggggaaac gcctggtatc tttatagtcc | 3840 | |
| tgtcgggttt cgccacctct gacttgagcg tcgatttttg tgatgctcgt caggggggcg | 3900 | |
| gagcctatgg aaaaacgcca gcaacgcggc cttttttacgg ttcctgggct tttgctggcc | 3960 | |
| ttttgctcac atgttctt | 3978 | |

<210> SEQ ID NO 9
<211> LENGTH: 2097
<212> TYPE: DNA
<213> ORGANISM: Artificial Sequence
<220> FEATURE:
<223> OTHER INFORMATION: nucleotide sequence of pMVA-5

<400> SEQUENCE: 9

| | | |
|---|---|---|
| gctgcttcgc gatgtacggg ccagatatac gcccattat tcctagaacc aggcgacctg | 60 | |
| cgactccttg acgttgacaa tcgagtagta ctcccgattg aagcccccat tcgtataata | 120 | |
| attacatcac aagacgtctt gcactcatga gccttctact gggcggtttt atggacagca | 180 | |
| agcgaaccgg aattgccagc tggggcgccc tctggtaagg ttgggaagcc ctgcaaagta | 240 | |
| aactggatgg cttttcttgcc gccaaggatc tgatggcgca ggggatcaag ctctgatcaa | 300 | |
| gagacaggat gaggatcgtt tcgcatgatt gaacaagatg gattgcacgc aggttctccg | 360 | |
| gccgcttggg tggagaggct attcggctat gactgggcac aacagacaat cggctgctct | 420 | |
| gatgccgccg tgttccggct gtcagcgcag gggcgcccgg ttcttttttgt caagaccgac | 480 | |
| ctgtccggtg ccctgaatga actgcaagac gaggcagcgc ggctatcgtg gctggccacg | 540 | |
| acgggcgttc cttgcgcagc tgtgctcgac gttgtcactg aagcgggaag ggactggctg | 600 | |
| ctattgggcg aagtgccggg gcaggatctc ctgtcatctc accttgctcc tgccgagaaa | 660 | |
| gtatccatca tggctgatgc aatgcggcgg ctgcatacgc ttgatccggc tacctgccca | 720 | |
| ttcgaccacc aagcgaaaca tcgcatcgag cgagcacgta ctcggatgga agccggtctt | 780 | |
| gtcgatcagg atgatctgga cgaagagcat caggggctcg cgccagccga actgttcgcc | 840 | |
| aggctcaagg cgagcatgcc cgacggcgag gatctcgtcg tgacccatgg cgatgcctgc | 900 | |
| ttgccgaata tcatggtgga aaatggccgc ttttctggat tcatcgactg tggccggctg | 960 | |
| ggtgtggcgg accgctatca ggacatagcg ttggctaccc gtgatattgc tgaagagctt | 1020 | |
| ggcggcgaat gggctgaccg cttcctcgtg ctttacggta tcgccgctcc cgattcgcag | 1080 | |
| cgcatcgcct tctatcgcct tcttgacgag ttcttctgaa ttattaacgc ttacaatttc | 1140 | |
| ctgatgcggt atttctcct tacgcatctg tgcggtattt cacaccgcat caggtggcac | 1200 | |
| ttttcgggga atgtgcgcg gaaccccttat tgtttattt ttctaaatac attcaaatat | 1260 | |
| gtatccgctc atgagacaat aaccctgata aatgcttcaa taatagcacg tgctaaaact | 1320 | |
| tcatttttaa tttaaaagga tctaggtgaa gatcctttt gataatctca tgaccaaaat | 1380 | |
| cccttaacgt gagttttcgt tccactgagc gtcagacccc gtagaaaaga tcaaaggatc | 1440 | |

-continued

```
ttcttgagat cctttttttc tgcgcgtaat ctgctgcttg caaacaaaaa aaccaccgct      1500
accagcggtg gtttgtttgc cggatcaaga gctaccaact cttttttccga aggtaactgg     1560 cttcagcaga gcgcagatac caaatactgt tcttctagtg tagccgtagt taggccacca     1620
cttcaagaac tctgtagcac cgcctacata cctcgctctg ctaatcctgt taccagtggc    1680
tgctgccagt ggcgataagt cgtgtcttac cgggttggac tcaagacgat agttaccgga    1740
taaggcgcag cggtcgggct gaacggggg ttcgtgcaca cagcccagct tggagcgaac     1800
gacctacacc gaactgagat acctacagcg tgagctatga gaaagcgcca cgcttcccga     1860
agggagaaag gcggacaggt atccggtaag cggcagggtc ggaacaggag agcgcacgag    1920
ggagcttcca gggggaaacg cctggtatct ttatagtcct gtcgggtttc gccacctctg    1980
acttgagcgt cgatttttgt gatgctcgtc agggggggcgg agcctatgga aaaacgccag    2040
caacgcggcc ttttacggt tcctggcctt ttgctggcct tttgctcaca tgttctt        2097
```

<210> SEQ ID NO 10
<211> LENGTH: 2577
<212> TYPE: DNA
<213> ORGANISM: Artificial Sequence
<220> FEATURE:
<223> OTHER INFORMATION: nucleotide sequence of pMVA-6

<400> SEQUENCE: 10

```
gctgcttcgc gatgtacggg ccagatatac gcctgaacta cctgcccgc catcatccta      60 gtcctcatcg ccctcccatc cctacgcatc ctttacataa cagacgaggt caacgatccc    120
tcccttacca tcaaatcaat tggccaccaa tggtactgaa cctacgagta caccgactac    180
ggcggactaa tcttcaactc ctacatactt cccccattat tcctagaacc aggcgacctg    240
cgactccttg acgttgacaa tcgagtagta ctcccgattg aagcccccat tcgtataata    300
attacatcac aagacgtctt gcactcatga gctgtcccca cattaggctt aaaaacagat    360
gcaattcccg gacgtctaaa ccaaaccact ttcaccgcta cacgaccggg gtatactac      420 ggtcaatgct ctgaaatctg tggagcaaac cacagtttca tgcccatcgt cctagaatta    480
attcccctaa aaatctttga aatagggccc gtatttaccc tatagcaccc cctctacccc    540
ctctagagcc cactgtaaag ctaacttagc attaaccttt taagttaaag attaagagaa    600
ccaacacctc tttacagtga aatgccccaa ctcttctact gggcggtttt atggacagca    660
agcgaaccgg aattgccagc tggggcgccc tctggtaagg ttgggaagcc ctgcaaagta    720
aactggatgg ctttcttgcc gccaaggatc tgatggcgca ggggatcaag ctctgatcaa    780
gagacaggat gaggatcgtt tcgcatgatt gaacaagatg gattgcacgc aggttctccg    840
gccgcttggg tggagaggct attcggctat gactgggcac aacagacaat cggctgctct    900
gatgccgccg tgttccggct gtcagcgcag gggcgcccgg ttcttttttgt caagaccgac    960 ctgtccggtg ccctgaatga actgcaagac gaggcagcgc ggctatcgtg gctggccacg    1020
acgggcgttc cttgcgcagc tgtgctcgac gttgtcactg aagcgggaag ggactggctg    1080
ctattgggcg aagtgccggg gcaggatctc ctgtcatctc accttgctcc tgccgagaaa    1140
gtatccatca tggctgatgc aatgcggcgg ctgcatacgc ttgatccggc tacctgccca    1200
ttcgaccacc aagcgaaaca tcgcatcgag cgagcacgta ctcggatgga agccggtctt    1260
gtcgatcagg atgatctgga cgaagagcat caggggctcg cgccagccga actgttcgcc    1320
aggctcaagg cgagcatgcc cgacggcgag gatctcgtcg tgacccatgg cgatgcctgc    1380
ttgccgaata tcatggtgga aaatggccgc ttttctggat tcatcgactg tggccggctg    1440
```

| | |
|---|---|
| ggtgtggcgg accgctatca ggacatagcg ttggctaccc gtgatattgc tgaagagctt | 1500 |
| ggcggcgaat gggctgaccg cttcctcgtg ctttacggta tcgccgctcc cgattcgcag | 1560 |
| cgcatcgcct tctatcgcct tcttgacgag ttcttctgaa ttattaacgc ttacaatttc | 1620 |
| ctgatgcggt attttctcct tacgcatctg tgcggtattt cacaccgcat caggtggcac | 1680 |
| ttttcgggga atgtgcgcg gaacccctat tgtttatttt tctaaatac attcaaatat | 1740 |
| gtatccgctc atgagacaat aaccctgata aatgcttcaa taatagcacg tgctaaaact | 1800 |
| tcattttta tttaaaagga tctaggtgaa gatcctttt gataatctca tgaccaaaat | 1860 |
| cccttaacgt gagttttcgt tccactgagc gtcagacccc gtagaaaaga tcaaaggatc | 1920 |
| ttcttgagat cctttttttc tgcgcgtaat ctgctgcttg caaacaaaaa aaccaccgct | 1980 |
| accagcggtg gtttgtttgc cggatcaaga gctaccaact cttttccga aggtaactgg | 2040 |
| cttcagcaga gcgcagatac caaatactgt tcttctagtg tagccgtagt taggccacca | 2100 |
| cttcaagaac tctgtagcac cgcctacata cctcgctctg ctaatcctgt taccagtggc | 2160 |
| tgctgccagt ggcgataagt cgtgtcttac cgggttggac tcaagacgat agttaccgga | 2220 |
| taaggcgcag cggtcgggct gaacggggggt tcgtgcaca cagcccagct tggagcgaac | 2280 |
| gacctacacc gaactgagat acctacagcg tgagctatga gaaagcgcca cgcttcccga | 2340 |
| agggagaaag gcggacaggt atccggtaag cggcagggtc ggaacaggag agcgcacgag | 2400 |
| ggagcttcca gggggaaacg cctggtatct ttatagtcct gtcgggtttc gccacctctg | 2460 |
| acttgagcgt cgattttgt gatgctcgtc agggggggcgg agcctatgga aaaacgccag | 2520 |
| caacgcggcc ttttacggt tcctggcctt ttgctggcct tttgctcaca tgttctt | 2577 |

<210> SEQ ID NO 11
<211> LENGTH: 3977
<212> TYPE: DNA
<213> ORGANISM: Artificial Sequence
<220> FEATURE:
<223> OTHER INFORMATION: nucleotide sequence of pMVA-7

<400> SEQUENCE: 11

| | |
|---|---|
| gctgcttcgc gatgtacggg ccagatatac gctacgttgt agctcacttc cactatgtcc | 60 |
| tatcaatagg agctgtattt gccatcatag gaggcttcat tcactgattt ccctattct | 120 |
| caggctacac cctagaccaa acctacgcca aaatccattt cactatcata ttcatcggcg | 180 |
| taaatctaac tttcttccca caacacttc tcggcctatc cggaatgccc cgacgttact | 240 |
| cggactaccc cgatgcatac accacatgaa acatcctatc atctgtaggc tcattcattt | 300 |
| ctctaacagc agtaatatta ataattttca tgatttgaga agccttcgct tcgaagcgaa | 360 |
| aagtcctaat agtagaagaa ccctccataa acctggagtg actatatgga tgccccac | 420 |
| cctaccacac attcgaagaa cccgtataca taaatctag acaaaaaagg aaggaatcga | 480 |
| acccccaaa gctggtttca agccaacccc atggcctcca tgacttttc aaaaaggtat | 540 |
| tagaaaaacc atttcataac tttgtcaaag ttaaattata ggctaaatcc tatatatctt | 600 |
| aatggcacat gcagcgcaag taggtctaca agacgctact tcccctatca tagaagagct | 660 |
| tatcaccttt catgatcacg ccctcataat catttttcctt atctgcttcc tagtcctgta | 720 |
| tgccctttc ctaacactca aacaaaaact aactaatact aacatctcag acgctcagga | 780 |
| aatagaaacc gtctgaacta tcctgcccgc catcatccta gtcctcatcg ccctcccatc | 840 |
| cctacgcatc ctttacataa cagacgaggt caacgatccc tcccttacca tcaaatcaat | 900 |

```
tggccaccaa tggtactgaa cctacgagta caccgactac ggcggactaa tcttcaactc    960
ctacatactt cccccattat tcctagaacc aggcgacctg cgactccttg acgttgacaa   1020
tcgagtagta ctcccgattg aagcccccat tcgtataata attacatcac aagacgtctt   1080
gcactcatga gctgtcccca cattaggctt aaaaacagat gcaattcccg gacgtctaaa   1140
ccaaaccact ttcaccgcta cacgaccggg ggtatactac ggtcaatgct ctgaaatctg   1200
tggagcaaac cacagtttca tgcccatcgt cctagaatta attcccctaa aaatctttga   1260
aatagggccc gtatttaccc tatagcaccc cctctacccc ctctagagcc cactgtaaag   1320
ctaacttagc attaaccttt taagttaaag attaagagaa ccaacacctc tttacagtga   1380
aatgccccaa ctaaatacta ccgtatggcc caccataatt accccatac tccttacact   1440 attcctcatc acccaactaa aaatattaaa cacaaactac cacctacctc cctcaccaaa   1500
gcccataaaa ataaaaaatt ataacaaacc ctgagaacca aaatgaacga aaatctgttc   1560
gcttcattca ttgccccac aatcctaggc ctacccgccg cagtactgat cattctattt   1620
ccccctctat tgatccccac ctccaaatat ctcatcaaca accgactaat caccacccaa   1680
caatgactaa tcaaactaac ctcaaaacaa atgataacca tacacaacac taaaggacga   1740
acctgatctc ttatactagt atccttaatc attttattg ccacaactaa cctcctcgga   1800
ctcctgcctc actcatttac accaaccacc caactatcta taaacctagc catggccatc   1860
cccttatgag cgggcgcagt gattataggc tttcgctcta agattaaaaa tgccctagcc   1920
cacttcttac cacaaggcac acctacaccc cttatcccca tactagttat tatcgaaacc   1980
atcagcctac tcattcaacc aatagccctg gccgtacgcc taaccgctaa cacttctact   2040
gggcggtttt atggacagca agcgaaccgg aattgccagc tggggcgccc tctggtaagg   2100
ttgggaagcc ctgcaaagta aactggatgg cttctcttgcc gccaaggatc tgatggcgca   2160
ggggatcaag ctctgatcaa gagacaggat gaggatcgtt tcgcatgatt gaacaagatg   2220 gattgcacg aggttctccg gccgcttggg tggagaggct attcggctat gactgggcac   2280
aacagacaat cggctgctct gatgccgccg tgttccggct gtcagcgcag ggcgcccgg    2340 ttcttttttgt caagaccgac ctgtccggtg ccctgaatga actgcaagac gaggcagcgc   2400
ggctatcgtg gctggccacg acgggcgttc cttgcgcagc tgtgctcgac gttgtcactg   2460
aagcgggaag ggactggctg ctattgggcg aagtgccggg gcaggatctc ctgtcatctc   2520
accttgctcc tgccgagaaa gtatccatca tggctgatgc aatgcggcgg ctgcatacgc   2580
ttgatccggc tacctgccca ttcgaccacc aagcgaaaca tcgcatcgag cgagcacgta   2640
ctcggatgga agccggtctt gtcgatcagg atgatctgga cgaagagcat caggggctcg   2700
cgccagccga actgttcgcc aggctcaagg cgagcatgcc cgacggcgag gatctcgtcg   2760
tgacccatgg cgatgcctgc ttgccgaata tcatggtgga aaatggccgc ttttctggat   2820
tcatcgactg tggccggctg ggtgtggcgg accgctatca ggacatagcg ttggctaccc   2880
gtgatattgc tgaagagctt ggcggcgaat gggctgaccg cttcctcgtg ctttacggta   2940
tcgccgctcc cgattcgcag cgcatcgcct tctatcgcct tcttgacgag ttcttctgaa   3000
ttattaacgc ttacaatttc ctgatgcggt attttctcct tacgcatctg tgcggtattt   3060
cacaccgcat caggtggcac ttttcgggga aatgtgcgcg gaaccctat ttgtttattt   3120 ttctaaatac attcaaatat gtatccgctc atgagacaat aaccctgata aatgcttcaa   3180
taatagcacg tgctaaaact tcatttttaa tttaaaagga tctaggtgaa gatcctttt    3240 gataatctca tgaccaaaat cccttaacgt gagttttcgt tccactgagc gtcagacccc   3300
```

```
gtagaaaaga tcaaaggatc ttcttgagat ccttttttc tgcgcgtaat ctgctgcttg    3360
caaacaaaaa aaccaccgct accagcggtg gtttgtttgc cggatcaaga gctaccaact    3420 cttttccga aggtaactgg cttcagcaga gcgcagatac caaatactgt tcttctagtg    3480
tagccgtagt taggccacca cttcaagaac tctgtagcac cgcctacata cctcgctctg    3540
ctaatcctgt taccagtggc tgctgccagt ggcgataagt cgtgtcttac cgggttggac    3600
tcaagacgat agttaccgga taaggcgcag cggtcgggct gaacggggg ttcgtgcaca    3660 cagcccagct tggagcgaac gacctacacc gaactgagat acctacagcg tgagctatga    3720
gaaagcgcca cgcttcccga agggagaaag gcggacaggt atccggtaag cggcagggtc    3780
ggaacaggag agcgcacgag ggagcttcca gggggaaacg cctggtatct ttatagtcct    3840
gtcgggtttc gccacctctg acttgagcgt cgattttgt gatgctcgtc aggggggcgg    3900
agcctatgga aaaacgccag caacgcggcc tttttacggt tcctggcctt ttgctggcct    3960
tttgctcaca tgttctt                                                    3977
```

The invention claimed is:

1. A tumor vaccine, comprising a complex formed by DNA and a cationic biomaterial, wherein:
   (a) the DNA has a length of 50-10000 bp and is a pMVA-1 plasmid;
   (b) the pMVA-1 plasmid is replicable and comprises a replicon, a resistance gene, and a plasmid backbone sequence but is unable to express an exogenous gene;
   (c) the nucleotide sequence of the pMVA-1 plasmid comprises the nucleotide sequence of SEQ ID NO. 2;
   (d) the cationic biomaterial is at least one of a cationic lipid material and a cationic polymer;
   (e) the cationic polymer is at least one member selected from the group consisting of polyethyleneimine, a polysaccharide, polyamide-amine (PAMAM), and a polymer containing an imidazole group; and
   (f) the cationic lipid material includes at least one of N-[1-(2,3-dioleyloxy) propyl]-N,N,N-trimethylammonium chloride (DOTMA), 1,2-dioleoyl-3-trimethylammonium-propane (DOTAP), dodecyltrimethylammonium bromide (DTAB), tetradecyltrimethylammonium bromide (TTAB), cetyltrimethylammonium bromide (CTAB), and dimethyldioctadecylammonium bromide (DDAB).

2. The tumor vaccine according to claim 1, wherein the DNA has a length of 100-6000 bp.

3. The tumor vaccine according to claim 1, wherein the pMVA-1 plasmid is loaded with other DNA, wherein the other DNA is DNA which is not from the pMVA-1 plasmid.

4. The tumor vaccine according to claim 3, wherein the other DNA has a length of 50-3000 bp.

5. The tumor vaccine according to claim 4, wherein the other DNA has a length of 100-2500 bp.

6. The tumor vaccine according to claim 3, wherein the other DNA is mitochondrial DNA or a mitochondrial DNA fragment.

7. The tumor vaccine according to claim 6, wherein the mitochondrial DNA fragment is selected from at least one DNA fragment comprising the nucleotide sequences of SEQ ID NO. 3, SEQ ID NO. 4 or SEQ ID NO. 5, or DNA fragments comprising the nucleotide sequences that are at least 90% identical to SEQ ID NO. 3, SEQ ID NO. 4 or SEQ ID NO. 5.

8. The tumor vaccine according to claim 1, wherein the DNA is oxidized DNA.

9. The tumor vaccine according to claim 8, wherein the oxidized DNA is formed in vitro by irradiation or treatment with oxidizing agents.

10. The tumor vaccine according to claim 9, wherein the irradiation is at least one of irradiation with ultraviolet rays, gamma rays and X-rays; and the oxidizing agent is at least one of oxygen, ozone, $F_2$, $Cl_2$, $Br_2$, nitrate, chlorate, perchlorate, $HNO_3$, $KMnO_4$, $NaClO$, $CrO_3$, $H_2O_2$, $PbO_2$, $NaBiO_3$, $XeF_2$, $Ce^{4+}$ and $PdCl_2$.

11. The tumor vaccine according to claim 1, wherein the cationic lipid material is at least one of a) a cationic lipid and b) a complex formed by a cationic lipid and a helper lipid.

12. The tumor vaccine according to claim 11, wherein the helper lipid is selected from at least one of phosphatidyl ethanolamine (PE), phosphatidylcholine (PC), cholesterol (Chol), and dioleoyl phosphoethanolamine (DOPE).

13. The tumor vaccine according to claim 11, wherein a mass ratio of the cationic lipid to the helper lipid in the complex formed thereby is 1:0.1 to 1:10.

14. The tumor vaccine according to claim 1, wherein the polyethyleneimine has a molecular weight of 2-30 kD.

15. The tumor vaccine according to claim 14, wherein the polyethyleneimine is PEI 2 kD, PEI 5 kD or PEI 25 kD.

16. The tumor vaccine according to claim 1, wherein the polysaccharide is selected from at least one of chitosan, carboxymethyl chitosan, trimethyl chitosan, and chitosan quaternary ammonium salt.

17. The tumor vaccine according to claim 16, wherein the polysaccharide has a molecular weight of 30-50 kD.

18. The tumor vaccine according to claim 1, wherein a mass ratio of the DNA to the cationic biomaterial in the complex formed thereby is 1:1 to 1:100.

19. The tumor vaccine according to claim 18, wherein the mass ratio of the DNA to the cationic biomaterial in the complex formed thereby is 1:1 to 1:50.

20. The tumor vaccine according to claim 1, wherein the complex has a particle diameter of 1-2,000 nm.

21. The tumor vaccine according to claim 20, wherein the particle diameter is 50-1,000 nm.

22. The tumor vaccine according to claim 1, wherein the complex has a potential of 1-150 mV, and wherein the cationic lipid material comprises at least one of a) DOTAP and b) a complex of DOTAP with a cholesterol (CHOL) helper lipid.

23. The tumor vaccine according to claim 22, wherein the potential is 5-100 mV.

24. A pharmaceutical composition, comprising the tumor vaccine according to claim 1 and a pharmaceutically acceptable excipient or auxiliary component.

25. The pharmaceutical composition according to claim 24, wherein the excipient or auxiliary component is at least one of a diluent, an excipient, a filler, a binder, a wetting agent, a disintegrant, an absorption enhancer, a surfactant, a protective agent, an adsorption carrier and a lubricant.

26. A medical kit, comprising the tumor vaccine according to claim 1, and at least one other drug for treating a tumor.

27. The medical kit according to claim 26, wherein the other drug for treating a tumor is selected from at least one of a chemotherapeutic drug and an immune response modifier.

28. The medical kit according to claim 27, wherein the immune response modifier is at least one of a cytokine, a class II HLA protein-binding accessory molecule, a CD40 agonist, a checkpoint receptor antagonist, a B7 costimulatory molecule, a FLt3 agonist and a CD40L agonist.

29. An antitumor drug, comprising the tumor vaccine according to claim 1 and a tumor antigen.

30. The antitumor drug according to claim 29, wherein the tumor antigen is selected from at least one of a tumor-associated antigen, an apoptotic tumor cell and a necrotic tumor cell.

31. A method for manufacturing a drug for treating a tumor, comprising the steps of:
providing the tumor vaccine of claim 1,
adding a pharmaceutically acceptable excipient or auxiliary component to the tumor vaccine of claim 1 before and/or during and/or after combining said DNA and cationic biomaterial,
thereby preparing the drug for treating a tumor.

32. A method for the preparation of a drug for treating a tumor, comprising the steps of:
providing the tumor vaccine of claim 1,
providing at least one other drug for treating a tumor,
adding the tumor vaccine of claim 1, at least one other drug for treating a tumor, and a pharmaceutically acceptable excipient or auxiliary component to the tumor vaccine of claim 1 before and/or during and/or after combining said DNA and cationic biomaterial,
thereby preparing the drug for treating a tumor.

33. The method according to claim 32, wherein the other drug for treating a tumor is selected from at least one of a chemotherapeutic drug or an immune response modifier.

34. The method according to claim 33, wherein the immune response modifier is at least one of a cytokine, a class II HLA protein-binding accessory molecule, a CD40 agonist, a checkpoint receptor antagonist, a B7 costimulatory molecule, a FLt3 agonist or a CD40L agonist.

35. A method for treating a tumor, comprising the step of administering a therapeutically effective amount of the tumor vaccine according to claim 1 to a mammal having tumor.

36. The method according to claim 35, wherein the mammal is a mouse, a dog, a monkey or a human being.

37. The method according to claim 35, wherein the tumor is selected from cervical cancer, ovarian cancer, breast cancer, lung cancer, nasopharyngeal cancer, gastric cancer, pancreatic cancer, esophageal cancer, colon cancer, rectal cancer, liver cancer, prostate cancer, kidney cancer, bladder cancer, skin cancer, sarcoma, and lymphoma.

38. A method for preparing the tumor vaccine according to claim 1, comprising the steps of: (1) preparing the DNA and the cationic biomaterial; and (2) mixing the DNA with the cationic biomaterial in Step (1), and allowing the tumor vaccine components in claim 1 to stand so as to obtain the tumor vaccine.

39. A method for preparing the pharmaceutical composition according to claim 24, comprising the steps of: (1) preparing DNA and cationic biomaterial; (2) mixing the DNA with the cationic biomaterial in Step (1), and adding a pharmaceutically acceptable excipient or auxiliary component to the tumor vaccine components in claim 1 before and/or during and/or after mixing of the DNA and the cationic biomaterial so as to prepare the pharmaceutical composition.

* * * * *